United States Patent [19]

Larsson

[11] Patent Number: 5,650,524

[45] Date of Patent: Jul. 22, 1997

[54] PROCESS FOR PREPARING (R)-3-AMINO-5-METHOXYCHROMAN

[75] Inventor: Lars-Gunnar Larsson, Hölö, Sweden

[73] Assignee: Astra Aktiebolag, Sodertalje, Sweden

[21] Appl. No.: 451,983

[22] Filed: May 26, 1995

Related U.S. Application Data

[60] Division of Ser. No. 144,671, Oct. 28, 1993, Pat. No. 5,420,151, which is a continuation-in-part of Ser. No. 780, 531, Oct. 18, 1991, abandoned, and Ser. No. 957,214, Oct. 6, 1992, abandoned, which is a continuation-in-part of Ser. No. 780,531, which is a continuation-in-part of Ser. No. 633,247, Dec. 21, 1990, abandoned.

[30] Foreign Application Priority Data

Dec. 22, 1989 [SE] Sweden .................... 8904361
Oct. 8, 1991 [SE] Sweden .................... 9102905
Jun. 29, 1992 [SE] Sweden .................... 9202000

[51] Int. Cl.$^6$ ............................ C07D 311/58
[52] U.S. Cl. ............................ 549/404; 558/354
[58] Field of Search ............................ 558/354; 549/404

[56] References Cited

U.S. PATENT DOCUMENTS

| 3,976,680 | 8/1976 | Clark et al. | 260/471 |
| 4,656,303 | 4/1987 | Kurono et al. | 558/354 |
| 4,683,223 | 7/1987 | Trivedi | 514/46 |
| 4,801,605 | 1/1989 | Hutchinson | 514/432 |
| 4,873,262 | 10/1989 | Junge et al. | 514/510 |
| 4,971,982 | 11/1990 | Attwood et al. | 514/337 |
| 5,026,707 | 6/1991 | Nixon | 514/255 |
| 5,082,858 | 1/1992 | Garcia et al. | 514/456 |
| 5,214,156 | 5/1993 | Andersson et al. | 549/75 |
| 5,225,596 | 7/1993 | Carlsson et al. | 564/428 |
| 5,306,830 | 4/1994 | Andersson et al. | 549/404 |

FOREIGN PATENT DOCUMENTS

| 0222996 | 5/1987 | European Pat. Off. . |
| 0231139 | 8/1987 | European Pat. Off. . |
| 0280269 | 8/1988 | European Pat. Off. . |
| 0343830 | 11/1989 | European Pat. Off. . |
| 0385658 | 9/1990 | European Pat. Off. . |
| 8804654 | 6/1988 | WIPO . |
| 9109983 | 7/1991 | WIPO . |

OTHER PUBLICATIONS

Traber, et al. "5-HT$_{1A}$ receptor–related anxiolytics", TIPS, 8:432–437, 1987.
Samanin, et al. "Serotonin and the Pharmacology of Eating", Annals N.Y. Acad. Sci. 575:194–208, 1989.
Bowen, et al. "Circumscribed changes of the cerebral cortex in neuropsychiatric disorders of later life", Proc. Natl. Acad. Sci. (USA) 86:9504–9508, 1989.
Dabire, et al. "Comparison of effects of some 5-HT$_1$ agonists on blood pressure and heart rate of normotensive anaesthesized rats", Eur. J. Pharm. 140:259–266, 1987.
Archer, et al. "(+)-8-OH-DPAT and MeODMT Induced Analgesia is Antagonised by Noradrenaline Depletion", Physiol. and Beh. 39:95–102, 1987.
Hjorth, S. "Hypothermia in the Rat Induced by the Potent Serotoninergic Agent 8–OH–DPAT", J. Neur. Transm. pp. 131–135, 1985.
Kennett, et al. "Antidepressant–like action of 5-HT$_{1A}$ Agonists and conventional antidepressants in an animal model of depression", Eur. J. Pharm. 134:265–274, 1982.
Lockhart, et al., Journal of Medicinal Chemistry, vol. 15, No. 8, pp. 863–865 (1972).
SCRIP's Serotonin Report No. 1184, 1987.
Hutchison, et al. "Preparation of 3–Aminodihydro[1]benzopyran and Benzothiopyran Derivatives as Seratoninergic Agonists", Chem. Abs. 107:39617j, Feb. 1987.
Hershenson, et al. "Annual Reports in Medicinal, Chemistry", D. Bailey Ed., 21:31–40, Acad. Press, N.Y., 1986.
Foye, W. "Principles of Medicinal Chemistry", 2nd ed. pp. 80–81, Lea & Febiger, Philadelphia, 1981.
Jacques et al. "Enantiomers, Racemates, & Resolutions," John Wiley & Sons, NY, 1981.

Primary Examiner—José G. Dees
Assistant Examiner—Mary Cebulak
Attorney, Agent, or Firm—White & Case

[57] ABSTRACT

A process for preparing (R)-3-amino-5-methoxychroman is provided. The process comprises the steps of (i) dissolving racemic 3-amino-5-methoxychroman and L(+)tartaric acid in water to form the tartrate salt; (ii) heating the solution until a clear solution is obtained; and (iii) crystallizing the tartrate salt by allowing the solution to cool to room temperature.

1 Claim, No Drawings

PROCESS FOR PREPARING (R)-3-AMINO-5-METHOXYCHROMAN

DESCRIPTION

This application is a divisional of application Ser. No. 08/144,671, filed on Oct. 28, 1993, now U.S. Pat. No. 5,470,151, which is a continuation-in-part of application Ser. Nos. 07/957,214, filed on Oct. 6, 1992 (abandoned), and Ser. No. 07/780,531, filed on Oct. 18, 1991 (abandoned). Ser. No. 07/957,214 is a continuation-in-part of Ser. No. 07/780,531, which is a continuation-in-part of aplication Ser. No. 07/633,247, filed Dec. 21, 1990 (abandoned).

FIELD OF THE INVENTION

The present invention relates to new substituted-3-aminochromans and thiochromans, enantiomers and salts thereof, processes for their preparation, pharmaceutical compositions containing said therapeutically active compounds as well as new intermediates useful in the preparation of the therapeutically active compounds and to the use of said active compounds in therapy.

An object of the invention is to provide compounds for therapeutic use, especially compounds having a therapeutic activity via the central nervous system (CNS). A further object is to provide compounds having a selective effect on the 5-hydroxy-tryptamine receptors in mammals including man.

It is also an object of the invention to provide a compound with a therapeutic effect after oral administration.

PRIOR ART

Therapeutically useful 3-amino-dihydro-[1]-benzopyran and benzothiopyran having effect on 5-hydroxytryptamine-responsive neurons in mammals are disclosed in EP 0222 996 and U.S. Pat. No. 4,801,605.

These compounds are defined by the formula

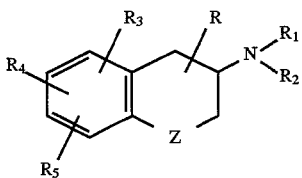

wherein

Z is 0 or S;

R is hydrogen or lower alkyl;

$R_1$ is hydrogen, lower alkyl or aryl-lower alkyl;

$R_2$ is hydrogen, lower alkyl or aryl-lower alkyl; or $R_1$ and $R_2$ together form a ring with 4–6 carbon atoms;

$R_3$ is hydrogen, hydroxy, lower alkoxy, aryl- lower-alkoxy, acyloxy or aryloxy when Z is S and $R_3$ is hydroxy, lower alkoxy, aryl-lower alkoxy, acyloxy or aryloxy when Z is O and $R_3$ is in 5- or 8-position when Z is O;

$R_4$ and $R_5$ are independently hydrogen, lower alkyl or halogen, and mono- or di-S-oxide thereof when Z is S, and pharmaceutically acceptable salts thereof.

3-Chromanamine hydrochlorides with two alkyl groups in the aromatic ring having central stimulating activities are described in J. Med. Chem. 15, p. 863–65 (1972).

Substituted-3-aminochromans intended for therapeutic use in the central nervous system are disclosed in patent documents, inter alia, EP 0 222 996 and WO 91/09853.

BACKGROUND OF THE INVENTION

Various central nervous system disorders such as depression, anxiety, etc. appear to involve the disturbance of the neurotransmitters noradrenaline (NA) and 5-hydroxytryptamine (5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occuring in depressed patients. The invention concerns compounds which have an effect on 5-HT neurotransmission.

Serotonin, or 5-HT, activity is thought to be involved in many different types of psychiatric disorders. For instance, it is thought that an increase in 5-HT activity is associated with anxiety, while a decrease in 5-HT release has been associated with depression. Serotonin has in addition been implicated in such diverse conditions as eating disorders, cardiovascular regulation and sexual behavior.

The 5-HT Receptors

The various effects of serotonin may be related to the fact that serotonergic neurons stimulate the secretion of severeal other hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date, these receptors have been classified as $5-HT_1$, $5-HT_2$, $5-HT_3$, and $5-HT_4$. The $5-HT_1$ receptor is further subdivided into the $5-HT_{IA}$, $5-HT_{IB}$, $5-HT_{IC}$ and $5-HT_{ID}$ subtypes. Each receptor subtype is involved in a different serotonin function and has different properties.

5-HT-Receptor-Active Agents

The mechanism of action for the drugs generally used today in the therapy of mental depression is indirect, i.e. they act by blocking the re-uptake of the neurotransmitters (NA and/or 5-HT) released from nerve terminals in the central nervous system. These drugs increase the concentration of the neurotransmitters in the synaptic cleft and hence restore adequate neurotransmission.

A fundamentally different way of improving the neurotransmission in the central nervous system in 5-HT neurons would be to use a direct 5-HT-receptor-active agent. In order to minimize side effects, or to effect a specific type of behavior or serotonin function, a high selectivity for a specific 5-HT receptor subtype would be preferred. Agonists can be used to activate specific receptors.

The object of the present invention is to provide compounds for therapeutic use, especially for treatment of 5-hydroxytryptamine mediated disorders in the central nervous system, for instance, depression, anxiety, obsessive-compulsive disorder (OCD), anorexia, senile dementia, migraine, stroke, Alzheimer's disease, hypertension, thermoregulatory and sexual disturbances, pain and for treatment of disturbances in the cardiovascular system.

DISCLOSURE OF THE INVENTION

The object of the present invention is to obtain new compounds which have a high affinity to the 5-hydroxytryptamine receptors in the central nervous system at the same time as they act as agonists, partial agonists or antagonists on the serotonin receptors. Thus, a group of new compounds of the formula I of the present invention as well as the enantiomers and salts thereof are useful in therapeutic treatment of 5-hydroxytryptamine mediated states and disorders such as depression, anxiety, anorexia, senile dementia, Alzheimer's disease, migraine, thermoregulator and sexual disturbances. Further aspects of the invention are related to the use of the compounds, enantiomers and salts thereof in pain control and in modulation of the cardiovascular system.

The invention provides compounds of the formula

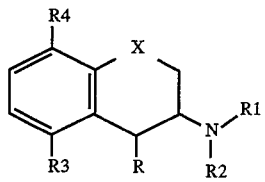

wherein

X is O or S;

p is an integer 0, 1 or 2;

R is hydrogen, fluoro or $C_1$–$C_6$ alkyl;

$R_1$ is hydrogen, $C_1$–$C_6$ alkyl or $C_2$–$C_6$ alkenyl;

$R_2$ is hydrogen, $C_1$–$C_6$ alkyl, $C_2$–$C_6$ alkenyl, $C_1$–$C_4$ alkylaryl where aryl may contain 1 or 2 heteroatoms selected from N, O or S optionally substituted by halogen, CN, $CF_3$, $C_1$–$C_6$ alkyl, $C_2$–$C_6$ alkenyl or $C_1$–$C_4$ alkoxy;

$R_1$ and $R_2$ may together form a 5- or 6- membered ring which may contain 1 or 2 heteroatoms selected from N, O or S;

$R_3$ is halogen, CN, $CF_3$, $SO_3CF_3$, $N_3$, $NO_2$, $C_1$–$C_6$ alkyl, $C_2$–$C_6$ alkenyl, $NH_2$, $NR_5R_6$, $COR_7$, 5- or 6-membered aryl which may contain 1 or 2 heteroatoms selected from N, O or S and being either (i) optionally substituted by one or more substituents independently selected from halogen, CN, $CF_3$, $C_1$–$C_6$ alkyl, $C_2$–$C_6$ alkenyl or $C_1$–$C_4$ alkoxy or either (ii) fused at two adjacent carbon atoms to an aryl ring, said aryl ring being optionally substituted by one or more substituents independently selected from halogen, CN, $CF_3$, $C_1$–$C_6$ alkyl, $C_2$–$C_6$ alkenyl or $C_1$–$C_4$ alkoxy;

$R_4$ is hydrogen or halogen;

$R_5$ is hydrogen, $C_1$–$C_6$ alkyl or $C_2$–$C_6$ alkenyl;

$R_6$ is $C_1$–$C_6$ alkyl or $C_2$–$C_6$ alkenyl; or $R_5$ and $R_6$ may together form a 5- or 6-membered ring which may contain 1 or 2 heteroatoms selected from N, O or S;

$R_7$ is hydrogen, hydroxy, chloro, bromo, $C_1$–$C_6$ alkyl, $C_2$–$C_6$ alkenyl, $C_1$–$C_4$ alkoxy; $NR_8$ $R_9$ or 5- or 6-membered aryl which may contain 1 or 2 heteroatoms selected from N, O or S optionally substituted by one or more of halogen, CN, $CF_3$, $C_1$–$C_6$ alkyl, $C_2$–$C_6$ alkenyl or $C_1$–$C_4$ alkoxy;

$R_8$ and $R_9$ are each independently hydrogen, $C_1$–$C_6$ alkyl, $C_2$–$C_6$ alkenyl, 5- or 6-membered aryl which may contain 1 or 2 heteroatoms selected from N, O or S optionally substituted by halogen, CN, $CF_3$, $C_1$–$C_6$ alkyl, $C_2$–$C_6$ alkenyl, $C_1$–$C_4$ alkoxy, or may together form a 5- or 6-membered ring containing 1 or 2 heteroatoms selected from N, O or S;

enantiomers or salts thereof.

In a preferred embodiment a further aspect of the invention is a pharmaceutical preparation containing as active ingredient a compound according to the formula

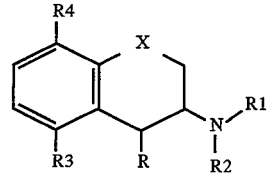

wherein

X is O;

R is hydrogen or $C_1$–$C_6$ alkyl;

$R_1$ is hydrogen, $C_1$–$C_6$ alkyl or $C_2$–$C_6$ alkenyl;

$R_2$ is $C_1$–$C_6$ alkyl, $C_2$–$C_6$ alkenyl, $C_1$–$C_4$ alkylaryl where aryl may contain 1 or 2 heteroatoms selected from N, O or S optionally substituted by halogen, CN, $CF_3$, $C_1$–$C_6$ alkyl, $C_2$–$C_6$ alkenyl or $C_1$–$C_4$ alkoxy; or $R_3$ is $C_2$–$C_6$ alkenyl, $COR_7$, 5- or 6-membered aryl which may contain 1 or 2 heteroatoms selected from N, O or S and being either (i) optionally substituted by one or more substituents independently selected from halogen, CN, $CF_3$, $C_1$–$C_6$ alkyl, $C_2$–$C_6$ alkenyl or $C_1$–$C_4$ alkoxy or either (ii) fused at two adjacent carbon atoms to an aryl ring, said aryl ring being optionally substituted by one or more substituents independently selected from halogen, CN, $CF_3$, $C_1$–$C_6$ alkyl, $C_2$–$C_6$ alkenyl or $C_1$–$C_4$ alkoxy;

$R_4$ is hydrogen or fluorine;

$R_7$ is $C_1$–$C_6$ alkyl, $C_2$–$C_6$ alkenyl, $C_1$–$C_4$ alkoxy, $NR_8$ $R_9$ or 5- or 6- membered aryl which may contain 1 or 2 heteroatoms selected from N, O or S optionally substituted by one or more of halogen, CN, $CF_3$, $C_1$–$C_6$ alkyl, $C_2$–$C_6$ alkenyl or $C_1$–$C_4$ alkoxy;

$R_8$ is hydrogen; and $R_9$ is hydrogen, $C_1$–$C_6$ alkyl, $C_2$–$C_6$ alkenyl, 5- or 6- membered aryl which may contain 1 or 2 heteroatoms selected from N, O or S optionally substituted by halogen, CN, $CF_3$, $C_1$–$C_6$ alkyl, $C_2$–$C_6$ alkenyl, $C_1$–$C_4$ alkoxy or may together form a 5- or 6-membered ring containing 1 or 2 heteroatoms selected from N, O or S;

an enantiomer or a pharmaceutically acceptable salt thereof.

A preferred group of therapeutically active compounds of formula I are those wherein $R_1$ is hydrogen, n-propyl, or i-propyl; and $R_2$ independently of $R_1$ is n-propyl or i-propyl. It has been found that in compounds where $R_1$ and $R_2$ are not the same and one is i-propyl and the other is n-propyl, that it is the R-enantiomer that has the highest affinity for the 5-$HT_{IA}$ receptor and thus, the R-enantiomer of such compounds is preferred.

R is preferably hydrogen or methyl. If R is methyl it is preferably in the cis configuration.

It is also preferred that $R_3$ is a carbonyl group $COR_7$. Among these groups are the definition of $R_7$ is alkyl, aminoalkyl e.g. methyl, ethyl, n-propel, i-propyl, cyclopropyl, n-butyl, i-butyl, t-butyl and cyclobutyl or aryl, aminoaryl e.g. phenyl, thienyl, fluorophenyl and furanyl. Another preferred group is when $R_3$ is aryl e.g. phenyl, thienyl, furanyl, or fluorophenyl. Another preferred group is when $R_3$ is alkenyl e.g., i-propenyl and allyl.

Another preferred group of active compounds are those wherein $R_4$ is fluorine in the 8-position as well as enantiomers thereof.

Certain embodiments of the invention concern: (R)-3-(N-isopropyl-N-propylamino)-5-N-isopropylcarbamoylchroman; (R)-3-(N-isopropyl-N-propylamino)-5-carbamoylchroman; (R)-8-fluoro-3-(N-isopropyl-N-propylamino)5-carbamoylchroman; (R)-8-fluoro-3-[N-(1-ethyl)propyl-N-n-propylamino]-5-carbamoylchroman; (R)-8-fluoro-3-(N-isopropyl, N-n-propylamino)-4-cis-methyl-5-carbamoylchroman; (R)-8-fluoro-3-(N-cyclopentyl, N-n-propylamino)-5-N-methylcarbamoylchroman; (R)-8-fluoro-3-(N-t-butyl, N-n-propylamino)-5-carbamoylchroman; (R)-8-fluoro-3-(N-neopentyl-N-n-propylamino)-5-N-methylcarbamoylchroman; and (R)-8-fluoro-3-(N-isopropyl-N-n-propylamino)-5-N-ethylcarbamoylchroman.

Compounds of formula I wherein $R_3$ is CN, COOH, COCl, COBr, $N_3$, or $SO_3CF_3$ are new intermediates for preparation of the therapeutically active compounds of formula I.

Definitions $C_1$–$C_6$ alkyl in formula I representing straight, branched and cyclic alkyl groups having 1 to 6 carbon atoms, for example methyl, ethyl, n-propyl, i-propyl, n-butyl, i-butyl, t-butyl, n-pentyl, i-pentyl, t-pentyl, neo-pentyl, n-hexyl, i-hexyl, cyclopropyl, cyclobutyl, cyclopentyl, cyclohexyl, methylcyclopropyl, ethylcyclopropyl, methylcyclobutyl. Preferred alkyl groups have 1 to 4 carbon atoms.

$C_2$–$C_6$ alkenyl in formula I representing straight or branched carbon atoms chains having 2 to 6 carbon atoms and containing one or two double bond, for example allyl, propenyl, isopropenyl, butenyl, isobutenyl, pentenyl, isopentenyl. Preferred alkenyl groups have 2 to 4 carbon atoms and one double bond.

$C_1$–$C_4$ alkoxy in formula I representing a straight alkoxy group having 1 to 4 carbon atoms, for example methoxy, ethoxy, propoxy or butoxy, preferably methoxy and ethoxy.

$C_1$–$C_4$ alkylaryl where aryl may contain 1 or 2 heteroatoms selected from N, O or S in the definition of $R_2$ in formula I representing an aryl residue having 3 to 12 carbon atoms in the aromatic ring and optionally 1 or 2 heteroatoms selected from N, O or S in the aromatic ring, bond by a straight or branched alkylen chain having 1 to 4 carbon atoms in the aliphatic chain. The aromatic ring may be substituted by one or more of nitrile, trifluoromethyl, halogen such as fluoro, chloro, bromo, iodo, $C_1$–$C_6$ alkyl, e.g. methyl, ethyl, propyl, $C_2$–$C_6$ alkenyl e.g. alkyl, propenyl, or $C_1$–$C_4$ alkoxy preferably in meta and/or para position. Examples of suitable aryl groups in $C_1$–$C_4$ alkylaryl are phenyl, naphtyl, biphenyl, thienyl, furyl, pyryl, pyrimidyl and pyrridinyl. Preferred $C_1$–$C_4$ alkylaryl groups are unsubstituted and substituted phenylalkyl groups wherein the alkyl group is a straight or branched alkyl having 1 to 4 carbon atoms and the aromatic ring may be substituted by one or more of fluoro, chloro, bromo, iodo, nitrile, trifluoromethyl, methyl or ethyl in meta and/or para position. For example benzyl, phenethyl and phenylpropyl, especially preferred is phenylpropyl.

Halogen as used herein represents fluoro, chloro, bromo, iodo, preferably fluoro.

5- or 6-membered aryl which may contain 1 or 2 heteroatoms selected from N, O or S and being either (i) optionally substituted by one or more substituents independently selected from halogen, CN, $CF_3$, $C_1$–$C_6$ alkyl, $C_2$–$C_6$ alkenyl or $C_1$–$C_4$ alkoxy or either (ii) fused at two adjacent carbon atoms to an aryl ring, said aryl ring being optionally substituted by one or more substituents independently selected from halogen, CN, $CF_3$, $C_1$–$C_6$ alkyl, $C_2$–$C_6$ alkenyl or $C_1$–$C_4$ alkoxy; in the definition of $R_3$ in formula I representing either (i) substituted or unsubstituted phenyl, thienyl, furyl, pyridyl, pyrimidyl, pyrazinyl, pyradazinyl, thiozolyl, isothiozolyl, oxazolyl, isoxazolyl, imidazolyl, pyrazolyl, piperazinyl or morpholinyl or either (ii) substituted or unsubstituted quinolyl, isoquinolyl, quinazolyl, quinaxazolyl or indolyl.

5- or 6-membered aryl which may contain 1 or 2 heteroatoms selected from N, O or S in the definition of $R_7$, $R_8$ and $R_9$ in formula I representing phenyl, thienyl, furyl, pyridyl, pyrimidyl, pyrazinyl, pyridazinyl, thiazolyl, isothiazolyl, oxazolyl, isoxazolyl, imidazolyl, pyrazolyl, piperazinyl, morpholinyl.

Examples of suitable 5- or 6-membered ring structures formed by $R_1$ and $R_2$ or $R_5$ and $R_6$, or $R_8$ and $R_9$ respectively and the nitrogen atom and which may contain a further heteroatom selected from N, O or S are piperazine, morpholine, pyrrolidine, pyrrole, pyrroline, imidazole, imidazoline, imidazolidine, pyrazole, pyridine, pyrazine, pyrimidine, pyridazine.

The compounds of the invention have one or two assymetric carbon atoms. When R is hydrogen the compounds have an assymetric carbon atom adjacent to the nitrogen atom i.e. $C_3$ and when R is $C_1$–$C_6$ alkyl the compounds have an assymetric carbon atom adjacent to the nitrogen atom and an assymetric carbon atom adjacent to the alkyl group i.e. $C_4$. Thus, the compounds exist as two or four optical isomers, i.e. enantiomers. Both the pure enantiomers, racemic mixtures are within the scope of the present invention. The therapeutic properties of the compounds may to a greater or lesser degree be ascribed to the racemate or to the enantiomers occurring.

Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, pamoic, ethanedisulfonic, sulfamic, succinic, methylsulphonic, propionic, glycollic, malic, gluconic, pyruvic, phenylacetic, 4-aminobenzoic, anthranilic, salicylic, 4-aminosalicylic, 4-hydroxybenzoic, nicotinic, methanesulfonic, ethanesulfonic, hydroxyethanesulfonic, benzenesulfonic, p-toluenesulfonic, sulfanilic, naphtalenesulfonic, ascorbinic, cyclohexylsulfamic, fumaric, maleic and benzoic acids. These salts are readily prepared by methods known in the art.

Methods of Preparation

The compounds of the formula I may be prepared by the following processes constituting a further aspect of the invention.

a. Converting a compound of formula II

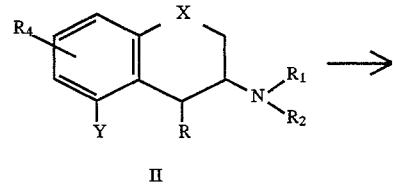

II

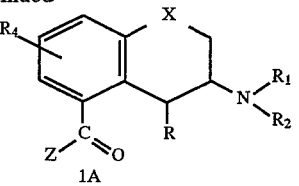

wherein Y is a leaving group such as trifluoromethane sulfonate ($OSO_2CF_3$), halide e.g. Cl or Br, and X, R, $R_1$, $R_2$ and $R_4$ are defined as above by substitution of the group Y to a carboxy group COZ, wherein Z is Cl, Br, OH, $OR_p$ where $R_p$ is $C_1$–$C_6$ alkyl to formation of a compound of formula I wherein $R_3$ is COZ, (IA).

The compound of formula II can be converted to the compound of formula IA by the following catalytic cycle. Metal $M^o$ should be a zerovalent transition metal, such as Pd or Ni with ability to undergo oxidative addition to aryl-Y-bonds e.g. the aryl-$SO_3CF_3$ bonds. $M^o$ may be generated in situ from $M^{II}$. The aryl-CO-$M^{II}$-Y are formed by treatment with carbon monoxide (CO).

e.g., triethylamine in an inert organic solvent preferentially a polar aprotic solvent such as dimethylformamide (DMF), dimethylsulfoxide (DMSO), aceton, acetonitrile etc. The reaction is normally performed at a temperature between +40° to +120° C. and at a pressure between 100 to 500 KPa. Optionally followed by hydrolyze and treatment with a thionyl halide e.g., thionylchloride to obtain the corresponding acid halide derivative.

b. Compound of formula I wherein $R_3$ is COZ (IA) can also be formed by the reversed process:

A reaction as the catalytic cycle using a zerovalent transition metal $M^o$, such as Pd, or Ni with ability to undergo an oxidation addition to Z-Y, wherein Z is defined Cl, Br, OH or $OR_p$ where $R_p$ is $C_1$–$C_6$ alkyl and Y is a leaving group such as $SO_3CF_3$ and halide, treatment with carbon monoxide followed by addition of a compound of formula III, wherein X, R, $R_1$, $R_2$ and $R_4$ are as defined under formula I.

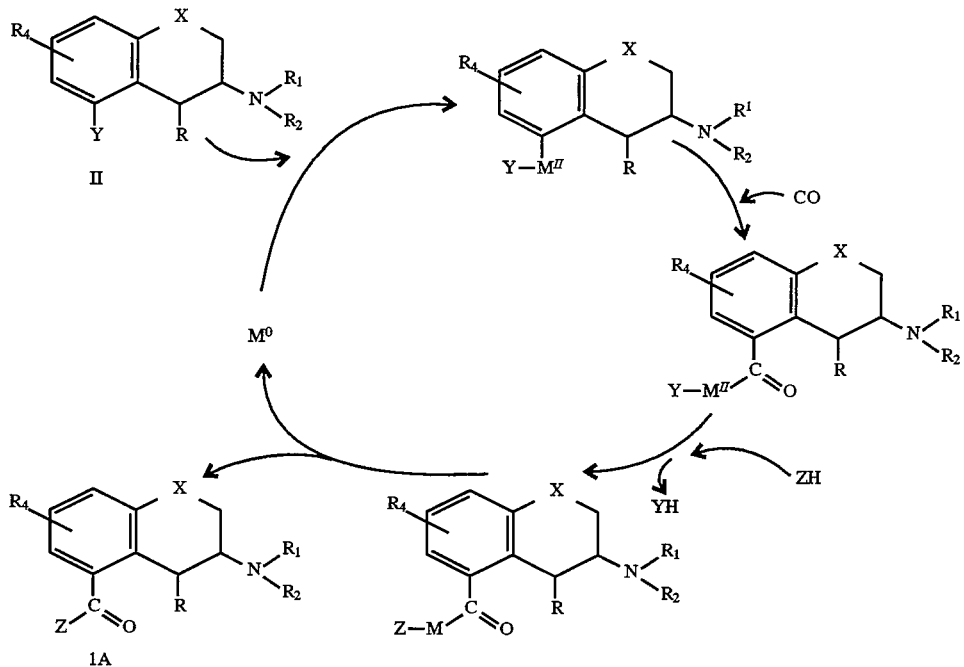

Further reagants are an alcohol such as alkanol e.g., methanol, ethanol, an amine base such as a trialkylamine

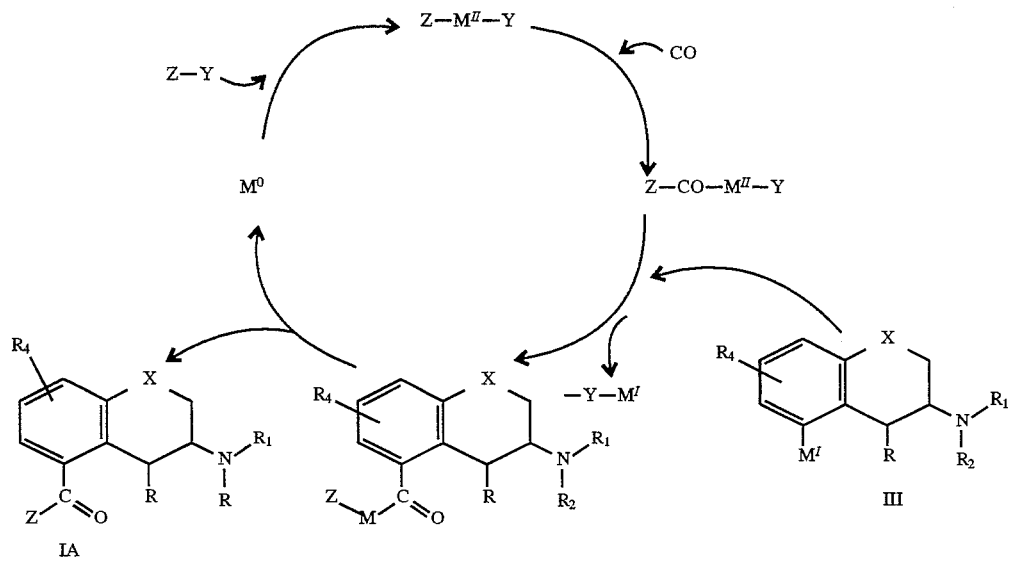

The Z-CO-$M^{II}$-Y can also be formed from Z-COCl directly. The reaction conditions and reagant are the same as described in method a. above. Hydrolyze of suitable carboxylic acid ester forms the free acid, which can be converted to its acid halide derivative.

c. Converting a compound of formula II

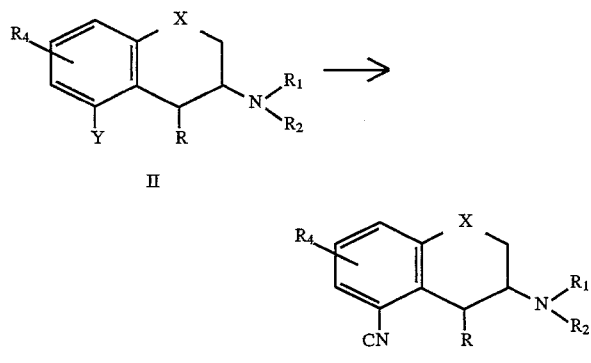

wherein X, R, $R_1$, $R_2$ and $R_4$ are as defined above and Y is a leaving group such as Cl, Br or $SO_3CF_3$ by treatment with a cyanide reagant such as cupper cyanide (CuCN) to obtain a compound of formula I wherein $R_3$ is CN. The reaction with cyanide reagant is performed in an inert organic solvent such as dimethylformamide, hexamethylenphosphotriamide etc. at a temperature between 20° to 200° C. preferrably between 50° to 150° C. and at normal temperature.

d. Amination of a compound of formula IA

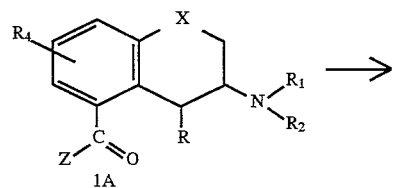

-continued

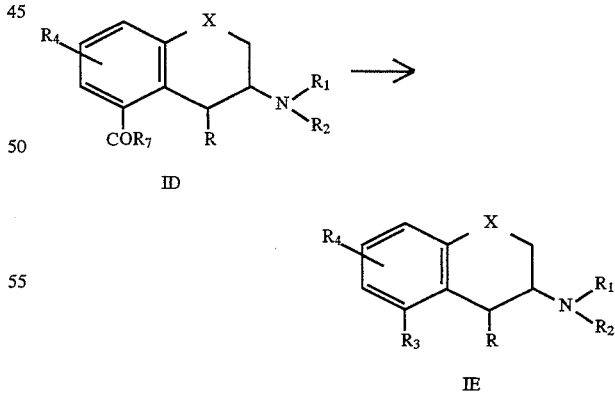

wherein X, R, $R_1$, $R_2$ and $R_4$ are as defined above and Z is Cl, Br, OH or $OR_p$ where $R_p$ is $C_1$–$C_6$ alkyl. If the compound of formula IA is a carboxylic acid ester it must first be hydrolyzed to form the free acid. The free acid is then transformed into the amide IC via its acid chloride derivative by reaction of the corresponding amine $NR_8R_9$, where $R_8$ and $R_9$ are as defined under formula I, in a nonpolar aprotic solvent e.g. toluene, benzen at reflux temperature between 0° to 100° C.

e. Wittig reaction to formation of a compound of formula I where $R_3$ is a $C_2$–$C_6$ alkenyl group (IE).

A 5-carboxy chroman/thiochroman derivative, where X, R, $R_1$, $R_2$ and $R_4$ are defined as above and $R_7$ is alkyl defined as above (ID) is converted by using a dipolar reagant such as alkyltriphenylphosphoniumhalide to formation of a corresponding alkenyl group (IE).

f. Catalytic hydrogenation of a 5-alkene chroman/thiochroman derivative of formula I wherein $R_3$ is a $C_2$–$C_6$ alkenyl group by using $H_2/Pd$, $H_2/Pt$ or $H_2/Raney\ Ni$ to formation of corresponding chroman/thiochroman derivative of formula I wherein $R_3$ is $C_1$–$C_6$ alkyl (IF).

g. Substitution of a 5-bromo-chroman/thiochroman derivative by treatment with an appropriate stannic trialkyl reagant in presence of a zerovalent metal preferrably palladium ($Pd^o$) to obtain a compound of formula I wherein $R_3$ is $C_1$–$C_6$ alkyl, $C_1$–$C_4$ alkenyl or aryl, in presence of carbonmonoxide (CO) is formed a compound of formula I wherein $R_3$ is $COR_7$ wherein $R_7$ is $C_1$–$C_6$ alkyl, $C_2$–$C_6$ alkylen or aryl.

The substitution may be performed by one of the following ways:

thiochroman derivative. Suitable $R_7Li$ used is alkyllithium e.g. $CH_3Li$, alkenyllithium e.g. $CH_2CHLi$ or aryllithium e.g. phenyl-Li. The reaction is performed in an inert organic solvent preferrably a nonpolar aprotic solvent such as ethers e.g. diethyl ether, tetrahydrofuran at a temperature between $-50°$–$+50°$ C.

i. Hydrolysis of a compound of formula I, wherein $R_3$ is CN (IB)

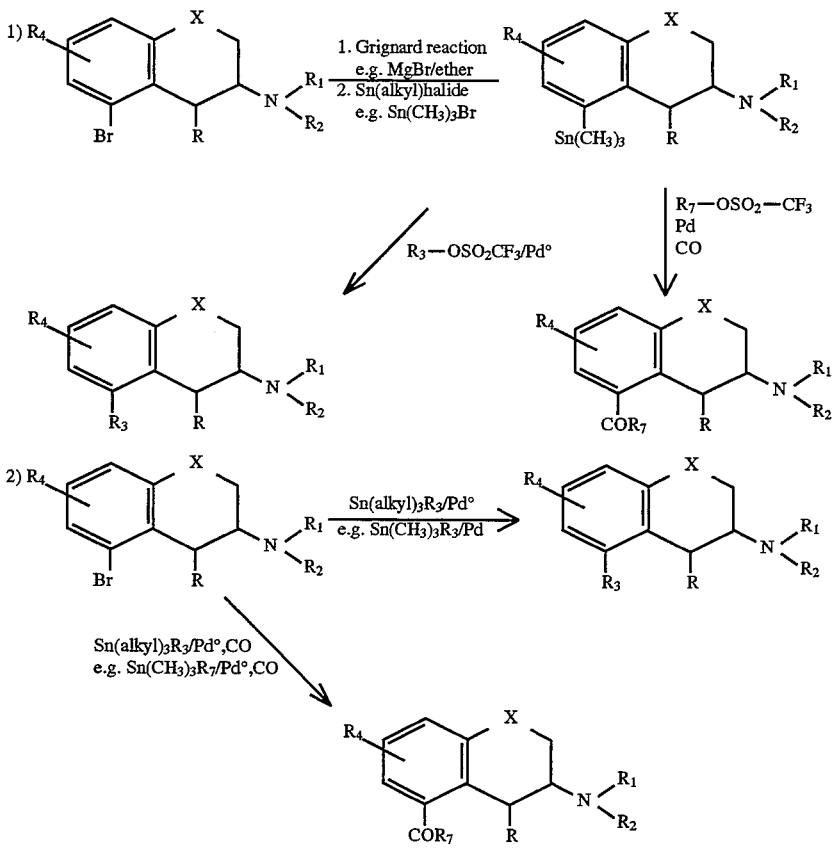

h. Converting the 5-carboxy chroman/thiochroman derivative of formula I

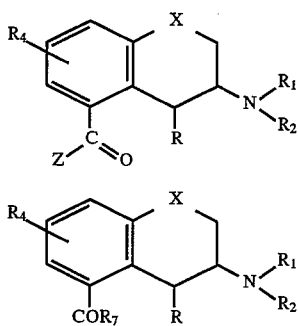

where X, R, $R_1$, $R_2$ and $R_4$ are defined as above and Z is Cl, Br by using $R_7Li$ wherein $R_7$ is alkyl, alkenyl or aryl as a cuprate reagant to obtain corresponding 5-ketochroman/

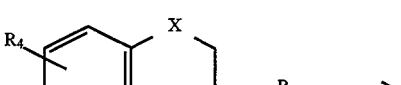

IB

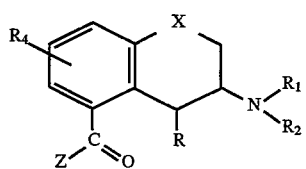

IA wherein X, R, $R_1$, $R_2$ and $R_4$ are as defined above optionally followed by treatment with a thionyl halide e.g. thionylchloride, thionylbromide to obtain a compound of formula I wherein $R_3$ is COZ where Z is OH, Cl or Br.

j. Substitution of a compound of formula I, wherein $R_3$ is CN (IB)

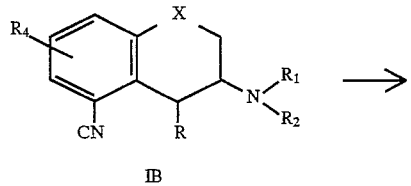

IB wherein X, R, $R_1$, $R_2$ and $R_4$ are defined as above by treat-ment with an appropriate organometallic reagant preferentially an organolithium such as $R_7$Li or a Gringard reagent such as $R_7$Mg halide in an inert organic solvent preferentially a nonpolar aprotic solvent such as bensen, ethers e.g. diethylether, tetrahydrofuran followed by hydrolysis of the intermediate complex to obtain a compound of formula I wherein $R_3$ is $COR_7$ where $R_7$ is $C_1$–$C_6$ alkyl, $C_2$–$C_6$ alkenyl or aryl.

k. Hydrogeneration of a 5-alkene thiochroman/chroman derivative of formula I wherein $R_3$ is a $C_2$–$C_6$ alkenyl group by using $H_2$/Pd, $H_2$/Pt or $H_2$/Raney Ni or potassium azodicarboxylate to formation of corresponding thiochroman/chroman derivative of formula I wherein $R_3$ is $C_1$–$C_6$ alkyl.

l. Converting a compound of the formula (II)

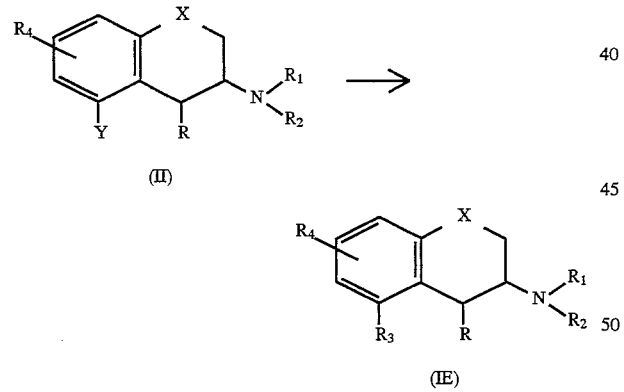

wherein Y is a leaving group such as trifluoromethanesulphonate (Tf), phosphonate, halide such as Br or J and R, $R_1$ and $R_2$ are defined as above by substitution of the group Y to $R_3$ where $R_3$ is a $C_2$–$C_6$ alkenyl group (IE).

The compound (II) may be converted to (IE) by reaction with a transition metal, such as Pd or Ni with ability to form ligand complex and undergo oxidative addition. A suitable alkenyl-substituent can be introduced via a suitable trialkylalkenylstannane.

Further reagents are an amine such as triethylamine and lithiumsalt e.g. lithium chloride. The reaction is s preferentially carried out in a polar aprotic solvent such as dimethylformamide, dioxane, acetonintril or dimethylsulfoxide at a temperature between +40° to +120° C.

m. Converting a compound of the formula (II)

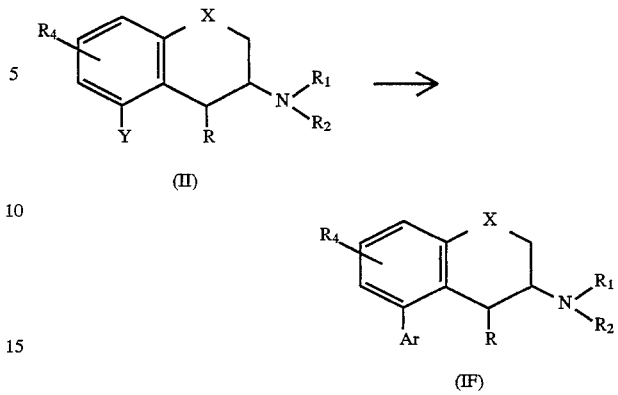

wherein Y is a leaving group such as trifluoromethanesulphonate (Tf), phosphonate, halide such as Br or J and R, $R_1$ and $R_2$ are defined as above by substitution of the group Y to 5- or 6-membered aryl (Ar) which may contain 1 or 2 heteroatoms selected from N, O, or S being either substituted or fused at two adjacent carbon atoms to an aryl ring as defined above to formation of a compound of formula IF.

The compound (II) may be converted to (IF) by reaction with a transition metal, such as Pd or Ni with ability to form ligand complex and undergo oxidative addition. A suitable aryl-substituent can be introduced via a suitable trialkylarylstannane or aryl-boric acid reagents.

Further reagents are an amine such as triethylamine and lithiumsalt e.g. lithium chloride. The reaction is preferentially carried out in a polar aprotic solvent such as dimethylformamide, dioxane, acetonitril or dimethylsulfoxide at a temperature between +40° to +120° C.

The following method describes one way of obtaining the intermediate of formula IB

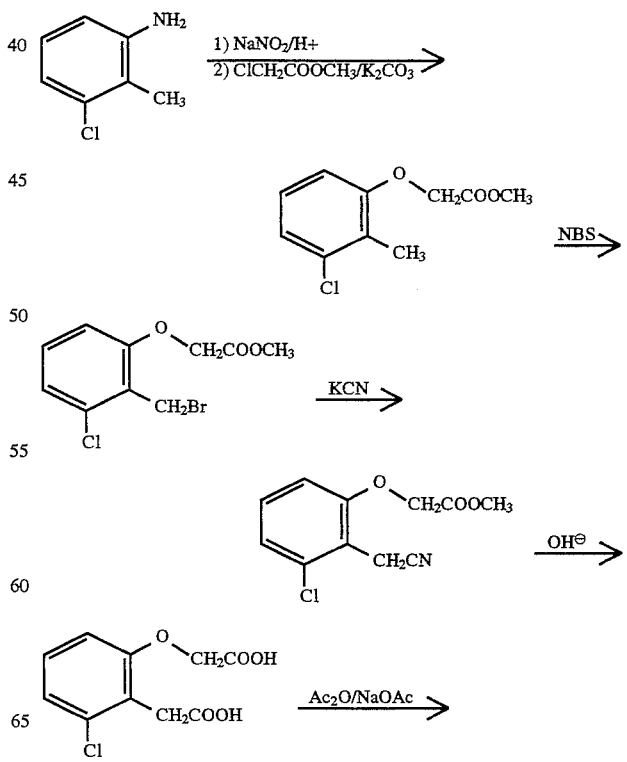

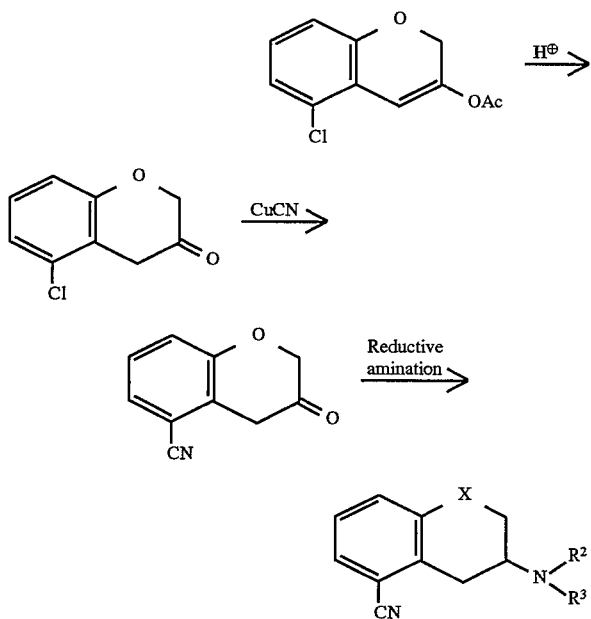

wherein $R_1$, $R^2$ and $R^4$ are defined as in formula I

Pharmaceutical Preparations

According to the present invention the compounds of the formula I will normally be administered orally, rectally or by injection, in the form of pharmaceutical preparations comprising the active ingredient either as a free base or a pharmaceutically acceptable non-toxic acid addition salt, e.g. the hydrochloride, hydrobromide, lactate, acetate, phosphate, sulphate, sulphamate, citrate, tartrate, oxalate and the like in a pharmaceutically acceptable dosage form. The dosage form may be a solid, semisolid or liquid preparation and may include suitable excipients, diluents and carriers. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing a compound of the formula I in the form of dosage units for oral application, the selected compound may be mixed with a solid excipient or carrier, e.g. lactose, saccharose, sorbitol, mannitol, starches such as potato starch, corn starch or amylopectin, cellulose derivatives, a binder such as gelatine or poly-vinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the table can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or poly-ethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being diluents and carriers such as sugar and mixture of ethanol, water, glycerol and propylene glycol. Optionally such liquid preparations may contain colouring agents, flavouring agents, saccharine and carboxymethyl-cellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutical treatment of humans are about 0.01–100 mg/kg bodyweight at peroral administration and 0.001–100 mg/kg bodyweight at parenteral administration.

Pharmacology

Pharmacological Treatment of Depression in Man

Evidence is available that in depressed patients the neurotransmission in the central nervous system (CNS) may be disturbed. These disturbances appear to involve the neurotransmitters noradrenaline (NA) and 5-hydroxytryptamine (5-HT). The drugs most frequently used in the treatment of depression are considered to act by improving the neurotransmission of either or both of these physiological agonists. Available data suggest that the enhancement of 5-HT neurotransmission will primarily improve the depressed mood and anxiety, whereas the enhancement of noradrenaline neurotransmission will rather improve the retardation symptoms occurring in depressed patients. In recent years many efforts have been made to develop new drugs with high selectivity for the improvement of the 5-HT neurotransmission in the CNS.

The dominating mechanism of action for the drugs generally used today in the therapy of mental depression is indirect, i.e. they act by blocking the reuptake of the neurotransmitters (NA and/or 5-HT) released from nerve terminals in the CNS, thus, increasing the concentration of these transmitters in the synaptic cleft and hence restoring an adequate neurotransmission.

A fundamentally different way to improve the neurotransmission in the central 5-HT-neurons would be to use a direct 5-HT-receptor agonist. In order to minimize side effects, a high selectivity for this kind of receptors would then be preferable.

Selective antagonism of the inhibitory autoreceptors located on the cellbodies of 5-HT-neurons would be another fundamentally different way to improve the 5-HT neurotransmission.

Surprisingly, we have found that a group of compounds of the formula I have selective, direct stimulating or inhibitory effect on a subgroup of central 5-HT receptors. Another observation is that some of those compounds have a particularly good oral bioavailability. In order to evaluate the selectivity for the subpopulation of 5-HT receptors, the affinity for various receptors in rat brain were measured in vitro using receptor assays (Ki nM).

In general the compounds of formula I wherein $R_4$ is a hydrogen are agonists with respect to activity on the 5-$HT_{IA}$ receptor. Additionally we have found that the racemate and surprisingly the (R)-enantiomer of the compound 3-(N-isopropyl-N-propylamino)-5-N-isopropylcarbamoylchroman has shown high affinity and stereoselective direct stimulatory effect on the 5-$HT_{IA}$ receptors in CNS combined with a good bioavailability. Surprisingly, we also have found that when a fluoro substituent replaces the hydrogen in the 8-position of the ring structure of formula I it seems that the pharmacological profile of the fluoro substituted compound is different from the similar compound wherein there is hydrogen in the 8-position. The introduction of a fluoro substitutent in the 8-position shifts the pharmacological profile from an agonist towards partial agonist or antagonist for the same subreceptor 5-$HT_{IA}$. (R)-8-fluoro-3-(N-isopropyl-N-propylamino)-5-carbamoylchroman is an example of a stereoselective 5-$HT_{IA}$ receptor antagonist.

In Vitro Test: Receptor Binding Assay 5-$HT_{IA}$ binding assay. Cerebral cortex+hippocampus from each rat was dissected and homogenized in 15 ml ice-cold 50 mM Tris-HCl buffer, 4.0 mM $CaCl_2$ and 5.7 mM ascorbic acid, pH 7.5 with an Ultra-Turrax (Janke & Kunkel, Staufen, FRG) for ten s. After centrifugation for 12.5 min at 17,000 rpm (39,800×g in a Beckman centrifuge with a chilled JA-17 rotor (Beckman, Palo Alto, Calif., USA), the pellets were resuspended in the same buffer and homogenization and centrifugation repeated. To each pellet 5 ml ice-cold 0.32M sucrose was added and homogenized for 5 sec. These samples were kept frozen at −70° C. When used they were diluted with the buffer to 8 mg tissue/ml and homogenized for 10 sec. The tissue homogenates were incubated for ten minutes at 37° C. and then supplied with 10 µM pargyline followed by reincubation for 10 minutes.

The binding assay followed that described by Peroutka, J. Neurochem. 47, 529–540, (1986). The incubation mixture (2 ml) contained $^3$H-8-OH-DPAT (0.25 to 8 nM), 5 mg/ml tissue homogenate in 50 mM Tris-HCl buffer containing 4.0 mM $CaCl_2$ and 5.7 mM ascorbic acid, pH 7.5. Six different concentrations of $^3$H-8-OH-DPAT were analyzed. Binding experiments were started by the addition of tissue homogenate and followed by incubation at 37° C. for 10 minutes. The incubation mixtures were filtered through Whatman GF/B glass filters with Brandel Cell Harvester (Gaithersburg, Md., USA). The filters were washed twice with 5 ml ice-cold 50mM Tris-HCl buffer, pH 7.5, and counted with 5 ml Ready-solv HP (Beckman) in a Beckman LS 3801 scintillation counter. Non-specific binding was measured by the addition of 10 µM 5-HT to the reaction mixture. The binding data was processed by non-linear least squares computer analysis (Munson and Rodbard, Anal. Biochem. 107, 220–239, (1980).

The test results are expressed as $K_i$ and are given in nM. For instance, 3-dipropylamino-5-acetylchroman has $K_i$ 1.0 (nM), 3-dipropylamino-5-carbamoylchroman has $K_i$ 3.1 (nM), 3-dipropylamino-5-N-methylcarbamoylchroman has $K_i$ 3.3 (nM), 3-dipropylamino-5-(2-thienylcarbonylchroman has $K_i$ 1.7 (nM) and (R)-8-fluoro-3-(N-isopropyl-N-propylamino)-5-carbamoylchroman has $K_i$ 5.4 (nM).

Test of Antagonists

Administration of 5-$HT_{IA}$ agonist to rats reduces 5HT synthesis and decreases the temperature of the rat. To test for an antagonist you first administer the test compound and determine if it has any of the effects of an agonist. Subsequently, a known agonist is administered to determine if the antagonist is capable of blocking the effect of the agonist and to what extent. A strong antagonist will block the effects of the agonist. A compound can function both as a partial agonist and have some antagonist effect by blocking the binding of another stronger known agonist, for example 8-OHDPAT, to the 5-$HT_{IA}$ receptor. The same receptor binding assays and bioavailability assays are used as in the test for agonist.

Test of Antagonists or Partial Agonists

Administration of a 5-$HT_{IA}$ agonist to rats reduces 5HT synthesis rate and decreases the body temperature of the rat. Screening test for an antagonist or a partial agonist are performed by initial administration of the test compound and determine if it has any of the effects of an agonist.

Subsequently, a known 5-$HT_{IA}$ agonist (reference 8-OH-DPAT) is administered to determine if the test compound is capable of blocking the effects of the known agonist and to what extent. An antagonist will block all effects of the agonist. A compound can function both as a weak agonist and also have some antagonist effect shown by blocking the effects of the "reference" agonist to a certain extent. Such a compound is called an partial agonist.

The same receptor binding assays and bioavailability assays are used for 5-$HT_{IA}$ agonists as well as for antagonists and partial agonists.

In Vivo Test: Oral Bioavailability in Dogs

The bioavailability test was performed as described below and gives the mean value of 17% for the (R)-enantiomer and 21% for the racemate of compound 3-(N-isopropyl-N-n-propylamino)-5-(N-isopropyl)carbamoylchroman based on plasma level measurements in dogs. Dose-effect studies in rat following subcutaneous versus oral administration further support a high availability of the compound at the receptor after oral administration.

Method: Assessment for oral bioavailability (systemic availability) was based on the plasma area under the curve (AUC) method. An aqueous saline solution of compound of the invention was administered intravenously (i.v.) and orally (p.o.) to the animals and concentrations of the compound in plasma measured at numerous timepoints. The doses administered were 1 µmol.kg$^{-1}$ and 10 µmol.kg$^{-1}$ for intravenous and oral administration, respectively. AUC was calculated according to the trapezoidal rule. Determination of the test compound in plasma was accomplished by an HPLC method which incorporated electrochemical detection.

In Vivo Test: Synthesis of 5-HT

As predicted for a selective 5-$HT_{IA}$ agonist, the synthesis rate of 5-HT, measured as a significant decrease of the 5-HTP level in rat brain was recorded after 0.1 mg/kg following subcutaneous administrations as well as after 0.2 mg/kg oral administration of the (R)-enantiomer of compound 3-(N-isopropyl-N-n-propylamino)-5-(N-isopropyl) carbamoylchroman.

Method: The rate of synthesis of 5-HT in the rat streatum was measured as the accumulation of 5-HTP during 30 min after inhibition of aromatic L-amino acid decarboxylase by NSD 1015 (decarboxylase inhibitor, 100 mg/kg i.p.). The test compound was administered 30 min before the NSD 1015. The regions of the brain to be examined were dissected, frozen and stored.

The levels of 5-HTP (5-hydroxytryptophan) was determined by use of high performance liquid chromatography (HPLC) with electrochemical detection according to the method of Magnusson, Nilsson and Westerlund (1980). The mobile phase was 0.1M phosphate buffer (pH 2.5) :methanol:acetonitrile-89:9:2 v/v, containing 1 mM octylsulphate. The frozen samples were weighed and homogenized in 0.1M perchloric acid, containing 2.5 nM sodium bisulphite, 1 mM ethylene diamine tetraacetic acid (EDTA) and epinine as an internal standard. The supernatants were injected directly onto a Supelcosil $C_{18}$ (3 µM) column, connected to a detector (ESA Coulochem 5100A), set to 0.05/0.40 V.

Temperature Effects

A significant temperature decrease was obtained in rats following subcutaneous administration of 0.3 mg/kg or 1 mg/kg using oral administration of the (R)-enantiomer of compound 3-(N-isopropyl-N-n-propylamino)-5-(N-isopropyl)carbamoylchroman.

Method: In each test, thirty rats, weighing approx 250 g, housed in 6 cages of 5 rats, are used. The rats have free access to food and water. Before the start of testing, they are numbered and left undisturbed for at last 1 hour. Before the administration of the compound, the body temperature of each rat is measured using a YSI 2100 tele-thermometer. The thermometer probe is inserted 10 cm into the rectum and left in pace for thirty seconds.

The drug is then administered either subcutaneously or orally. In each experiment vehicle and 4 doses of drug are tested. One rat in each cage receives each treatment. The order of treatment is rotated since disturbance to the cage increases the activity of the rats, and thereby their body temperature. Thirty minutes after drug administration the rats' body temperature are measured again. The procedure is repeated 60, 90 and 120 minutes after drug administration. The resultant data on body temperature is subjected to analysis of variance. A significant group by time interaction is taken as an indication of drug effect. To obtain the minimum effective dose, the mean temperature for each of the drug treated groups are compared with that of the vehicle group at each time point using Dunnett's t-test with a level of significance of $p<0.02$. An indication of bioavailability may be obtained by calculating the ratio between the minimum effective doses following oral and subcutaneous administration.

WORKING EXAMPLES

The following examples will further illustrate the invention.

Example 1

3-Dipropylamino-5-trifluoromethanesulfonylchroman

3-Dipropylamino-5-hydroxychroman (Thorberg et al. Acta Pharm. Suec. 24(1987), the contents of which are hereby incorporated herein by reference) (1.4 g, 4.0 mmol) and N,N-dimethylaminopyridine (0.1 g, 0.75 mmol) were dissolved in 50 mL methylene dichloride ($CH_2Cl_2$) and cooled to –30° C. 2,4,6-Collidine (0.75 mL, 5.7 mmol) was added followed by trifluoromethane sulfonic anhydride (1.0 mL, 6.0 mmol).

The solution was stirred at –20° C. for 3 hours and then allowed to reach ambient temperature. The solution was washed with aqueous $NaHCO_3$, dried with $Na_2SO_4$ and evaporated to dryness. The pale yellow oil was finally purified by flash chromatography (silica gel) by elution with ethyl acetate/hexane 1:9.

Yield: 55%, Mp 125°–127° C. (oxalate).

Example 2

3-Dipropylamino-5-methyloxycarbonylchroman

3-Dipropylamino-5-trifluoromethanesulfonylchroman (Example 1; 4.43 g, 11.6 mmol) was dissolved in 80 mL dimethylformamide/methanol 6:2 and the solution was degassed (10 mmHg, 20° C., 15 min). $PdOAc_2$ (76 mg, 0.34 mmol), 1,3-bis-diphenylphosphinopropane (141 mg, 0.34 mmol) and triethylamine (3.5 mL, 25 mmol) were then added. The mixture was heated to 70° C. under CO atmosphere and stirred for 5 hours. The solution was cooled, diluted with toluene (200 mL), washed with aqueous $NaHCO_3$, dried with $Na_2SO_4$ and evaporated to dryness. The oil was purified by flash chromatography (silica gel) by elution with ethyl acetate/hexane 1:8.

Yield: 76%, Mp 150°–152° C. (HCl-salt).

Example 3

3-Dipropylamino-5-carbamoylchroman

3-Dipropylamino-5-methyloxychroman (Example 2; 400 mg, 1.37 mmol) was dissolved in 10 ml methanol and NaOH (60 mg, 1.5 mmol) in 2 mL $H_2O$ was added. The mixture was refluxed for 5 hours, cooled, filtered through Celite and evaporated to dryness. The residue was refluxed in $SOCl_2$ (5 mL, 68 mmol) for 30 minutes. The excess $SOCl_2$ was then removed in vacuo to give 3-dipropylamino-5-chloroformylchroman-HCL as a gum. The pale brown gum was dissolved in $CH_2Cl_2$ (50 mL), and a stream of $NH_3$ (g) was introduced during 2 minutes. The solution was washed with aqueous $NaHCO_3$, dried with $Na_2SO_4$ and evaporated to dryness. The oil was purified by flash chromatography (silica gel) by elution with ethyl acetate/hexane 1:4.

Yield 80%, $^{13}$C-NMR: 172.0 154.9 136.5 126.9 120.4 119.1 118.6 67.8 53.0 52.6 26.1 22.4 21.9 14.1 11.7.

Example 4

3-dipropylamino-5-N,N-dimethylcarbamoylchroman

The title compound was prepared analogous to the procedure used in Example 3 starting from 3-dipropylamino-5-methyloxycarbonylchroman and substituting dimethylamine (g) in place of $NH_3$ (g). $^{13}$C-NMR: 189.3 170.3 149.9 137.4 126.7 126.1 124.9 65.8 64.7 48.2 47.7 30.7 26.0 15.1 10.9.

Example 5

3-Dipropylamino-5-N,N-diisopropylcarbamoylchroman

The title compound was prepared analogous to the procedure used in Example 3 starting from 3-dipropylamino-5-methyloxychroman. Mp 228°–230° C. (HCl-salt).

Example 6

3-Dipropylamino-5-N-methylcarbamoylchroman

The title compound was prepared analogous to the procedure used in Example 3 starting from 3-dipropylamino-5-methyloxycarbonylchroman and substituting methylamine (g) in place of $NH_3$ (g). Mp 95°–97° C. (oxalate).

Example 7

3-Dipropylamino-5-acetylchroman

3-Dipropylamino-5-chloroformylchroman*HCl (4.42 g, 13.4 mmol), prepared from 3-dipropylamino-5-methyloxycarbonylchroman (Example 2) analogous to the procedure used in Example 3, in dry tetrahydrofuran (20 ml), was added to a pre-formed solution of lithium dimethylcuprate; prepared from MeLi and CuI, in 200 mL tetrahydrofuran at −78° C. The solution was stirred for 15 minutes at −78° C. and was then allowed to reach room temperature during 10 minutes. Then, 30 mL H₂O was slowly added. The organic phase was decanted, dried with Na₂SO₄ and evaporated to dryness. The residue was purified by flash chromatography (silica gel) by elution with ethyl acetate/hexane 1:8. The title compound was crystallized as salt from ethyl acetate. Mp 106°–108° C. (oxalate).

Example 8

3-Dipropylamino-5-cyclopropylcarbonylchroman

The title compound was prepared analogous to the procedure used in Example 7 substituting lithium dicyclopropylcuprate (J. Org. Chem., 41 (22), 1976) in place of lithium dimethylcuprate. Mp 100°–102° C. (oxalate).

Example 9

3-Dipropylamino-5-tertbutylcarbonylchroman

The title compound was prepared analogous to the procedure used in Example 7 substituting lithium ditertbutylcuprate (from tertbutyllithium and CuBr-Me₂S) in place of lithium dimethylcuprate. Mp 118°–120° C. (oxalate).

Example 10

3-Dipropylamino-5-isopropylcarbonylchroman

The title compond was prepared analogous to the procedure used in Example 7 substituting magnesium diisopropylcuprate (from isopropylmagnesium chloride and CuBr-Me₂S) in place of lithium dimethylcuprate. Mp 60°–62° C. (oxalate).

Example 11

3-Dipropylamino-5-(4-fluorophenylcarbonyl)chroman

The title compound was prepared analogous to the procedure in Example 7, substituting magnesiumdi(4-fluorophenyl)cuprate (from 4-fluorophenyl magnesium bromide and CuI) in place of lithium dimethylcuprate. Mp 98.3°–98.4° C. (oxalate).

Example 12

3-Dipropylamino-5-(2-thienylcarbonyl)chroman

The title compound was prepared analogous to the procedure used in Example 7 substituting lithium di(2-thienyl)cuprate (from 2-thienyllithiumand CuI) in place of lithium dimethylcuprate. Mp 87–88.5 (oxalate).

Example 13

3-Dipropylamino-5-isopropenylchroman

Methyltriphenylphosphoniumbromide (0.62 g, 1.74 mmol) was dissolved in dry ethyl ether (20 ml) under nitrogen at ambient temperature and n-BuLi (0.7 ml, 2.5M, 1.74 mmol) was added and the solution was stirred for 4 hours.

3-Dipropylamino-5-acetylchroman (Example 7; 0.40 g, 1.45 mmol) was dissolved in dry diethyl ether (2.0 ml) and this solution was added to the previously formed Wittig-reagent.

The mixture was stirred at ambient temperature overnight. The solution was diluted with toluene and washed with water. Drying of the organic phase with Na₂SO₄ and evaporation to dryness gave a solid, which was finally purified by flash chromatography by elution with ethyl acetate/hexane 1:4. The collected fractions were evaporated and gave the title compound as a colourless oil. ¹³C-NMR: 11.82 21.94 24.28 26.69 52.79 53.64 67.70 115.03 115.13 118.73 120.07 126.83 144.88 145.27 154.03.

Example 14

3-Dipropylamino-5-aminochroman

3-Dipropylamino-5-methyloxycarbonylchroman (Example 2; 1.0 g, 3.4 mmol) was dissolved in methanol (20 ml). Sodium hydroxide (0.16 g, 4.1 mmol) in water (1.0 ml) was added and the solution was refluxed with nitrogen overnight. The solution was evaporated to dryness, toluene (20 ml) was added and again the solution was evaporated to dryness. The residue was dissolved in toluene 20 ml, diphenylphosphoryl azid (1.87 g, 6.8 mmol) was added and the solution was refluxed for 2 hours. Methanol (2.0 ml) was added and reflux was continued for 4 hours. The solution was cooled, washed with water and extracted with dilute HCl (aq.). The acidic water phase was neutralized NaOH (aq.) and extracted with toluene. The toluene-phase was dried with sodium sulphate and evaporated to dryness. The residue was dissolved in ethanol containing 10% NaOH (20 ml) and the solution was refluxed overnight. The solution was cooled and diluted with toluene. Washing with water, drying of the organic phase and evaporation to dryness afforded the title compound as an oil, which was converted to a dihydrochloride salt. Mp 173°–174° C.

Example 15

3-Dipropylamino-5-nitrochroman

3-Dipropylamino-5-aminochroman (Example 14; 0.050 g, 0.20 mmol) was dissolved in a mixture of trifluoracetic acid (0.080 ml, 1.0 mmol) in water (5 ml). The clear solution was cooled to 0°–4° C. Sodium nitrite (0.017 g, 2.5 mmol) in water (1.0 ml), was added dropwise with good stirring. The solution was stirred for 15 minutes and neutralized with calcium carbonate. A solution of sodium nitrite (0.50 g, 7.2 mmol) in water (1.0 ml) was added followed by a mixture of copper sulfate (0.10 g, 0.62 mmol) and copper (1) oxide in water (1.0 ml). The solution was stirred at 0° C. for 20 minutes and then at ambient temperature for 2 hours. The solution was extracted with diethyl ether. The organic phase was dried with sodium sulfate and evaporated to dryness. The residue was purified by flash chromatography on silica gel by elution with ethyl acetate/hexane 1:9 to give the title compound. Mp 150°–151° C. (hydrochloride).

Example 16

3-Dipropylamino-5-azidochroman

3-Dipropylamino-5-aminochroman (Example 14; 0.050 g, 0.20 mmol) was diazotized according to the procedure of Example 15. After stirring for 15 minutes, sodium azide (0.026 g, 0.4 mmol) in water (1.0 ml) was added. After stirring at 5° C. overninght the solution was worked-up and purified according to the procedure of Example 15 to give the title compound. Mp 167°–168° C. (oxalate).

Example 17

3-Dipropylamino-5-(pyrrol-1-yl)chroman

3-Dipropylamino-5-aminochroman (Example 14; 0.60 g, 2.42 mmol) was dissolved in acetic acid (10 ml) and 2,5-dimethoxytetrahydrofuran (0.40 g, 3.0 mmol) was added. The solution was refluxed for 1 hour. The solution was neutralized with NaOH (aq.) and extracted with toluene. The organic phase was dried with sodium sulfate and evaporated to dryness. The residue was purified by flash chromatography on silica gel by elution with ethyl acetate/ hexane 1:9 to give the title compound. $^{13}$C-NMR: 111.75 21.89 24.81 52.69 53.15 67.94 108.93 115.67 118.22 118.44 121.87 127.22 141.47 155.27

Example 18

3-(Methyl(3-phenylpropyl)amino)-5-hydroxychroman

3-Amino-5-methoxychroman (Thorberg et al. Acta Pharm. Suec. 24(1987)) (2.0 g, 9.28 mmol) was dissolved in methanol (50 ml) and pH was adjusted to 6.0 with acetic acid. The solution was cooled to 0° C. and sodium cyanoborohydrid (0.87 g, 13.8 mmol) was added together with 3-phenylpropanal (1.22 ml, 9.28 mmol), the cooling was withdrawn and the solution was stirred at ambient temperature for 4 hours. Paraformaldehyde (0.42 g, 14 mmol) and sodium cyanoborohydride (0.87 g, 9.28 mmol) was added and stirring was continued overnight at ambient temperature. The solution was diluted with toluene and washed with water. Drying with sodium sulfate and evaporation to dryness gives an oil. The oil was purified by flash chromatography on silica gel by elution with ethylacete/ hexane 1:4. The collected fractions were evaporated to give an oil. The oil was treated with HBr (47% aq.) at 120° C. for 1 hour. The solution was cooled and neutralised with sodium hydroxide and extracted with toluene. The organic phase was dried and evaporated to give the title compound as an oil. $^{13}$C-NMR: 22.502 29.09 33.47 38.19 53.66 67.75 102.04 109.20 110.46 125.78 127.05 128.36 142.20 155.29 158.28.

Example 19

3-(methyl(3-phenylpropyl))amino-5-methyloxycarbonylchroman 3-(methyl(3-phenylpropyl))amino-5-hydroxychroman (Example 18; 1.0 g, 3.37 mmol) was dissolved in $CH_2Cl_2$ (20 ml) at −20° C. Pyridine (0.32ml, 4 mmol), trifluoromethanesulfonic anhydride (0.65 ml, 5.9 mmol) and dimethylaminopyridine (DMAP), (0.041 g, 0.59 mmol) was added at −20° C. under nitrogen. The solution was stirred for 3 hours at −20° C. Cooling was withdrawn and the solution was diluted with toluene, washed with sodium hydrogen carbonate (aq.), dried with sodium sulfate, filtered through silica gel and evaporated to dryness. The remaining oil was dissolved in 13 ml degassed methanol/DMF 3:10. Palladium acetate (0.056 g, 0.25 mmol), 1,3-bis(diphenylphosphino)- propane (0.103 g, 0.25 mmol) and triethyl amine (0.76 ml, 5 mmol) was added and the solution was flushed with CO(g) under vigorous stirring. The pressure in the reaction vessel was raised to 20.2 KPa(e) with the aid of a CO(g)-cylinder fitted with a regulator. Stirring was continued overnight at 75° C. The pressure and temperature was normalized and the solution was diluted with toluene and washed with water.

The organic phase was dried and evaporated to dryness. The remaining oil was purified by flash chromatography on silica gel by elution with ethyl acetate/hexane 1:4. The collected fractions were evaporated to give the title compound as a colourless oil. $^{13}$C-NMR: 26.88 29.00 33.20 37.85 51.64 53.37 55.44 67.24 120.60 123.06 123.40 125.59 126.47 128.17 128.24 130.36 142.01 154.93 167.29.

Example 20

3-(methyl(3-phenylpropyl))amino-5-N-methylcarbamoyl chroman 3-(methyl(3-phenylpropyl))amino-5-methyloxycarbonylchroman (Example 19; 0.32 g, 0.94 mmol) was dissolved in methanol (10 ml). NaOH (0.08 g, 2 mmol) in 1 ml water was added and the solution was refluxed overnight under nitrogen. The solution was evaporated to dryness and co-evaporated with toluene (10 ml) to dryness again. The remaining solid was refluxed in $SOCl_2$ for 30 minutes and evaporated to dryness. The pale brown gum was dissolved in tetrahydrofuran (THF) 20 ml and treated with methyl amine (g) for 1 minute under vigorous stirring. The solution was diluted with toluene and washed with sodium hydrogen-carbonate (aq.). Drying and evaporation gave a gum, which was finally purified by flash chromatography on silica gel by elution with ethyl acetate/ hexane 1:2. The collected fractions were evaporated to give the title compound as a colourless gum. Crystallization from ethyl acetate as oxalate gave white needles. Mp 150°–151° C. (oxalate).

Example 21

3-Dipropylamino-5-trifluoromethanesulfonylthiochroman

3-Dipropylamino-5-hydroxybenzothiopyran (EP 0222 996; 420 mg, 1.58 mmol) and collidine (0.27 g, 0.29 mL) were dissolved in 15 mL of $CH_2Cl_2$ and cooled to −30° C.

Trifluoromethanesulfonic anhydride (0.54 g, 0.32 mL) was added dropwise and allowed to reach ambient temperature, and after 20 minutes diluted with methylendichloride.

The solution was washed with saturated $NaHCO_3$, dried with $Na_2SO_4$, and evaporated in vacuo.

Chromatography on silica by elution with $CHCl_3$ gave 0.62 g of the title compound as the base. Yield: 98%. Mp. 37°–8° C.; $^{13}$C NMR (200 MHz—$CDCl_3$) PPM 148.3, 136.7, 128.4, 127.2, 126.3, 122.0, 117.1, 115.2, 55.6, 52.5, 28.0, 26.6, 22.6, 11.8.

Example 22

3-Dipropylamino-5-methyloxycarbonylthiochroman

3-Dipropylamino-5-hydroxybenzothiopyran (EP 0222 996; 620 mg, 1.6 mmol) was dissolved in 11 mL of dimethylformamide/methanol (6:2) and the solution was degassed (10 mm, 22° C., 15 min). $Pd(OAc)_2$ (11 mg), 1,3-bis-diphenylphosphinopropane (19 mg), and triethylamine (0.48 mL, 0.35 g) were added to the reaction mixture.

The mixture was heated to 70° C. under carbonmonoxide atmosphere and stirred for 5 hours. The solution was cooled, diluted with 30 mL of toluene, washed with saturated $NaHCO_3$, dried with $Na_2SO_4$, and evaporated in vacuo.

Chromatography on silica by elution using a gradient $CHCl_3 \rightarrow 10\%$ EtOAc/$CHCl_3$ gave 310 mg of the title compound (base) as a slightly yellow oil; Yield: 64%. $^{13}$C NMR (200 MHz—$CDCl_3$) PPM 168.2, 136.6, 134.8, 131.6, 130.1, 126.5, 125.7, 56.7, 52.5, 52.1, 30.4, 28.0, 22.3, 11.9.

Example 23

3-Dipropylamino-5-acetylthiochroman

3-Dipropylamino-5-methyloxycarbonylthiochroman (Example 22; 310 mg, 1.01 mmol) was dissolved in 8 mL methanol and 60 mg of sodium hydroxide in 2 mL water was added. After 5 hours reflux the mixture was cooled and evaporated in vacuo. The residue was dissolved in thionylchloride (5 ml) and refluxed for 1 hour. The excess thionylchloride was evaporated in vacuo to obtain a gum.

The residual gum was dissolved in a minimal amount of tetrahydrofuran and added dropwise to a cooled (−78° C.) solution of lithium dimethyl cuprate (2.02 mmol) in 20 mL of tetrahydrofuran.

The reaction mixture was stirred for 15 minutes at −78° C., then allowed to reach ambient temperature and after 10 minutes the reaction was quenched with 0.9 mL of water.

The reaction was filtered through Celite and evaporated to dryness.

The residue were dissolved in ether, washed with saturated $NaHCO_3$, treated with brine, dried with $Na_2SO_4$, and evaporated in vacuo to afford the crude base as an oil.

The crude residue was chromatographed on silica by elution using a gradient of $CHCl_3 \rightarrow 5\%$ EtOAc/$CHCl_3$.

The hydrochloride salt was obtained by dissolving the pure base in ether and dropping an excess of an ethereal HCl solution. Recrystallization in trichloromethane/diethylether gave 92 mg of the title compound as a white solid; Yield: 27%. Mp 141°–2° C.; $^{13}$C NMR (200 MHz—$CDCl_3$) PPM 201.9, 138.4, 135.9, 131.7, 131.2, 127.2, 127.0, 59.9, 54.1, 51.8, 29.9, 27.9, 26.1, 18.6, 18.2, 11.6.

Example 24

5-Allyl-3-(dipropylamino)thiochroman

To a solution of 3-(dipropylamino)-5-trifluoromethanesulfonylthiochroman (Example 21; 1.28 g, 3.22 mmol), tetrakis(triphenylphosphine)palladium(0) (76 mg, 0.064 mmol) and a few crystals of 2,6-di-t-butyl-4-methylphenol in 10 mL anhydrous toluene was 1.17 g (1.1 mL, 3.53 mmol) tributylallyltin added neat. The resulting solution was refluxed for 4 hours then pyridine (1 mL) was added to the cooled solution followed by 2.1 ml of a hydrogen fluoride-pyridine complex (Stille J. K. et al. JOC 52(1987) 422).

After stirring for 1 hour at room temperature, the reaction mixture was diluted with 50 ml diethyl ether and treated, successively, with 50 mL 1M NaOH solution, $H_2O$ (×2), washed with a saturated NaCl solution and dried ($NaSO_4$). After filtering and removal of the solvent in vacuo, the crude was obtained as a dark oil.

Chromatography on silica by elution using a gradient hexane →5% EtOAc/hexane gave 0.85 g of the title compound (base) as a slightly yellow oil. Yield: 91%. $^{13}$C NMR: (200 MHz—$CDCl_3$) PPM 139.0, 136.5, 134.0, 133.0, 126.1, 125.9, 125.0, 116.0, 57.0, 52.6, 37.7, 29.5, 27.7, 22.5, 11.9.

A portion of the base was taken out and made into the hydrochloride salt by dissolving the pure base in ether and dropping an excess of an ethereal HCl solution. Recrystallizing (AcCN-Et20-hexane) gave a white solid. Mp 164°–5° C.

Example 25

3-(Dipropylamine)-5-propylthiochroman hydrochloride

To a stirred suspension of potassium azodicarboxylate (0.76 g, 3.9 mmol) (made fresh from diethyl azocarboxylate and potassium hydroxide) and 5-allyl-3-(N,N-dipropylamino)thiochroman (Example 24; 0.4 g, 1.4 mmol) in 10 mL anhydrous methanol was added a solution of glacial acetic acid/methanol (1:4) until the yellow color (from the potassium salt) disappeared.

After 30 min stirring at room temperature more potassium azodicarboxylate (200 mg) was added and again decomposed as before. This process was continued until analysis (GC) showed no starting material remaining.

Upon completion, (2 hours and 4 additions of the potassium salt) the solvent was removed in vacuo. To the remains, a 2M NaOH solution was added which was extracted (×2) with diethyl ether and the combined organic portions were treated with a saturated NaCl solution, and dried ($Na_2SO_4$). The crude base was obtained as a light colored oil upon the removal of the solvent in vacuo.

Chromatography on silica by elution using a gradient hexane—5% EtOAc/hexane gave the title compound (base) as a clear oil. The hydrochloride salt was made by dissolvning the pure base in ether and dropping and an excess of an ethereal HCl solution. Recrystallizing (chloroform-$Et_2O$) gave 0.30 g of a white solid. Yield: 66%. Mp 150°–151° C. $^{13}$C NMR: (on base, 200 MHz—$CDCl_3$) PPM 141.6 133.7 132.8, 125.8, 125.6, 124.5, 57.1, 52.6, 35.3, 29.5, 27.6, 23.6, 22.4, 14.3, 11.9.

Example 26

5-Methoxy-3-cyclopropylamino-chroman hydrochloride

The title compound was prepared according to known methods for reductive amination (Clinton F. Lane Synthesis 1975 vol. 146 p 135) from methoxy-3-chromanone and cyclopropylamine. Mp 188°–189° C.

Example 27

3-(N-Cyclopropylamino)-5-hydroxychroman 3-(N-Cyclopropylamino)-5-metoxychroman hydrochloride (5.6 g, 22 mmol) was suspended in $CH_2Cl_2$ (140 mL) under $N_2$. The mixture was cooled on a dry-ice/EtOH bath to −20° C. $BBr_3$ (4.1 mL, 44 mmol) dissolved in $CH_2Cl_2$ (60 mL) was added to the stirred mixture during 0.5 hour. The yellow clear solution was slowly warmed to 0° C. and kept at that temperature until GC indicated a complete reaction (after 3–5 hours). Then the solution was poured on crushed ice (200 g) and enough conc. $NH_3$ (aq.) to make a pH of 8–9. The mixture was extracted with ether (3×200 mL). The collected ether phases were dried ($MgSO_4$), filtered and concentrated in vacuo to afford a white solid. Crystallization from absolute EtOH afforded 3-(N-cyclopropylamino)-5-hydroxychroman (3.9 g, 88% yield) as colourless needles. Mp 147.degree.–148.degree. C.

Example 28

3-(N-Cyclopropylamino)-5-trifluoromethanesulfonyloxychroman

The title compound was prepared in analogy to the procedure used in example 1 starting from the product formed in example 27. The base was characterized as the hydrochloride salt. Mp 207.degree.–209.degree. C. (decomp).

Example 29

3-(N-Cyclopropylamino)-5-(N-cyclopropyl)carbamoylchroman 3-(N-Cyclopropylamino)-5-trifluoromethanesulfonyloxychroman (0.51 g, 1.5 mmol) and triethylamine (0.46 mL, 3.3 mmol) was dissolved in DMF (7.5 mL) in a 200 mL hydrogenation bottle. The bottle was evacuated, followed by inlet of CO (repeated three times). Cyclopropylamine (2.9 mL, 42 mmol), 1,3-bis(diphenylphosphino)propane (0.023 g, 55 .mu.mol) and palladium(II)acetat (0.12 g, 55 .mu.mo) were added and then the mixture was shaken at 70.degree. C. for 3 hours at CO pressure of 2–2.5 bars. After cooling to room temperature the reaction mixture was partitioned with saturated NaHCO.sub.3 and ether (5.times.30 mL). The collected ether phases were dried (MgSO.sub.4), filtered and concentrated in vacuo. Flash chromatography on silica of the crude product with TH-F-EtOAc (8:92) as eluent afforded 0.32 g of a white solid. Recrystallization from THF-ether gave 3-(N-cyclopropylamino)-5-(N-cyclopropyl)carbamoylchroman 0.17 g, 42% yield) as colourless needles. Mp 126.degree.–127.degree. C.

Example 30

3-Cyclopropylamino-5-[N-(2,6-xylidino)carbamoyl]-chroman hydrochloride

The sodium, salt of 3-(N-cyclopropyl-N-trifluroacetyl)aminochroman-5-carboxylic acid (2.1 mmol) obtained from example 28 after N-trifluoroacetylprotection, esterification (according to example 2) and subsequent hydrolyze and thionyl chloride (10 mL) under $N_2$ was refluxed for 2 hours. The excess of thionyl chloride was co-evaporated for several times with dry toluene on a rotatory evaporator. The acid chloride thus obtained was dissolved in methylene chloride (10 mL) and added dropwise to a stirred solution of 2,6-dimetylanilin (0.52 g, 4.3 mmol) and dry pyridine (6 mL) under $N_2$ at room temperature. When the reaction was complete (within 2 hours according to TLC and capillary-GC) the volatiles were evaporated on a rotary evaporator. The residue was redissolved in dry toulene and concentrated in vacuo repeatedly (four times). Purification by flash chromatography on silica with THF-n-hexan (1:4) as eluent gave 0.72 g of 3-(N-cyclopropyl-N-trifluoroacetylamino)-5-[N-(2,6-xylidino)carbamoyl]-chroman (72% yield) as a colourless solid. Mp 146°–149° C. (crystallized from $CHCl_3$-n-hexan). Part of this amide (0.44 g, 0.95 mmol) was added in small portions during 15 minutes to a stirred suspension of lithium tetrahydridoaluminate (0.072 g, 1.9 mmol) in 20 mL of dry THF (distilled from sodium bensophenone ketyl) under $N_2$. The mixture was stirred at 45° C. until TLC and capillary-GC indicated a complete reaction (after fourty hours) and then quenched by careful addition of aqueous sodium potassium tartrate (0.5M).

After adjusting pH to 10 (concentrated ammonia) the solution was extracted with ether (2×50 mL). The collected ether phases were dried ($K_2CO_3$), filtered and concentrated in vacuo. The resulting oil was chromatographed on a silica column eluted with $CHCl_3$-EtOAc(1:1) to give 3-cyclopropylamino-5-[N-(2,6-xylidino)carbamoyl]-chroman (0.071 g; 22% overall yield) as an oil. A slight excess of HCl (approx. 3M in ether) was added dropwise to a stirred and chilled (+4° C.) solution of the base from above and methanol (2–4 mL). The solvents were then rotarory evaporated, ether was added and evaporated repeatedly to strip traces of HCl. The oil solidified when the flask, filled with ether, was left in the refrigerator overnight.

Crystallization from absolute EtOH afforded 3-cyclopropylamino-5-[N-(2,6-xylidino)carbamoyl]chroman hydrochloride as colourless needles. Mp 189°–191° C. (decomp).

Example 31

3-(N,n-Diallylamino)-5-methoxychroman and 3-(N-Allylamino-5-methoxychroman

3-Amino-5-methoxychroman hydrochloride (Acta Pharm. Suec. 24 (1987) (5.0 g, 23 mmol), allyl bromide (3.4 mL, 39 mmol), anhydrous $K_2CO_3$ (9.6 g, 69 mmol) and DMF (8.0 mL) were stirred under $N_2$ at room temperature for 72 hours. Ether (150 mL) was added, the salts were filtered off by suction and the clear filtrate was concentrated in vacuo. The residue was purified on a silica column eluted with 1000 mL THF-n-hexan (1:9) and 1000 mL THF-hexan (1:3) to afford 3-(N-allylamino)-5-methoxychroman (1.7 g; 33% yield) and 3-(N,N-diallylamino)-5-methoxychroman (3.4 g, 56% yield) as oils. The diallylamino derivative above was isolated as the hydrochloride salt by addition of a slight excess of HCl (approx. 3M in ether) to an ether solution of the amine. The crude HCl salt crystallized on standing, with ether, in the cold. Mp 139°–140° C.

Example 32

3-(N-allyl-N-n-propylamino)-5-methoxychroman 3-(N-Allylamino)-5-methoxychroman (1.3 g, 5.9 mmol) prepared analogous to example 26, n-propyl iodide (2.1 mL, 21 mmol), anhyrous $K_2CO_3$ (3.0 g, 21 mmol) and acetonitrile (5.5 mL) were stirred under $N_2$ at 47° C. (oilbath temp) for five days until GC indicated complete reaction. Ether (40 mL) was added, the salts were filtered off by suction and the clear filtrate was concentrated in vacuo to afford 3-(N-allyl-N-n-propylamino)-5-methoxy chroman (1.24 g, 81% yield) as an oil. The base was precipitated from an ether solution by adding a slight excess of HCl (approx. 3M in ether). Crystallization of the crude HCl salt afforded colourless needles. Mp 117°–118° C.

Example 33

3-(N-allyl-N-n-propylamino)-5-hydroxychroman

The title compound was prepared in analogy to the procedure used in example 27 using the product obtained in example 32. Crystallization from $CHCl_3$-n-hexane gave colourless needles. Mp 78°–80° C.

Example 34

3-(N-Allyl-N-n-propylamino)-5-trifluoromethanesulfonyloxychroman

The title compound was prepared in analogy to the procedure in example 1 using the product from example 33 as starting material.

MS (EI, 70 eV) m/z 379 (M+, 8%), 350 (100%), 246 (10%).

Example 35

5-Acetyl-3-(N-Allyl-N-n-propylamino)chroman 3-(N-Allyl-N-n-propylamino)-5-trifluoromethanesulfonyloxychroman (0.28 g, 0.74 mmol), LiCl (0.097 g, 2.3 mmol), $PdCl_2$ (dppf) (0.031 g, 0.04 mmol) and 2,6-di-t-butyl- 4-methylphenol (0.005 g) were dissolved in DMF (5.0 mL) in a three-necked round-bottom flask (50 mL) with a magnetic stirrer. The flask was evacuated, followed by inlet of CO (three times). Tetramethyltin (0.12 mL, 0.89 mmol) was added and then the mixture was stirred under an atmosphere of CO (1 atm) at 120° C. (oilbath temp) for 4 hours. The solvent was evaporated, the residue was partitioned between aqueous $NH_3$ (2M) and $CH_2Cl_2$ (3×15 mL) and the organic phases were dried ($Na_2SO_4$), filtered and concentrated in vacuo. Column chromatography on silica with THF-n-hexane (1:9) as eluent afforded 5-acetyl-3-(N-allyl-N-n-propylamino)chroman (0.078 g, 39% yield)

as an oil. The base was precipitated from an ether solution by adding a slight excess of HCl (approx. 3M in ether). The crude salt was collected and dried in vacuo at 40° C. to give a white amorphous powder. Mp 125°–127° C. PdCl$_2$(dppf) =dichloro[1,1'-bis(diphenylphosphino)ferrocene]-palladium (II).

Example 36

3-isopropylamino-5-methoxychroman hydrochloride

The title compound was prepared analogous to the procedure used in example 26 starting from 5-methoxy-3-chroman and isopropylamine. Mp 255° C.

Example 37

3-(N,N-isopropyl,n-propyl)amino-5-methoxychroman

A mixture of the product obtained in example 36 (14 g, 0.06 mol) 1-iodopropane (15 g, 0.08 mol), K$_2$CO$_3$ and acetonitile (250 ml) was stirred with reflux for 4 days. After chromtography the desired product was isolated as a colourless oil. GC-MS(CI-mode) M+1=264 (100%).

Example 38

3-(N,N-isopropyl,n-propyl)amino-5-hydroxychroman

The product from example 37 (10 g, 0.038 mol) was demethylated using BBr$_3$ in dichloromethane. GC-MS(CI-mode) M+1=250 (100%).

Example 39

3-(N,N-isopropyl,n-propylamino)-5-trifluoromethanesulfonoxychroman

The title compound was prepared analogous to the procedure used in example 1 using the product from example 38 as starting material. GC-MS(CI-mode) M+1=382 (100%).

Example 40

5-Acetyl-3-(N-isopropyl-N-n-propylamino)chroman hydrochloride

The title compound was prepared analogous to example 35 starting from the product obtained in example 39 and with the addition of CO in a Parr-apparatus at 2 bar. Mp 170° C.

Example 41

3-(N-isopropyl-N-n-propylamino)-5-methyloxycarbonylchroman

The title compound was prepared analogous to the procedure used in example 2 starting from the product obtained in example 39 (3 g, 0.016 mol), Pd(OAC)$_2$ (75 mg), 1,3-bis(diphenylphosphine) propane (150 mg), DMF (50 ml) and methanol (25 ml) in a Parr-apparatus under CO pressure (2 bar) at 70° C. for 6 hours. GC-MS(CI-mode) M+1=292 (100%).

Example 42

3-(N-isopropyl-N-n-propylamino)-5-(N-methyl)-carbamoylchroman hydrochloride

The product obtained from example 41 (1 g, 0.0034 mol), NaCN (50 mg), methanol (30 ml) and a saturated water solution of CH$_3$NH$_2$ (5 ml) was reacted in a steel wessel at 80° C. over night. After work up the colourless oil was transferred to the hydrochloride salt. Mp 123° C.

Example 43

3-(N-isopropyl-N-n-propylamino)-5-(N-ethyl)-carbamoylchroman hydrochloride

The title compound was prepared analogous to the procedure used in example 42, starting from the product obtained in example 41 (1 g, 0.0034 mol), KCN (50 mg), methanol (40 ml) and ethylamine (5 ml, 70% water solution) in a steel wessel at 80° C. for 4 days. Chromotographic work up gave a colourless oil which was converted to the HCL-salt. Mp 198° C.

Example 44

3-N-Cyclopropylmethyl-N-n-propylamino)-5-(N-cyclopropylmethyl)carbamoylchroman

The title compound was prepared from 3-(N-cyclopropylmethyl-N-n-propylamino)-5-trifluoromethanesulfoxyloxychroman (1.08 g, 0.0026 mol) obtain analogous to the example 36–39, 1,3-bis (diphenyl phosphine)propane (40 g), palladium (II) acetate (22 mg), and cyclopropylmethylamine (2.3, 0.0264 mol) in 30 ml DMF was placed in a Parr glass essel. CO at 2 bar was added and the mixture was shaken at 60° C. for 4 hours. After work up and chromatographic purifications the desired compound was obtained as white crystalls with mp 124° C. (base) as needles. Mp 94°–95° C.

Example 45

3-(N-cyclopropyl-N-n-propylamino)-5-phenylchroman hydrochloride

The title compound was prepared from a mixture of 3-(N-cyclopropyl-N-n-propylamino)-5-trifluoromethylsulfonyloxychroman obtained analogous to the example 36–39 (2 g, 5.1 mmol), trimethylphenylstannane (1.8 g, 4.8 mmol), tetratis (triphenylphosphine)-palladium (0) (280 mg, 0.24 mmol).

Lithiumchloride (600 mg, 14.4 mmol) and 2,6-di-t-butyl-4-methylphenol in 60 ml dioxane and 6 ml DMF was stirred at 105° C. In a steel wessel for 3 days. The mixture was filtered and extracted. Chromatographic purification on an alumenia column gave the desired compound in 55% yield. The compound was isolated as the hydrochloride salt. Mp 160° C.

Example 46

3-(N,N-dipropylamino)-5-N-cyclopropyl)-carbamoylthiochroman 3-(N,N-Dipropylamino)-5-trifluoromethanesulfonyloxythiochroman (0.70 g, 1.76 mmol), triethylamine (0.39 g, 0.54 mL, 3.9 mmol) and DMF (5 mL) were mixed together and the solution was degassed (10 mmHg, RT, 15 min) then subjected to CO atmosphere (×3). Then palladium (II) acetate (12 mg), 1,3-bis-diphenylphospinopropane (22 mg), and cyclopropylamine (3.0 g, 3.7 mL, 52.8 mmol) were added. The resulting mixture was again subjected to CO atmosphere and heated to 70° C. with stirring for 4 hours. The solution was cooled, evaporated in vacuo (vacuum pump), then diluted with ethyl acetate. The mixture was washed with bicarbonate solution (three times), treated with brine, dried (Na₂SO₄), and evaporated in vacuo to give crude. Chromatography on silica (eluent: 50% EtOAc/hexane) gave 0.38 g as white hard crystals (64% yield).

Mp 109°–110° C. $^{13}$C NMR: (200 MHz—CDCl₃) PPM 171.1 137.8 134.5 133.2 128.0 126.0 122.7 56.5 52.5 29.9 28.1 23.0 22.4 11.9 7.0.

Example 47

3-(N,N-Dipropylamino)-5-methyloxycarbonylthiochroman (3-(N,N-Dipropylamino)-5-trifluoromethanesulfonylthiochroman (620 mg, 1.6 mmol) was dissolved in 11 mL of DMF/methanol 6:2 and the solution was degassed for 15 min. Pd(OAc)₂ (11 mg), 1,3-bis-diphenyl-phosphinopropane (19 mg), and triethylamine (0.48 mL, 0.35 g) were added to the reaction mixture. The mixture was heated to 70° C. under carbonmonoxide atmosphere and stirred for 5 hours. The solution was cooled, diluted with 30 mL of toluene, washed with saturated NaHCO₃, dried (Na₂SO₄) and evaporated in vacuo.

Chromatography on silica (eluent: gradient CHCl₃→10% EtOAC/CHCl₃) gave 310 mg (64% yield) of the title compound (base) as a slightly yellow oil. $^{13}$C NMR: (200 MHz—CDCl₃) PPM 168.2, 136.6, 134.8, 131.6, 130.1, 126.5, 125.7, 56.7, 52.5, 52.1, 30.4, 28.0, 22.3, 11.9.

Example 48

3-(N-Isopropyl-N-n-propylamino)-5-phenyl-1-oxothiochroman 3-(N-Isopropyl-N-n-propylamino)-5-phenylthiochroman hydrochloride (310 mg, 0.86 mmol) was dissolved in 6 mL chloroform and to the cooled solution (ice-bath) was m-chloroperbenzoic acid (348 mg, 1.72 mmol) added in one portion.

The reaction was allowed to stir at room temperature for 18 h. The solvent was removed in vacuo and the remains were extracted with ether/2M NaOH, treated with brine and dried (Na). The solvent was evaporated in vacuo to give the crude mixture.

Chromatography on silica (eluent: 25% EtOAc/CH₂Cl₂) gave 79 mg (27% yield) of the desired sulphoxide as a diastereomeric mixture (18:82 by GC) obtained as an off-white solid. Mp 109°–112° C.

Example 49

5-(2-Furanyl)-3-(N-isopropyl-N-n-propylamino)-1-oxothiochroman 5-(2-Furanyl)-3-(N-isopropyl-N-n-propylamino) thiochroman hydrochloride (341 mg, 0.97 mmol) was dissolved in 7 mL methylene chloride and cooled to –20° C. m-Chloroperbenzoic acid (258 mg, 1.27 mmol) was added in one portion and the reaction was allowed to stir at room temperature for 18 h.

The solvent was removed in vacuo and the remains were extracted with ether/2M NaOH, treated with brine and dried (Na₂SO₄). The solvent was evaporated in vacuo to give the crude mixture.

Chromatography on silica (eluent: 25% EtOAc/CH₂Cl₂) gave 35 mg of the non-polar diastereomer of the title compound, 75 mg of the polar (major) diastereomer of the title compound and 92 mg as a diastereomeric mixture (25:75 by GC) to give a combined yield of 63%.

Non-polar (minor) isomer (off-white solid): Mp 63°–65° C. Polar (major) isomer (off-white solid): Mp 83°–85° C.

Example 50

5-(2-Furanyl)-3-(N-isopropyl-N-n-propylamino)-1,1-di-oxothiochroman 5-(2-Furanyl)-3-(N-isopropyl-N-n-propylamino)-1-oxothiochroman (as a diastereomeric mixture (25:75 by GC)) (92 mg, 0.29 mmol) was dissolved in ether and HCl in ether was added dropwise until the solution was acidic. The solvent was removed in vacuo. The white solid obtained was dissolved in 3 mL methylene chloride and the solution was cooled to –15° C.

m-Chloroperbenzoic acid (118 mg, 0.58 mmol) was added in one portion and the reaction was allowed to stir at room temperature for 18 h. Only the minor diastereomer reacted to give the desired sulphone due to steric reasons. The solvent was removed in vacuo and the remains were extracted with ether/2M NaOH, treated with brine and dried (Na₂SO₄).

The solvent was evaporated in vacuo to give the crude mixture.

Chromatography on preparative TLC(eluent: 20% EtOAc/CH₂Cl₂) gave 5 mg (5% yield) of the title compound.

MS 347 $^{13}$C NMR (200 MHz—CDCl₃) PPM 151.7, 143.0, 139.3, 132.3, 131.6, 127.5, 125.6, 123.5, 111.7, 110.5, 54.3, 51.3, 49.4, 47.4, 34.4, 23.3, 21.7, 20.0, 11.8.

Example 51

5-(2-Furanyl)-3-(N-isopropyl-N-n-propylamino) thiochromanhydrochloride

To a solution of 3-(N-isopropyl-N-n-propylamino)-5-trifluoromethanesulfonylthiochroman (0.92 g, 2.31 mmol), ethanol (10.2 mL), lithium chloride (0.20 g, 4.8 mmol), 2M sodium carbonate (3.4 mL), and tetrakis (triphenylphosphine)palladium(O) (49 mg, 0.042 mmol) dissolved in toluene (23 mL) was 2-furanylboronic acid (0.62 g, 4.6 mmol) added in one portion under nitrogen. The resulting solution was heated to 95° C. for 2 hours then the reaction was allowed to cool. The reaction was filtered and the solvent was evaporated in vacuo. The remains were taken into ether, washed with 2M NH₃, treated with brine and dried (NaSO₄). Removal of the solvent in vacuo gave the crude compound.

Chromatography on silica (eluent: 3% EtOAc/CHCl₃) gave 0.68 g (93% yield) of the title compound (base) as a slightly yellow oil.

The hydrochloride salt was made by dissolving the pure base in ether and dropping an excess of an ethereal HCl then recrystallized (EtOAc/ether) to give colorless crystals. Mp 145°–147° C.

Example 52

5-Isopropylamido-3-(N-isopropyl-N-n-propylamine) thiochroman 3-(N-Isopropyl-N-n-propylamino)-5-trifluoromethnaesulfonylthiochroman (0.99 g, 2.49 mmol) was dissolved in dioxane (15 mL) and the solution was degassed (10 mmHg, RT) then subjected to CO atmosphere (×3).

Isopropylamine (1.1 mL, 12.5 mmol), palladium acetate (15 mg) and 1,3-bis-di-phenylphospinopropane (29 mg)

were added. The resulting mixture was again subjected to CO atmosphere and heated to 80° C. with stirring for 4 h.

The solution was cooled, evaporated in vacuo (vacuum pump), then diluted with ether. The mixture was washed with a 2M $NH_3$ solution (×2), treated with brine, dried ($NaSO_4$) and evaporated in vacuo to give crude.

Chromatography on silica (eluent: 30% EtOAc/hexane) gave 0.76 g oil (87% yield) that crystallized and was recrystallized (hexane) to give a white solid. Mp 90°–91° C.

Example 53

3-(N-Isopropyl-N-n-propylamino)-5-trifluoromethanesulfonylthiochroman

5-Hydroxy-3-(N-isopropyl-N-n-propylamino) thiochroman (3.13 g, 11.9 mmol) and collidine (2.02 g, 2.2 mL, 16.7 mmol) were dissolved in 100 mL of $CH_2Cl_2$ and cooled to –30° C. Trifluoromethanesulfonic anhydride (4.03 g, 2.4 mL, 14.3 mmol) was added dropwise and allowed to warm to ambient temperature, and after 20 min diluted with $CH_2Cl_2$. The solution was washed with saturated $NaHCO_3$, dried ($Na_2SO_4$) and evaporated in vacuo.

Chromatography on silica (eluent: 3% EtOAc/hexane) gave 3.9 g (83% yield) of the title compound as a slightly yellow oil. MS 397. $^{13}C$ NMR: (200 MHz—$CDCl_3$) PPM 148.3, 136.7, 128.8, 127.2, 126.3, 121.9, 117.0, 115.5, 52.8, 48.8, 47.1, 30.2, 28.8, 23.7, 21.2, 20.9, 11.7.

Example 54

3-(N-Isopropyl-N-n-propylamino)-5-methyloxycarbonylthiochroman 3-(N-Isopropyl-N-n-propylamino)-5-trifluoromethanesulfonylthiochroman (0.97 g, 2.44 mmol) was dissolved in 17 mL of DMF/methanol 6:2 and the solution was degassed for 15 min. $Pd(OAc)_2$ (17 mg), 1,3-bis-diphenyl-phosphinopropane (29 mg) and triethylamine (0.54 g, 0.75 mL, 5.4 mmol) were added to the reaction mixture. The mixture was heated to 70° C. under carbonmonoxide atmosphere and stirred for 4 hours.

The solution was cooled, diluted with toluene, washed with saturated $NaHCO_3$, dried ($Na_2SO_4$) and evaporated in vacuo.

Chromatography on silica (eluent: 5% EtOAc/hexane) gave 0.69 g (92% yield) of the title compound (base) as a clear oil.

MS 307. $^{13}C$ NMR: (200 MHz—$CDCl_3$) PPM 168.3, 137.0, 134.8, 131.6, 130.1, 126.5, 125.7, 53.9, 52.2, 48.9, 47.3, 32.7, 30.1, 23.8, 21.1, 11.8.

Example 55

3-(N-isopropyl-N-n-propylamino)-5-phenylthiochromanhydrochloride.

To a solution of 3-(N-isopropyl-N-n-propylamino)-5-trifluoromethanesulfonylthiochroman (0.95 g, 2.39 mmol), ethanol (10.5 mL), lithium chloride (0.20 g, 4.8 mmol), 2M sodium carbonate (3.5 mL), and tetrakis (triphenylphosphine)palladium(0) (50 mg, 0.043 mmol) dissolved in toluene (23 mL) was phenylboronic acid (0.35 g, 2.9 mmol) added in one portion under nitrogen. The resulting solution was heated to 95° C. for 5 hours then the reaction was allowed to cool. The reaction was filtered and the solvent was evaporated in vacuo. The remains were taken into ether, washed with 2M $NH_3$, treated with brine and dried ($NaSO_4$). Removal of the solvent in vacuo gave the crude compound.

Chromatography on silica (eluent: $CH_2Cl_2$) gave 0.73 g (94% yield) of the title compound (base) as an oil.

The hydrochloride salt was made by dissolving the pure base in ether and dropping an axcess of an ethereal HCl then recrystallized (EtOAc/ether) to give a slightly yellow solid. Mp 110°–112° C.

Example 56

(R)-3-(N-Isopropyl,N-n-propylamino)5-(3-thiophene)chroman.

(R)-3-(N-isopropyl,N-n-propylamino)5-trifluoromethanesulfonyloxychroman (0.3 g, 0.8 mmol), 3-thiopheneboronic acid (0.2 g, 1.6 mmol), LiCl (0.07 g, 1.6 mmol), $NA_2CO_3$ (2M, 3 mL), EtOH (7 mL) and toluene (15 mL) was mixed in a three-necked round-bottom flask under a nitrogen atmosphere. The catalyst $(Pd(PPh_3)_4$, was added and the reaction mixture was stirred at 90° C. for 4 h. The solvent was removed in vacuo until about 15 mL was left before diluted with diethyl ether, washed ($NH_3$, 2M) and dried (Mg $SO_4$). The solvent was removed in vacuo to give a brownish oily residue which was purified by flash-chromatography ($SiO_2$, $CH_3Cl_2$/EtOAc, 10:1) to give the title compound in 80% yield (0.2g). α(base)=–40° (MeOH, 0.1M, 22° C.). The HCl-salt was precipitated from diethyl ether at 0° C. Mp. 174°–175° C.

Example 57

(R)-3-(N-Isopropyl,N-n-propylamino)5-(2-thiophene)chroman.

(R)-3-(N-Isopropyl,N-n-propylamino)-5-trifluoromethanesulfonyloxychroman (0.4 g, 1.1 mmol), 2-thiophene-boronic acid (0.27g, 2.1 mmol), LiCl (0.09 g, 2.1 mmol), $Na_2CO_3$ (2M, 3 mL), EtOH (7 mL) and toluene was mixed under a nitrogen atmosphere before $Pd(PPh_3)_4$ (0.03 g, catalytic amount) was added. The mixture was then stirred for 8 hours at 90° C.

The solvent was removed in vacuo until 10 mL was left. The residue was diluted with diethyl ether, washed with NH3 (2M) and dried ($MgSO_4$). The solvent was removed in vacuo to give a brownish oily residue which was purified by flash-chromatography ($SiO_2$, $CH_2Cl_2$/EtOAc, 10:1) to give the title compound in 94% in yield (0.3 g). α(base)=–36° (MeOH, 0.1M, 22° C.). The HCl-salt was precipitated from diethyl ether at 0° C. Mp 189°–191° C.

Example 58

(R)-5-Isopropoxycarbonyl,3-(N-isopropyl,N-n-propylamino)chroman (R)-3-(N-Isopropyl,N-n-propylamino)5-trifluoromethanesulfonyloxychroman (0.4 g, 1.1 mmol), triethylamine (0.2 g, 2.2 mmol), DMF (6 mL) and isopropanol (2 mL) was mixed in a three-necked 50 mL round-bottom flask. The flask was evacuated followed by inlet of CO-gas (repeated three times, CO in water-byrett) before 1,3-bis (diphenylphosfino)propane (0.02 g, catalytic amount) and palladium(II)acetate (0.08 g, catalytic amount) was added.

The mixture was stirred at 80° C. for 7 h. The sovent was removed in vacuo and the residue was dissolved in diethyl ether, washed with $NH_3$ (2M) and dried ($MgSO_4$). The solvent was removed in vacuo to give a yellowish oily residue which was purified by flash chromatography (SiO$_2$, SC$_2$Cl$_2$/EtOAc, 10:1) to give the title compound in 66% yield (0.2 g). α(base)=–110.5° (MeOH, 0.1M, 22° C). the HCl-salt was precipitated from diethyl ether at 0° C. and recrystallized from EtOAc/diethyl ether. Mp 153°–155° C.

Example 59

(R)-3-(N-isopropyl,N-n-propylamino)5-(2-N-thiazoleaminocarbonyl)chroman (R)-5-Chlorocarbonyl,3-(N-isopropyl,N-n-propylamino) chroman (0.65 g, 2.3 mmol) and 2-aminothiazole (0.68, 6.8 mmol), dissolved in methylene chloride (50 mL), was stirred at room temperature for 2 h. The reaction mixture was washed with 1M NH$_3$ and dried (Na$_2$SO$_4$). Removal of solvent in vacuo gave a brownish oily residue which was purified by flash chromotagraphy (SiO$_2$, CH$_2$Cl$_2$/EtOAc, 10:1) to give the title compound in 43% yield (0.35 g). The HCl-salt was precipitated from diethyl ether at 0° C. and then recrystallized from EtOAc/diethyl ether. α(HCl-salt)= –20.0° C.). Sinters<140° C.

Example 60

(R)-3-(N-Isopropyl,N-n-propylamino)5-(3-pyridine)chroman (R)-3(N-isopropyl,N-n-propylamino)5-trifluoromethanesulfonyloxychroman (0.37 g, 0.96 mmol) was dissolved in toluene under a nitrogen atmosphere. Ethanol (7 mL), 2M Na$_2$CO$_3$ (3 mL), LiCl (0.08 g, 1.9 mmol) 3-pyridineboronic acid (0.7, 0.5 mmol) and finally Pd(PPh$_3$)$_4$ (0.04 g) was added and the reaction mixture was refluxed for 6 h. The solvent removed in vacuo until 10 mL was left. The residue was diluted with diethyl ether, washed with 2M NH$_3$ and dried (MgSO$_4$). Removal of the solvent gave yellowish oily residue which was purified by flash chromatography (SiO$_2$, CH$_2$Cl$_2$/EtOAc, 5:1) to give the title compound in 94% yield (0.28 g) α(base)=–47.6° (MeOH, 0.1M, 21° C.). The dioxalate was precipitated by addition of oxalic acid (2.2 eq), dissoved in diethyl ether, to a solution of the base in diethyl ether. Then salt was the recrystallized from EtOH/diethyl ether. Sinters <135° C.

Example 61

(R)-3-(N-Isopropyl,N-n-propylamino)-5-phenylchroman (R)-3-(N-Isopropyl,N-n-propylamino)-5-trifluoromethanesulfonyloxychroman (1 g, 2.6 mmol) was dissolved in toluene (25 mL) under a nitrogen atmosphere. Ethanol (11.5 mL), LiCl (0.22 g, 5.2 mmol), Na$_2$CO$_3$(2M, 3.8 mL), Pd(PPh$_3$)$_4$ (0.054 g, 0.047 mmol) and phenylboronic acid (0.38 g, 3.1 mmol) were added and the reaction mixture was stirred at 90° C. for 7 h. The solvent removed in vacuo until 15 mL was left. The residue was diluted with diethyl ether, washed with NH$_3$ (2M) twice and dried (MgSO$_4$). Removal of the solvent in vacuo gave a yellow-brownish oily residue which was purified by flash chromatography )SiO$_2$, CH$_2$Cl$_2$) to give the title compound in 86% yield (0.7 g). α=–50.7° (MeOH, 0.1M, 22° C.). The HCl-salt was precipitated from ether by the slow addition of HCl in ether to an ice-cold solution of the base. The crude salt was recrystallized from EtOAc/diethyl ether to give 650 mg of needle-like crystals. Mp. 141°–142° C.

Example 62

(R)-3-(N-isopropyl,N-n-propylamino)5-carbamoylchroman

A solution of (R)-5-chlorocabonyl,3-(N-isopropyl,N-n-propylamino)chroman (0.37 g, 1.3 mmol) in methylene chloride (30 mL) was carefully flushed with NH$_3$ for 30s. A white precipitate was immediately formed. The reaction mixture was then stirred for 30 min at room temperature before it was washed with water and dried (MgSO$_4$). The solvent was removed in vacuo to give a crude oil which was purified by flash chromatography (SiO$_2$, CH$_2$Cl$_2$/EtOAc; 10:1). The title compound was obtained in 58% yield (0.21 g ) as colourless crystals from diethyl ether/hexane.

α=–115.8°, MeHO, 0.1M, 21° C.). Mp. 120.6°–122° C. This compound is a very strong agonist.

Example 63

(R)-3-(N-isopropyl,N-n-propylamino)5-N-phenylaminocarbonylchroman (R)-5-chloracarbonyl,3-(N-isopropyl,N-n-propylamino) chroman (0.65 g, 2.3 mmol) and aniline (0.86 g, 9.2 mmol), dissolved in methylene chloride (30 mL), was stirred at room temperature for 1 h. The reaction mixture was then washed with 2M NH$_3$ and dried (Na$_2$SO$_4$). The solvent was removed in vacuo to give a brownish oily residue which was purified by flash chromatography (SiO$_2$, CH$_2$Cl$_2$/EtOAc, 5:1) to give the pure title compound in 91% yield (0.75 g). α(base=–91.3° (MeOH, 0.1M, 21° C.). The HCl-salt was precipitated from ether at 0° C. and then recrystallized from EtOAc/diethyl ether. Sinters <120° C.

Example 64

(R)-5-(2-Furyl)3-N-isopropyl,N-n-propylaminochroman (R)-3-(N-Isopropyl,N-n-propylamino)5-trifluoromethanesulfonyloxychroman (0.4 g, 1 mmol), 2-furylboronic acid (0.3 g, 2.6 mmol), LiCl (0.09 g, 2 mmol), NaCo$_3$ (2M, 3 mL), ethanol (7 mL) and toluene (15 mL) was mixed, under nitrogen, in a three necked 100 mL round bottom flask equipped with a condenser. Finally was Pd(PPh3) (0.03 g, catalytic amount) added and the reaction mixture was refluxed for 2 hours before it was diluted with diethyl ether, washed (2M NH$_3$) and dried (Na$_2$SO$_4$). The solvent was removed in vacuo to give a brownish oily residue which was purified by flash chromatography (SiO$_2$, CH$_2$Cl$_2$/EtOAc, 10:1) to give the pure title compound in 95% yield (0.3 g). α(base)=–57.4° (MeOH 0.1M, 21° C.). The HCl-salt was precipitated from diethyl ether at 0° C. and then recrystallized from EtOAc/diethyl ether. mp=151°–152° C.

Example 65

5-Formyl-3-(N-isopropyl-N-propylamino)chroman a) 5-Hydroxymethyl-3-(N-isopropyl-N-propylamino) chroman 5-Methyloxycarbonyl-3-(N-isopropyl-N-propylamino) chroman (0.69 g, 2.36 mmol) was dissolved in 25 mL of dry methylene chloride and cooled to –78° C. A 1M solution of diisobutylaluminum hydride in hexane (6.6 mL) was added dropwise and the reaction was allowed to warm to room temperature for 50 min. A 1M solution of KOH was added dropwise and then the reaction was put into the refrigerator over night. The solution was poured through a pad of Na$_2$SO$_4$, dried (Na$_2$SO$_4$), filtered and the solvent removed in vacuo to give 0.60 g (97% yield) of the title compound as a clear oil.

$^{13}$C NMR: (200 MHz—CDCl$_3$) PPM 154.6 140.1, 127.0, 120.5, 119.8, 116.3, 69.0, 62.9, 50.9, 48.9, 47.8, 27.2, 24.3, 21.0, 20.1, 11.7 b) 5-Formyl-3-(N-isopropyl-N-propylamino)chroman

5-Hydroxymethyl-3-(N-isopropyl-N-propylamino) chroman (0.60 g, 2.27 mmol) was dissolved in 50 mL methylene chloride and to the solution manganese dioxide (1.98 g, 22.7 mmol) was added in one portion and the reaction was allowed to stir at room temperature for 8 days.

The reaction was filtered through a pad of celite, washed with warm methylene chloride and the solvent was removed in vacuo.

Chromatography on silica (eluent: 5% EtOAc/hexane) gave 0.33 g (56% yield) of the title compound (base) as a slightly yellow oil.

$^{13}$C NMR: (200 MHz—CDCl$_3$) PPM 193.0, 155.1, 135.0, 127.0, 126.8, 124.0, 122.4, 69.2, 50.3, 48.9, 47.7, 28.1, 24.3, 21.1, 19.9, 11.6.

Example 66

(R)-3-(N-isobutyl)amino-5-(N-methyl)-carbamoylchroman

To a stirred solution of (R)-3-amino-5-(N-methyl)-carbamoylchroman in methanol (25 mL) isobutyraldehyde (0.33 g, 4.60 mmol) was added. The mixture was cooled to 0° C. and sodium cyanoborohydride (0.34 g, 5.44 mmol) was added in protions. pH was adjusted to approximately pH 5 with acetic acid. The mixture was stirred at room temperature for 3.5 hours. A small amount of isobutyraldehyde (15 mg, 0.21 mmol) was added due to incomplete reaction and the mixture was stirred for another 20 min. The solvent was evaporated and the residue was partitioned between ether (100 mL) and 1M NH$_3$-solution (20 mL). The layers were separated and the aquous phase was extracted with ether (3×50 mL). The combined organic layers were washed with 1M NH$_3$-solution (20 mL), dried (MgSO$_4$), filtered and evaporated. The residue was chromatographed on a short column of silica gel (eluent: EtOAc+0.5% conc. NH$_3$). Pure fractions were pooled and evaporated to give 0.81 g (74%) of the title compound as a white solid: mp 111°–112.8° C. [α]$^{21}$: −33.1 (c=2.6, MeOH).

Example 67

(R)-3-(N-isobutyl-N-propyl)amino-5-(N-methyl)-carbamoylchroman hydrochloride

Propionaldehyde (0.11 g; 131 µL, 1.82 mmol) was added to a stirred, ice cooled solution of (R)-3-(N-isobutyl)amino-5-(N-methyl)-carbamoylchroman (0.43 g, 1.65 mmol) in methanol(10 mL). Sodium cyanoborohydride (0.14 g, 2.15 mmol) was added in portions and pH was adjusted to pH 5 with acetic acid. The reaction mixture was stirred at room temperature. In order to complete the reaction several additions of propionaldehyde had to be done. Totally 0.20 g; 248 µL, 3.44 mmol was added to the reaction mixture.

The solvent was removed in vacuo and the residue was partitioned between ether (100 mL) and 1M NH$_3$-solution (20 mL). The layers were separated and the aquous layer was extracted with ether (50 mL). The combined organic layers were washed with brine (20 mL), dried (MgSO$_4$), filtered and evaporated. The crude product was filtered through a short column of silica gel (eluent: EtOAc: hexane 1:1+0.5% conc. NH$_3$). The eluent was removed in vacuo giving an uncoloured oil which was converted into the hydrochloride in HCl/ether:

Example 68

(R)-3-[N-(2-pyridyl)methyl]amino-5-(N-methyl)-carbamoylchroman (R)-3-amino-5-(N-methyl)-carbamoylchroman (1.02 g, 4.96 mmol) was dissolved in methanol (30 mL). The reaction vessel was coated with aluminium foil to prevent exponation to light. The solution was cooled to 0° C. and picolinaldehyde (0.69 g; 617 µL; 6.45 mmol) was added. Sodium cyanoborohydride (0.53 g, 8.44 g) was then added in portions and pH was adjusted to pH 5.5 with acetic acid.

The reaction mixture was stirred at room temperature for 2 hours. Another 50 µL, 0.52 mmol of picolinaldehyde was added in order to complete the reaction and the mixture was stirred for 1 hour. The solvent was removed in vacuo and the residue was partitioned between ether (100 mL) and 1M NH$_3$-solution (25 mL). The layers were separated and the aqueous layer was extracted with ether (2×50 mL). The combined ether extracts did not contain any reasonable amount of the desired product. Therefore, the aquous phase, with an addition of NaCl (s), was extracted with EtOAc (4×100 mL). The combined organic layers were dried (Na$_2$SO$_4$), filtered and evaporated to give a yellow solid. Recrystallisation from EtOAc: hexane (35:65) gave a white solid which had to be further purified by column chromatography (EtOAc:EtOH 1:1+1% conc. NH$_3$) yielding 0.64 g (43%) of the title compound as a white solid: mp 141.2°–141.6° C.; [α]$^{21}$=−26.2 (c=3.0, MeOH).

Example 69

(R)-3-(N-hexyl)amino-5-phenylchroman hydrochloride

To a solution of (R)-3-amino-5-phenylchroman (1.00 g, 4.44 mmol) in methanol (25 mL), hexanal (0.49 g; 0.60 mL, 4.91 mmol) was added while stirring. The mixture was cooled to 0° C. and sodium cyanoborohydride (0.36 g, 5.78 mmol) was added in portions. pH was adjusted to pH 5.5 with acetic acid. The reaction mixture was stirred at room temperature for 2.5 hours. Due to incomplete conversion of the starting material another 300 µL (2.46 mmol) of hexanal was added in portions. The solvent was removed under reduced pressure and the residue was partitioned between ether (100 mL) and 1M NH$_3$-solution (25 mL). The layers were separated and the ether extract was washed with 1M NH$_3$-solution (25 mL). The aquous phase was removed and the ether phase was shaken with 1M HCl-solution (10 mL). The hydrochloride salt crystallized directly in the separatory funnel and was filtered off and washed with ice cooled hexane. After drying there was obtained 0.86 g (56%) of the title compound as white crystals: mp 171.6°–174.2° C.; [α]$^{21}$=+82.8 (c=1,MeOH).

Example 70

(R)-3-(N-methyl-N-propyl)amino-5-phenylchroman.hydrochloride (R)-3-(N-propyl)amino-5-phenylchroman (0.46 g, 1.74 mmol) was dissolved in methanol (15 mL). Formaldehyde (0.70 g, 8.70 mmol) was added and the reaction vessel was cooled on an ice bath. Sodium cyanoborohydride (0.58 g, 9.23 mmol) was added in portions which after pH was adjusted to pH 6 with a few drops of conc. acetic acid. The reaction mixture was stirred at room temperature for 3 hours. The solvent was evaporated and the residue was partitioned between ether (50 mL) and 1M NH$_3$-solution (10 mL). The layers were separated and the aqueous phase was extracted with ether (50 mL). The combined organic layers were washed with 1M NH$_3$-solution (10 mL), dried (MgSO$_4$), filtered and evaporated. The residue was purified by column chromatography (eluent: hexane: EtOAc 70:30+0.1% conc. NH$_3$) yielding 0.40 g (81%) of the corresponding base of the title compound as an uncoloured oil which solidified upon standing: $[\alpha]^{21}=-35.9$ (c=1.0, MeOH). Conversion to the hydrochloride was done in HCl/ether giving 0.4 g (total yield: 75%) of the title compound Mp 162°–164° C.

Example 71

(R)-3-[N-2-(2-thienyl)ethyl]amino-5-phenylchroman hydrochloride

To a solution of (R)-3-amino-5-phenylchroman (0.41 g, 1.83 mmol) in dry DMF (2.0 mL) were added $K_2CO_3$ (0.28 g, 2.02 mmol) and 2-(2-thienyl)ethyl bromide (0.36 g, 1.80 mmol). The reaction mixture was stirred under $N_2$ at 65° C. for 6 hours. The solvent was removed in vacuo and the residue was partitioned between ether (50 mL) and 1M $NH_3$-solution (10 mL). The layers were separated and the aqueous phase was saturated with NaCl (s) and extracted with an additional amount of ether (25 mL). The organic layers were combined, dried ($MgSO_4$), filtered and concentrated. The residue was purified by column chromatography (eluent: hexane: EtOAc 65:35+0.2% conc. $NH_3$) giving 0.19 g (31%) of the corresponding base of the title compound as a light yellow oil: $[\alpha]^{21}=+8.2$ (c=1.0, MeOH). Conversion to the hydrochloride was done in HCl/ether giving 0.20 g (total yield: 29%) of the title compound: mp 191.6°–193.2° C.

Example 72

3-Dipropylamino-8-fluoro-5-trifluoromethanesulfonyloxychroman a) 2-Fluoro-5-methoxybenzoic acid The title compound was prepared according to a method reported by Hay and Blanchard [*Canad. J. Chem.* 43, 1306 (1965)]. In a three-necked round-bottom flask (1000 mL), equipped with a magnetic stirrer, thermometer, reflux condensor and a gas distribution tube, cobalt(II)acetate tetrahydrate (12.6 g; 51 mmol) was dissolved in glacial acetic acid (404 mL) by stirring. Commercial 4-fluoro-3-methylanisole (35.4, 252 mmol) and 33% HBr in acetic acid (10.1 mL; 51 mmol) were added and then the mixture was heated on an oil-bath to 90°–95° C. All the time a stream of oxygen was passed through the solution at a rate of about 660 mL/min. After 3 hours the reaction mixture was cooled to room temperature and then rotary evaporated to dryness.

The violet colored solid thus obtained was transferred to an Erlen-Meyer flask, dissolved in boiling water (350 mL) containing concentrated hydrochloric acid (5–10 mL) and then allowed to crystallize at a cold place over night. The crude acid was filtered off by suction, washed with small portions of ice-water until the washing were pale yellow, dissolved in 2M NaOH (120 mL) and washed with toluene (2×100 mL). The organic extracts were discarded. The aqeous phase was suction filtered, cooled in a beaker on an ice-bath and carefully acidified with concentrated hydrochloric acid until all the acid was precipitated. The contents in the beaker was heated to the boiling oint whereby most of the acid dissolved. The solution was cooled at room temperature and finally in the refrigerator. The mother liquor was sucked off. The crystal mass was washed with ice-water (3×50 mL) and then dried in a vacuum-oven at 40° C. to give 31.5 g of the title compound as a grey-white solid. Mp. 146°–148° C.

b) 2-Fluoro-5-methoxybenzamide

In a three-necked round-bottom flask (500 mL), equipped with a magnetic stirrer and a reflux condensor, 2-fluoro-5-methoxybensonic acid (33.8 g; 199 mmol) and thionyl chloride (200 mL) were refluxed under nitrogen for 2 h. The excess of thionyl chloride was evaporated to leave an oily residue which was dissolved in methylene chloride (100 mL) and evaporated. This procedure was repeated three times. The crude acid chloride thus obtained was dissolved in methylene chloride (100 mL) and added dropwise during 10 min to a cold (–40° to –50° C.) and mechanically stirred solution of dry THF (300 mL) and liquid ammonia (100 mL) in a three-necked round-bottom flask (1000 mL) under nitrogen. When the addition was completed the cooling bath was taken away and the mixture was slowly warmed to room temperature while the stirring was continued. Water (50 mL) was added to dissolve the precipitated salt and the two-phase solution obtained was concentrated to dryness by rotary-evaporation. The crude amide was washed repeatedly with small portions of dilute aqueous ammonia followed by water until the washings were colourless. Drying at reduced pressure over night afforded 32.0 g of the title compound as light-brown crystals. Mp. 122°–124° C.

c) 2-Fluoro-5-methoxyaniline

In a round-bottom flask (500 mL), equipped with a reflux condenser and a magnetic stirrer, bromine (11.4 mL; 223 mmol) was added dropwise to a cold (+4° C.) and stirred solution of sodium hydroxide (35.5 g; 887 mmol) and water (322 mL). Then 2-fluoro-5-methoxybenzamide (31.9 g; 189 mmol) was added in portions. The mixture was heated on an oil-bath, refluxed for 1 h, cooled to room temperature and extracted with ether (3×300 mL). Drying the combined ether phases ($K_2CO_3$), filtering, evaporation of the solvent and vacuum distillation of the oily residue afforded 20.1 g of the title compound as a pale yellow oil (bp. 113°–114° C. /14 mmHg), which solidified in the cold (Mp. 27°–28° C.).

d) 2-Fluoro-5-methoxyphenol

The method used to prepare the phenol is basically the procedure reported by Claudi et. al. [*med. Chem.* 33, 2408–2412 (1990) with modification according to Lambooy [*J. Amer. Chem. Soc.* 72, 5327–5328 (1950)]. In a three-necked round-bottom flask (1000 mL), equipped with dropping-funnel and a magnetic stirrer, 2-fluoromethoxyaniline (11.3 g, 80 mmol ), concentrated sulfuric acid (35 mL) and water (200 mL) were mixed and then cooled to 3°–5° C. A solution of sodium nitrite (6.07 g; 88 mmol) in water (20 mL) was added dropwise to the stirred mixture above at 2°–4° C. When the addition was completed the solution was stirred for five minutes and then urea (0.48 g) was added followed by water (100 mL). Meanwhile an apparatus was prepared consisting of a three-necked round-bottom flask (1000 mL), a thermometer, an electrical heating mantle, a steam distillation apparatus, and long (40 cm) water-jacketed condensor on top of which a 500 mL dropping funnel was attached. In the flask $CuSO_4 \times 5H_2O$ (56 g), concentrated sulfuric acid (160 mL) and water (160 mL) were placed. The mixture was heated to 150° C., the diazonium salt solution, cooled all the time by adding small chunks of the ice to it, was added dropwise from the dropping funnel, and a current of steam was passed through the system to remove the phenol. The distillate was extracted with ether (3×400 mL) and the combined ether extracts were dried ($MgSO_4$), filtered and concentrated in vacuo. The crude phenol was purified on a silica column eluted with ether/n-hexane (15:85) to afford 4.03 g of the title compound as a crystalline solid. Mp. 25°–26° C.

e) 3-Cyano-8-fluoro-5-methoxy-2-H-chromen

The synthesis of the title compound is based on a method reported by Thorberg et. al. in *Acta Chem Scand.* 24, 169–182 (1987). Trichloroacetic acid (approx. 0.04 g) was added to a stirred solution of 2-fluoro-5-methoxyphenol (6.8 g, 48 mmol) and ethyl vinyl ether (9.1 mL, 95 mmol) under nitrogen in a round-bottom flask (50 mL) at +4° C. The mixture was stirred at room temperature over night. Excess ethyl vinyl ether was rotary-evaporated and the residue dissolved in ether (100 mL). The ether solution was washed with saturated $Na_2CO_3$ (2×5 mL), dried $K_2CO_3$), filtered and concentrated in vacuo. The oily residue was dissolved in dry toluene (100 mL) and the solution was concentrated, first using a rotary-evaporator and then a vacuum-pump (0.1 mmHg), to afford 10.0 g of the protected phenol as yellow oil. In a dry three-necked round-bottom flask (100 mL), equipped with a magnetic stirrer and a rubber septum, 8.8 g (41 mmol) of the protected phenol form above was dissolved in dry THF (30 ML) under nitrogen. The solution was cooled to −25° C. on a dry ice-bath. Then 1.6M. n-BuLi in hexane (32 mL; 51 mmol) was added dropwise with a syringe to the stirred solution duting 15 min. When the addition was completed the mixture was warmed to −15° C. In 1 h, then cooled to −20° C. Dry dimethylformamide (4.7 mL; 60 mmol) was added dropwise during 5 min while the temperature was kept at −25° to −20° C. (the reaction is exothermic). When the addition was completed the solution was warmed to −5° C. In 2 hours and then poured in ice-cold 2M hydrochloric acid (200 mL). After stirring for 40 min the hydrolysis was complete as seen from TLC. The resulting mixture was washed with ether (3×250 mL). The combined ether phases were dried ($MgSO_4$), filtered and concentrated in vacuo. The yellow solid residue was dissolved in ether (50 mL) and concentrated to afford 7.12 g of crude 3-fluoro-2-hydroxy-6-methoxybenzaldehyde as a yellow crystalline solid.

Crude 3-fluoro-hydroxy-6-methoxybenzaldehyde (8.0 g) from above, acrylonitrile (13 mL; 193 mmol) and 1,4-diazadicyclo [2,2,2] octane (0.66 g; 5.9 mmol) were refluxed in a three-necked round-bottom flask (50 mL) under nitrogen for 4 h. Rotary-evaporation of the volatiles left a thick, red oil which was flash-chromatographed on a silica column eluted with methylene chloride/n-hexane (4:5). Concentration of relevant fractions gave an impure product (91% GC) which was crystallized form EtOAc to give 1.31 g of the title compound as colourless bars. Mp. 133°–135° C.

f) 8-Fluoro-5-methoxychroman-3-yl carboxylic acid

3-Cyano-8-fluoro-5-methoxy-2-H-chromen (1.23 g; 6.0 mmol) and 2M sodium hydroxide solution (25 mL) were refluxed under nitrogen for 7.5 hours and then stirred at room temperature over night. Excess concentrated hydrochloric acid was added to the solution with stirring. After cooling the slurry on an ice-bath, the precipitated carboxylic acid was sucked dry, transferred to a 250 mL hydrogenation flask (Parr) and dissolved in glacial acetic acid (110 mL). Palladium (5%) on activated carbon (0.104 g was added. Hydrogenation in a Parr-apparatus at 1 atm hydrogen pressure and 40°–50° C. (IR-lamp) for 10 hours completed reaction. The suspension was filtered through Celite and filtrate was concentrated in vacuo. The residue was dissolved in toluene (25 mL) and the solution was concentrated by rotary-evaporation. This procedure was repeated once. Evaporation with vacuum pump (0.05 mmHg) afforded 1.12 g of the title compound as grey-white solid. Mp. 140°–145° C. (decomp).

g) 8-Fluoro-5-methoxychroman-3-y-carbamic acid benzyl ester

8-Fluoro-5-methoxychroman-3-yl carboxylic acid (1.12 g; 85.0 mmol), diphenyl phosphoryl azide (1.3 mL; 5.9 mmol) and toluene (10 mL) were mixed in a three-necked round-bottom flask (50 mL) under nitrogen. Triethylamine (0.83 mL; 5.9 mmol) was added and clear solution was stirred at 100° for 2 h. Benzylalcohol (0.61 mL; 5.9 mmol) was added in one portion and the stirring continued at 90° C. for 17 h. The volatiles were evaporated and the residue was taken up in toluene (25 mL). After Washing with 10% acetic acid (1×30 mL) and 2M ammonia (1×30 mL) the solution was dried ($MgSO_4$), filtered and concentrated in vacuo to give a brown oil. Flash-chromatography of the crude product on a silica column eluted with ethyl acetate/toluene (3:97) afforded compound as an oil (contaminated with 2% unreacted isocyanate according to GC).

h) 3-Amino-8-fluoro-5-methoxychroman

8-Fluoro-5-methoxychroman-3-yl carbamic acid benzyl ester (1.37 g; 4.0 mmol), absolute ethanol (90 mL), glacial acetic acid (10 mL) and 5% palladium on activated carbon (0.090 g) were mixed in a 250 mL hydrogenation flask (Parr). Hydrogenation in a Parr-apparatus at 1 atm hydrogen pressure and 45° C. (IR-lamp) over night completed the reaction (hydrogen uptake of 80 mL at 20° C.). The suspension was filtered through Celite and the filtrate was concentrated by rotary-evaporation. The residue was dissolved in toluene (25 mL) and concentrated again. This procedure was repeated once. Evaporation with a vacuum pump (0.05 mmHg) gave 1.20 g of a wet crystal mass consisting mainly (93% GC) of the title compound (as the acetate).

i) 3-Dipropylamino-8-fluoro-5-methoxychroman

In a round-bottom flask equipped with a magnetic stirrer were placed the crude acetate of 3-amino-8-fluoro-5-methoxychroman (1.18 g; approx. 3.9 mmol) from above, dry methanol (10 mL), propanal (2.8 mL; 39 mmol), glacial acid (pH 3–4) and sodium boronhydride (0.25 g; 3.9 mmol) but with no molecular sieves. The reaction mixture was stirred under nitrogen at room temperature for 1 h. The solution was filtered through Celite and the solvent was evaporated to leave a liquid residue which, was diluted with water (25 mL) and extracted with ether (2×100 mL) after adjusting pH to 10–11 with 5M sodium hydroxide. The collected ether phases were dried ($K_2CO_3$), filtered and concentrated in vacuo.

Flash-chromatography of the crude on a silica column eluted with ethyl acetate (2% and 10%) in n-hexane afforded 0.235 g of the title compound as a colourless oil.

j) 3-Diproprylamino-8-fluoro-5-hydroxychroman hydrochloride

The hydrochloride salt of 3-dipropylamino-8-fluoro-5-methoxychroman was prepared by adding an excess of hydrochloride in ether to a stirred and cooled (+4° C.) solution of the base (0.235 g; 0.84 mmol) in ether (10 mL), then isolating the precipitated salt and drying it in a vacuum-oven at 50°.

In a three-necked round-bottom flask (25 mL) equipped with a magnetic stirrer and a rubber septum the salt from above was dissolved in methylene chloride (7 mL) under nitrogen. The solution was cooled on a dry ice-bath to −40° C., then boron tribromide (0.158; 1.7 mol) in methylene chloride (1 mL) was added slowly with syringe to the stirred solution. When the addition was completed (2 min) the temperature of the solution was slowly raised to +4° C. and kept at that temperature with an ice-bath. After a total reaction time of 7 hours the solution was poured in saturated sodium hydrogen carbonate (20 mL). The mixture was extracted with ether (3×30 mL) and the collected ether phases was washed with brine, dried ($Na_2SO_4$), filtered and concentrated in vacuo. Flash-chromatography of the crude product on a silica column eluted with ethyl acetate/n-hexane (15:85) afforded 0.195 g of 3-dipropylamino-8-fluoro-5-hydroxychroman as an oil.

The title compound was prepared by precipitating the base with an excess of hydrochloride in ether and drying the salt thus obtained in a vacuum-oven at 50° C. for 5 h. Yield 0.220 g (99% form the base), with white aomorphus solid. Mp. 190°–192° C.

k) 3-Dipropylamino-8-fluoro-5-trifluoromethane sulfonyloxychroman

In a dry three-necked round-bottom flask (25 mL) equipped with a magnetic stirrer and a rubber septum 3-dipropylamino-8-fluoro-5-hydroxychroman hydrochloride (0.211 g; 0.70 mmol), 2,4,6-collidine (0.110 mL; 0.84 mmol) and methylene chloride (7.3 mL) were mixed under nitrogen. The clear solution was cooled to −40° C. on a dry ice-bath, then trifluoromethanesulfonic anhydride (0.230 mL; 1.37 mmol) in methylene chloride (0.3 mL) was added slowly (5 min) to the stirred mixture with a syringe. When the addition was completed the solution was stirred for 1 hour (the temperature increased to 0° C.), then poured in cold (+4° C.) saturated sodium hydrogen carbonate (20 mL) and extracted with ether (2×40 mL). The collected ether phases were washed with water (1×30 mL), dried ($Na_2SO_4$), filtered and concentrated by in vacuo. The crude product was flash-chromatographed on a silica column with ethyl acetate/n-hexane (1:19) to afford 0.213 g of the title compound as an oil.

Example 73

3-Dipropylamino-8-fluoro-5-(2-furyl)chroman hydrochloride

In a three-necked round-bottom flask (25 mL) equipped with a magnetic stirrer and a reflux condensor the following reagents were mixed under nitrogen: 3-dipropylamino-8-fluoro-5-trifluoromethanesulfonylchroman (0.104 g; 0.25 mmol), absolute ethanol (1.7 mL), toluene (3.6 mL), 2-furylboronic acid (0.071 g; 0.64 mmol), lithium chloride (0.022 g; 0.51 mmol), 2M sodium carbonate (0.7 mL) and tetrakis(triphenylphosphine)palladium(0) (0.0073 g). The mixture was heated on an oil-bath to a reflux temperature (75°–80° C.). After 3 hours GC-analysis indicated a partial reaction (20% product and 66% starting material). Therefore more 2-furylboronic acid (0.031 g; 0.28 mmol), absolute ethanol (0.2 mL) and tetrakis(triphenylphosphine)-palladium(0) (0.009 g) were added. The mixture was stirred at 75°–80° C. over night, then poured in 2M ammonia (40 mL) and extracted with ether (2×40 mL). The collected ether phases were dried ($Na_2SO_4$), filtered and concentrated in vacuo. The crude product was purified by flash-chromatography on a silica column with ethyl acetate/n-hexane (2:98). Relevant fractions were pooled and concentrated to give an oil consisting of impure product (72% GC). This material was purified in a second run by flash-chromatography on a silica column eluted with eluted with ethyl acetate/methylene chloride (1:99) to give 0.042 g (51% yield) of 3-dipropylamino-8-fluoro-5-(2-furyl)chroman as an oil.

The title compound was prepared from the base as described for 3-dipropylamino-8-fluoro-5-hydroxychroman hydrochloride above. White crystalline solid. Mp. 162°–164° C.

Example 74

3-Dipropylamino-8-fluoro-5-N-isopropylcarbamoylchroman hydrochloride

In a three-necked round-bottom flask (25 mL), equipped with a magnetic stirrer and an inlet for carbon monoxide from a hydrogenation burette, dioxane (1.3 mL), 3-dipropylamino-8-fluoro-5-trifluoromethanesulfonyloxychroman (Example 63 k) 0.110 g; 0.20 mmol) and isopropylamine (0.118 mL; 1.4 mmol) were mixed. The flask was evacuated and the filled with carbon monoxide. This procedure was repeated twice. 1,3-Bis(diphenylphosphino)propane (0.0032 g) and palladium (II)acetate (0.0016 g) were added and then the mixture was stirred at 75° C. under an atmosphere of carbon monoxide at 1 atm. GC-analysis showed that the reaction was unexpectedly slow. Stirring over night did improve the yield of desired product (59% GC) but still much triflate was left (27% GC). Accordingly, more 1,3-bis(diphenyl)phosphino) propane (0:0065 g) and palladium acetate (0.0032 g) were added. Unfortunately, stirring over night did not improve the yield but rather resulted in some decomposition of the product as seen from GC. At this point the reaction was worked up by adding saturated sodium hydrogen carbonate (5 mL) and extracting the mixture with ethyl acetate (2×10 mL). The combined organic phases were dried ($Na_2SO_4$), filtered and concentrated in vacuo. The crude product was flash-chromatographed on a silica column eluted with ethyl acetate (15 and 33%) in n-hexane to afford 0.021 g of starting material (triflate) and 0.030 g (40% yield based on recovered triflate) of 3-dipropylamino-8-fluoro-5-N-isopropylcarbamoylchroman as an oil.

The title compound was prepared from the base as described for 3-dipropylamino-8-fluoro-5-hydroxychroman hydrochloride above. White solid. Mp. (70 eV); m/z (rel.int.), 337(4.4, M+1), 336(17,M), 308(21), 307(100), 236(36), 194(6), 177(6), 43(19).

Example 75

(R)-8-Fluoro-3-(N-isopropyl-N-propylamino)-5-trifluoromethanesulfonylchroman (R)-8-Fluoro-3-(N-isopropyl-N-propylamino)-5-hydroxychroman (0.71 g, 2.66 mmol) and collidine (0.49 mL, 3.72 mmol) were dissolved in 25 mL of $CH_2Cl_2$ and cooled to −40° C. Trifluoromethanesulfonic anhydride (0.54 mL, 3.2 mmol) was added dropwise and allowed to warm to ambient temperature, and after coming to 0° C. the reaction was done.

The reaction was diluted with $CH_2Cl_2$ and washed with saturated $NaHCO_3$, dried ($Na_2SO_4$), filtered, and evaporated in vacuo to give crude.

Chromatography on silica (eluent: $CH_2Cl_2$) gave 0.82 g (77% yield) of the title compound as a clear oil. $[\alpha]^{21}$ −81.5° (C=0.1, $CHCl_3$).

Example 76

(R)-5-Acetyl-8-fluoro-3-(N-isopropyl-N-propylamino)chroman Hydrochloride (R)-8-Fluoro-3-(N-isopropyl-N-propylamino)-5-trifluoromethanesulfonylchroman (403 mg, 1.01 mmol) was dissolved in 3 mL DMF and then triethylamine (0.28 mL, 2.02 mmol), butyl vinyl ether (0.78 mL, 6.06 mmol), palladium acetate (7 mg), and 1,3-bis-diphenylphospinopropane (14 mg) were added. The resulting mixture was heated to 80°–90° C. with stirring for 3.5 h.

The solution was cooled and 5 mL of a 2M HCl solution was added and the reaction was stirred at room temperature for 1 h.

The mixture was diluted with ether and washed with a 2M $NH_3$ solution. The aqueous phase was re-axtracted with ether and the combined ether phases were treated with brine, dried (MgSO$_4$), filtered, and evaporated in vacuo to give a brown orange oil as crude.

Chromatography on silica (eluent: 15% EtOAc/hexane) gave 201 mg as a yellow oil (68% yield). $[\alpha]^{21}$ −165.1 (C=0.1, CHCl$_3$).

The HCl salt was precipitated from ether and recrystallized from EtOAc/ether to give a white solid Mp 148° C.

Example 77

(R)-5-Phenyl-8-fluoro-3-(N-isopropyl-N-propylamino)chroman Hydrochloride

To a solution of (R)-8-fluoro-3-(N-isopropyl-N-propylamino)-5-trifluoromethanesulfonylchroman (0.58 g, 1.45 mmol), ethanol (7 mL), lithium chloride (124 mg, 2.9 mmol), 2M sodium carbonate (2.2 mL), and tetradis (triphenylphosphine)palladium(0) (31 mg, 0.026 mmol) dissolved in toluene (15 mL) was phenylboronic acid (0.22 g, 1.74 mmol) added in one portion under nitrogen. The resulting solution was heated to 95° C. for 5 hours then the reaction was allowed to cool. The reaction was filtered and the solvent was evaporated in vacuo. The remains were taken into ether, washed with 2M NH$_3$, treated with brine and dried (MgSO$_4$). Removal of the solvent in vacuo gave the crude compound.

Chromatography on silica (eluent: CH$_2$Cl$_2$+CH$_2$Cl$_2$+NH$_3$) gave 0.42 g (89% yield) of the title compound (base) as an oil. $[\alpha]^{21}$ −45.0 (C=0.1, CHCl$_3$).

The hydrochloride salt was made by dissolving the pure base in ether and dropping an excess of an ethereal HCl to give a white solid. Mp 202°–203° C.

Example 78

(R)-5-[Carbonyl(2,6-dimethylphenyl)]-8-fluoro-3-(N,N-dipropylamino)chroman Hydrochloride 2-Bromo-m-xylene (0.5 mL, 3.6 mmol) was dissolved in 4 mL anhydrous THF under nitrogen atmosphere and cooled to −78° C. n-Butyllithium (1.6M in hexane, 2.0 mL, 3.2 mmol) was added dropwise and the reaction was allowed to stir at −78° C. for 1 hour. (R)-8-Fluoro-5-formyl-3-(N,N-dipropylamino)-chroman (0.30 g, 1.07 mmol) was dissolved in 5 mL anhydrous THF and added dropwise to the reaction mixture and then allowed to stir at −78° C. for 1 hour. The reaction was quenched by adding 2 mL H$_2$O and the reaction was allowed to warm to room-temperature. The solvent was removed in vacuo, the remains were taken into a 2M solution of NH$_3$ and then extracted thrice with ether. The combined ether portions were treated with brine, dried (MgSO$_4$), filtered, and the solvent removed in vacuo to give the crude alcohol as a white solid. A stream of nitrogen was gently allowed to blow on the crude solid overnight to remove the excess 2-bromo-m-xylene. The crude alcohol was oxidized directly in the next reaction without further purification.

Oxalyl chloride (122 µL, 1.4 mmol) was dissolved in 5 mL anhydrous CH$_2$Cl$_2$ under nitrogen atmosphere and cooled to −78° C. DMSO (0.24 mL, 3.4 mmol) was added under 5 min then the reaction was allowed to stir at −78° C. for 5 min. The crude alcohol (from above) was dissolved in 10 mL anhydrous CH$_2$Cl$_2$ and was added under 10 min to the reaction. After stirring at −78° C. for 25 min, triethylamine (0.75 mL, 5.4 mmol) was added and after 5 min the reaction was allowed to warm to room-temperature. H$_2$O/2M solution of NH$_3$ was added to the reaction and extracted thrice with CH$_2$Cl$_2$. The combined CH$_2$Cl$_2$ portions were dried (MgSO$_4$), filtered, and the solvent removed in vacuo to give the crude ketone. Chromatography on silica (eluent: 8.7% EtOAc/hexane) gave 345 mg (84% yield) of the title compound as a slightly yellow oil. $[\alpha]_D^{21}$ −57.0° (c 0.1, CHCl$_3$). Mass spectrum (70 eV) m/z (relative intensity) 383(56M+), 354(100), 283(26), 355(36).

The hydrochloride salt was made by dissolving the pure base in ether and dropping an excess of an ethereal HCl. The salt was dried in a vacuum oven at 50° C. to give a white solid as a hemi-hydrate which sinters at 80° C.

Example 79

(R)-8-Fluoro-3-(N-isopropyl,N-n-propylamino)-5-(5-oxazolyl)chroman Hydrochloride (R)-8-Fluoro-5-formyl-3-(N-isopropyl,N-n-propylamino) chroman (0.48 g, 1.7 mmol), tosylmethylisocyanide (0.37 g, 1.9 mmol) and K$_2$CO$_3$ (0.28 g, 2.0 mmol) were suspended in methanol (50 mL, dried 3 Å) under nitrogenatmosphere. The reaction mixture was refluxed for 1 hour. Diethyl ether and 2M NH$_3$ were added. The layers were separated and the water phase was extracted twice with diethyl ether. The organic layers were combined and dried (Na$_2$SO$_4$). The solvent was removed in vacuo to give a colorless oily residue which was purified by flash chromatography (SiO$_2$, CH$_2$Cl$_2$/EtOAc, 10:1) to give the title compound in 60% yield (320 mg). $[\alpha]_D^{22}$ −55° (c 5 mg/mL, MeOH). Mass spectrum (70 eV) m/z (relative intensity) 318(14,M+), 303 (20), 290(12), 289(81), 191(11), 149(12), 112(17), 85(23), 70(20), 56(20), 44(16), 43(100), 42(24), 41(58), 30(11). The HCl salt was precipitated from diethyl ether and sinters from 80° C.

Example 80

(R)-8-Fluoro-5-methoxycarbonyl-3-(N,N-di-n-propylamino)chroman (R)-8-Fluoro-3-(N,N-di-n-propylamino)-5-trifloromethanesulfonyloxychroman (0.95 g, 2.4 mmol), triethylamine (0.53 g, 5.2 mmol), 1,3-bis(diphenylphosphino) propane (100 mg, catalytic amount), palladium(II)acetate (50 mg, catalytic amount) and DMF/MeOH (18 mL, 6:2) were mixed in a 50 mL three necked round bottom flask. The flask was evacuated followed by the inlet of CO (repeated three times). The reaction mixture was stirred at 70° C. for 7 hours. The solvent was removed in vacuo and the residue was dissolved in diethyl ether/2M NH$_3$. The layers were separated and the water phase was extracted once with ether. The combined ether layers were dried (MgSO$_4$) and the solvent was removed in vacuo to give a brown oily residue which was purified by flash chromatography (SiO$_2$, CH$_2$Cl$_2$/EtOAC, 20:1) to give 650 mg of the title compound as a clear oil (87% yield). $[\alpha]_D^{21}$ −92° (c 10 mg/mL MeOH) Mass spectrum (70 eV) m/Z (relative intensity) 309(20, M+), 281(18), 280(100), 56(10), 43(22), 42(12), 41(16).

Example 81

(R)-8-Fluoro-5-formyl-3-(N,N-di-n-propylamino) chroman (R)-8-Fluoro-5-methoxycarbonyl-3-(N,N-di-n-propylamino)chroman (0.65 g, 2.1 mmol) was dissolved in THF (30 mL, sodium dried) under nitrogen atmosphere. The solution was cooled to −78° C. before diisobutylaluminium hydride (DIBAL-H, 1.0M, 8.4 mL, 8.4 mmol) was added under 10 min. The cooling bath was removed and the temperature of the reaction mixture was allowed to slowly raise to r.t. (20° C.). The reaction mixture was stirred for 3 hours before the reaction was quenched by the addition of 2M NaOH (2 mL). Saturated sodium tartrate and diethyl ether were added and the mixture was stirred until the "gel" dissolved. The layers were separated and the water phase was extracted twice with ether. The combined organic layers were dried ($MgSO_4$) and the solvent was removed in vacuo to give the alcohol.

Oxalyl chloride (0.30 g, 2.3 mmol) was dissolved in $CH_2Cl_2$ under nitrogen atmosphere. The solution was cooled to −78° C. before DMSO (0.4 g, 5.0 mmol) was added dropwise under 5 min. After stirring for 5 min, the alcohol, dissolved in $CH_2Cl_2$, was added under a 30 min period. The reaction mixture was stirred for 30 min before triethylamine (1.1 g, 10.5 mmol) was added under a 5 minutes perion. The stirring was continued. After 130 minutes the cooling bath was removed and the reaction mixture was slowly warmed ut to r.t. and then stirred for an additional 30 min before $NaHCO_3$ was added. The layers were separated and the water phase was extracted twice with ether. The combined organic layers were dried ($MgSO_4$) and the solvent was removed in vacuo to give an oily residue which was purified by flash chromatography ($SiO_2$, $CH_2Cl_2$/EtOAc, 20:1) to give 350 mg of the title compound (60% yield). $[\alpha]_D^{21}$ −86° (c 10 mg/mL MeOH). Mass spectrum (70 eV) m/z (relative intensity) 279(5, M+), 250(56), 179(48), 151(13), 149(10), 123(31), 103(28), 98(24), 77(11), 72(26), 70(44), 57(15), 56(54), 55(18), 54(16), 44(11), 43(100), 42(64), 41(79).

Example 82

(R)-5-[Carbonyl-(3,5-dimethylisoxazole)]-8-fluoro-3-(N,N-di-n-propylamino)chroman Hydrochloride 4-Bromo-3,5-dimethylisoxazole (1.9 g, 10.7 mmol) was dissolved n THF (20 mL, sodium dried) under a nitrogen atmosphere. The solution was cooled to −90° C. before n-butyllithium (1.6M in hexane, 9.7 mL, 9.7 mmol) was added under 10 min. The reaction mixture was stirred for 15 min before (R)-8-fluoro-5-formyl-3-(N,N-di-n-propylamino)chroman (0.6 g, 2.2 mmol), dissolved in THF (10 mL), was added under a 10 min period. The reaction mixture was stirred at −90° C. for an additional 20 min and then at −78° C. for 15 min before it was quenched by the addition of $NH_4Cl$. Diethyl ether and 2M $NH_3$ were added. The layers were separated and the water phase was extracted once with ether. The combined organic layers were dried ($Na_2SO_4$). The solvent was removed in vacuo to give a yellow oily residue which was flushed overnight with a nitrogen stream. Oxalyl chloride (0.28 g, 2,2 mmol) was dissolved in $CH_2Cl_2$ under a nitrogen atmosphere. The solution was cooled to −78° C.

DMSO 0.38 g, 4.8 mmol) was added dropwise under a 5 min period. The reaction mixture was stirred for 20 minutes before the crude alcohol, dissolved in $CH_2Cl_2$ was added under 15 min. The reaction mixture was stirred for 30 min. Triethylamine (1.01 g, 10 mmol) was added. The stirring was continued for 1 hour before the cooling bath was removed and the reaction mixture was allowed to warm to r.t. (21° C.). Diethyl ether and $NaHCO_3$ were added. The layers were separated and the water-phase was extracted once with ether. The combined organic layers were dried ($Na_2SO_4$) and the solvent was removed in vacuo to give a yellow oily residue which was purified by flash chromatography ($SiO_2$, $CH_2Cl_2$/hexane/EtOAc, 10:10:1) to give 340 mg of the title compound (42% yield). Mass spectrum (70 eV) m/z (relative intensity) 374(11,M+), 346(21), 345(100), 274(15), 43(11). The HCl-salt was precipitated from diethyl ether at 0° C. and then recrystallized from $CH_2Cl_2$/diethyl ether. mp 202°–205° C.

Example 83

(R)-5-N-Morpholinyl-3-(N-isopropyl-N-n-propylamino)chroman Hydrochloride

Diglycolic acid (0.15 g, 1.1 mmol) and N,N-carbonyldiimidazole (CDI, 0.28 g, 1.8 mmol) were dissolved in THF (dried over sodium) under nitrogen atmosphere. The mixture was refluxed for 15 min before (R)-5-amino-3-(N-isopropyl-N-n-propylamino)chroman (NAE 277) (0.2 g, 0.8 mmol) was added. The refluxing was continued for 18 hours. The reaction mixture was then combined with a similar reaction mixture from an identical reaction (starting from 0.1 g of the aniline). Diethyl ether and 2M $NH_3$ were added. The layers were separated and the water phase wase extracted once with ether. The combined organic layers were dried ($Na_2SO_4$) and the solvent was removed in vacuo to give an ioly residue. The residue was dissolved in diethyl ether under nitrogen atmosphere. Lithium aluminium hydride (0.23 g, 6 mmol) was added and the mixture was refluxed for 18 hours. Water (0.3 mL) followed by 0.3 mL of 15% NaOH and finally 1 mL of water was added under vigorous stirring.

The solution was decanted from the white solid residue and the residue was washed twice with ether. The organic layers were combined and the solvent was removed in vacuo to give the crude residue which was purified by flash chromatography ($SiO_2$, $CH_2Cl_2$/EtOAc, 5:1, also containing 0.5% of $NH_3$) to give 180 mg of the title compound (47% yield). $[\alpha]_D^{21}$ −39° (c 5 mg/mL MeOH). Mass spectrum (70 eV) m/z (relative intensity) 318(8,M+), 133(14), 130(13), 117(10), 114(32), 112(45), 85(28), 43(100), 42(27), 41(44), 39(23). The HCl salt was precipitated from diethyl ether and recrystallized from EtOAc/diethyl. The crystalls sinters from 70° C.

Example 84

(R)-5-Carbamoyl-2-aminochroman a) (R)-5-Carbamoyl-2-N-Trifluoroacetylaminochroman (R)-2-N-Trifluoroacetylamino-5-trifluoromethanesulfonyloxychroman (2.0 g, 5.0 mmol) was dissolved in DMF (20 mL) in a three necked roundbottom flask. The flask was evacuated followed by inlet of CO-gas (repeated three times). 1,3-Bis(diphenylphosphino)-propane (0.2 g, catalytic amount), palladium(II)acetate (0.1 g, catalytic amount) and dioxane saturated with $NH_3$ (20 mL) were added before the reaction mixture was stirred at 70° C. for 8 hours. The solvent was removed in vacuo. The residue was dissolved in diethyl ether/$NH_3$ (2M). The layeres were separated and the water phase was extracted twice with diethyl ether. The combined organic layers were dried ($MgSO_4$). The solvent was removed in vacuo to give an orange oily residue which was purified by flash chromatography [$SiO_2$, $CH_2Cl_2$:EtOAc,4:1 (+0.5% of $NH_3$)] to give the title compound in 21% yield (0.30 g). Mp 178°–180° C. Mass spectrum (70 eV) m/z (relative intensity) 288(5, M+), 176(11), 175(100), 174(22), 158(13), 131(25), 130(42), 51(19), 44(16).

b) (R)-5-Carbamoyl-2-aminochroman (R)-5-Carbamoyl-2-N-trifluoroacetylaminochroman (0.30 g, 1.04 mmol) was dissolved in $CH_2Cl_2$ (50 mL).

Sodium hydroxide (5 mL of 15% in water) was added and the mixture was stirred for 4 hours. The layers were separated and the water phase was extracted with $CH_2Cl_2$ four times. The organic layers were combined and the solvent was removed in vacuo to give a solid residue which was suspended in diethyl ether (300 mL) and filtered. The ether was removed in vacuo to give the title compound in 90% yield (180 mg). mp 194°–196° C. $[\alpha]_D^{21}$ –36° (MeOH. c 10 mg/mL). Mass spectrum (70 eV) m/z (relative intensity) 192(1, M+), 176(26), 175(100), 160(13), 130(14), 51(22), 44(13), 43(83), 42(15).

Example 85

(R)-2-N,N-Dibenzylamino-5-methoxycarbonylchroman a) (R)-2-N,N-dibenzylamino-5-methoxy-chroman (R)-5-Methoxy-2-aminochroman (2.6 g, 14 mmol), $K_2CO_3$ (7.0 g, 51 mmol), benzyl bromide (6.0 g, 35 mmol) and a catalytic amount of KI were mixed in acetonitrile (100 mL) under a nitrogen atmosphere. The reaction mixture was stirred at 85° C. for about 72 hours. The solvent was removed in vacuo and the residue was dissolved in diethyl ether/$NH_3$ (2M). The layers were separated and the water phase was extracted twice with diethyl ether. The ether layers were combined and dried ($MgSO_4$). The solvent was removed in vacuo to give a yellow oily residue which was purified by flash chromatography ($SiO_2$,n $CH_2Cl_2$) to give the title compound in 64% yield (3.2 g). The HCl salt was precipitated from diethyl ether at 0° C. and then recrystallized from EtOH/diethyl ether. The crystalls are hygroscopic and starts to melt very slowly from 100° C. and melt finally between 118° and 120° C. $[\alpha]_D^{21}$ –20° (c 33 mg/mL, the HCl salt in MeOH). Mass spectrum (70 eV) m/z (relative intensity) 360(19), 359(91,M+), 268(16), 223(11), 210(15), 132(72), 91(100).

b) (R)-2-N,N-Dibenzylamino-5-hydroxy-chroman (R)-2-N,N-Dibenzylamino-5-methoxychroman hydrochloride (1.6 g, 4.0 mmol) was dissolved in $CH_2Cl_2$ (40 mL) under a nitrogen atmosphere. The solution was then cooled to –70° C. $BBr_3$ dissolved in $CH_2Cl_2$ (25 mL) was added dropwise under a 5 minutes period. The reaction mixture was then warmed up slowly to 0° C. and stirred at that temperature over night. The reaction mixture was slowly poured into a stirred saturated solution of $NaHCO_3$. The layers were separated and the water phase was extracted three times with $CH_2Cl_2$. The organic layers were combined and dried ($MgSO_4$). The solvent was removed in vacuo to give a brownish oily residue which was purified by flash chromatography ($SiO_2$, $CH_2Cl_2$) to give the title compound in 98% yield (135 mg). $[\alpha]_D^{21}$ –94° (c 10 mg/mL, MeOH). Mass spectrum (70 eV) m/Z (relative intensity) 346(26), 345(100), 132(13), 91(11).

c) (R)-2-N,N-Dibenzyl-5-trifluoromethanesulfonyloxy-chroman (R)-2-N,N-Dibenzylamino-5-hydroxychroman (1.5 g, 4.3 mmol) and collidine (0.6 g, 5.2 mmol) were dissolved in $CH_2Cl_2$ (30 mL) under a nitrogen atmosphere. The solution was cooled to –70° C. and trifluoromethanesulfonic anhydride (1.3 g, 4.7 mmol), dissolved in $CH_2Cl_2$ (20 mL), was added dropwise during a 10 minutes period. The cooling bath was removed and the reaction mixture was slowly warmed up to room temperature (21° C.). The reaction mixture was washed with $NH_3$ (2M) and dried ($MgSO_4$). The solvent was removed in vacuo to give an orange solid residue which was purified by flash chromatography ($SiO_2$, $CH_2Cl_2$) to give the title compound in 90% yield (1.85 g). $[\alpha]_D^{21}$ –83° (c 20 mg/mL, MeOH). Mass spectrum (70 eV) n/z (relative intensity) 477(14, M+), 345(25), 344(100), 132(31, 91(78).

d) (R)-2-N,N-Dibenzylamino-5 methoxycarbonylchroman (R)-2-N,N-Dibenzylamino-5-trifluoromethanesulfonyloxychroman (1.8 g, 3.8 mmol) and triethylamine (0.8 g, 8.3 mmol) were dissolved in a solution of DMF/MeOH (20 mL, 6:2) in a three necked round bottom flask. The flask was evacuated, followed by inlet of CO gas (repeated three times). Palladium(II)acetate (28 mg, catalytic amount) and 1,3-bis(diphenylphosphino)-propane (60 mg, catalytic amount) were added and the reaction mixture was stirred at 75° C. for 6 hours. The solvent was removed in vacuo to give a brownish oily residue. The oil was dissolved in diethyl ether/$NH_3$ (2M). The layers were separated and the water phase was extracted once with diethyl ether. The combined ether layers were dried ($MgSO_4$). The solvent was removed in vacuo to give a brown oily residue which was purified by flash chromatography ($SiO_2$, $CH_2Cl_2$/hexane, 1:1) to give the title compound in 95% yield (1.4 g). $[\alpha]_D^{21}$ –147° (c 5 mg/mL, MeOH). Mass spectrum (70 eV) m/z (relative intensity) 388(25), 387(100, M+), 297(10), 296(62), 264(27), 132(40), 91(79).

Example 86

(R)-5-Carbamoyl-2-N,N-dibenzylchroman (R)-2-N,N-Dibenzylamino-5-methoxycarbonylchroman (1.4 g, 3.6 mmol) was dissolved in MeOH (20 mL). A solution of NaOH (0.16 g, 4.0 mmol) in water (6 mL) was added and the reaction mixture was refluxed over night. The solvent was removed in vacuo. Toluene was added and the solvent was removed again (repeated twice in order to remove the water). The residue was dissolved in $SOCl_2$ (6 mL) and refluxed for 1 hour. The solvent was removed in vacuo. The residue was dissolved in $CH_2Cl_2$ (20 mL) and $NH_3$-gas was flushed through the solution for 2 minutes. The reaction mixture was stirred at r.t. for 1 hour before washing (2M $NH_3$) and dried ($MgSO_4$). The solvent was removed in vacuo to give a crude brownish oily residue which was purified by flash chromatography [$SiO_2$, $CH_2Cl_2$/EtOAc, 5:1(+0.5% of $NH_3$)] to give the title compound in 41% yield (0.55 g). $[\alpha]_D^{21}$ –129° (c 10 mg/mL, MeOH). Mass spectrum (70 eV) m/z (relative intensity) 372 (2, M+), 281(43, 264(27), 132(19), 106(12), 105(18), 91(100), 77(12), 65(25), 32(22).

Example 87

(R)-5-[1-methyl(5-imidazolyl)]-3-(N-isopropyl-N-n-propylamino)chroman (R)-5-Formyl-3-(N-isopropyl-N-n-propylamino)chroman (0.4 g, 1.5 mmol) was dissolved in methanol (15 mL), saturated with methylamine. Some molcular sieves (3 Å) were added. The solvent was removed in vacuo. The residue was dissolved in methanol (30 mL) under nitrogen atmosphere. Tosylmethylisocyanide (0.36 g, 1.8 mmol) and $K_2CO_3$ (0.25 g, 1.8 mmol) were added and the reaction mixture was reluxed for 1 hour. Additionally tosylmethylisocyanide (0.36 g, 1.8 mmol) and $K_2CO_3$ (0.25 g, 1.8 mmol) were added and the reflux was continued for 3 hours. Tosylmethylisocyanide (0.1 g, 5.2 mmol) was added once more and the reflux was continued for 12 hours. The solvent was removed in vacuo. The residue was dissolved in diethyl ether/2M $NH_3$. The layers were separated and the water-phase was extracted once more with ether. The organic layers were combined and dried ($Na_2SO_4$). The solvent was removed in vacuo to give a brown oily residue which was purified by flash chromatography ($SiO_2$, first $CH_2Cl_2$/EtOAc, 5:1, also containing 0.5% of $NH_3$ and then EtOAc/EtOH, 50:1+0.5% of $NH_3$) to give 200 mg of the title compound (42 yield). $[\alpha]_D^{21}$ –37° (c 30 mg/mL, MeOH). The HCl-salt was precipitated from diethyl ether at 0° C. and recrystallized from ethanol/diethyl ether. mp 159°–161° C. (dec).

Example 88

(R)-3-(N-Isopropyl,N-n-propylamino)-5-(N-Isopropyl)carbamoylchroman.

a) (R)-3-(N-Isopropyl,N-n-propylamino)-5-methoxycarbonylchroman (R)-3-(N-Isopropyl,N-n-propylamino)-5-trifluoromethanesulfonyloxychroman (4.0 g, 10.5 mmol), triethylamine (2.3 g, 23.1 mmol) and a mixture of DMF/MeOH (18 mL, 6:2) was mixed in a three necked round-bottom flask. The flask was evacuated followed by inlet of CO-gas (repeated two times). Finally 1,3-bis (diphenylphosfino)propane (0.11 g, catalytic amount) and palladium(II)acetate (0.07 g, catalytic amount)) was added before the mixture was stirred at 70° C. for 17 hours. The recation mixture was diluted with diethyl ether, washed with 2M $NH_3$ and dried ($MgSO_4$). Removal of solvent in vacuo gave a brown oily residue which was purified by flash chromatography ($SiO_2$, $CH_2Cl_2$/EtOAc; 10:1) to give the title compound in 82% yield (2.5 g). $[\alpha]_D^{21}$ –131.6° (MeOH 0.1M, 21° C.). Mp 125.5°–127.4° C. Anal. Calcd for $C_{17}H_{26}O_3NCl$: C, 62.3; H, 8.0; N, 4.3. Found: C, 62.5; H, 7.9; N, 4.4.

b) (R)-3-(N-Isopropyl,N-n-propylamino)-5-(N-Isopropyl)carbamoylchroman (R)-3-N-(N-Isopropyl,N-n-propylamino)-5-methoxycarbonylchroman (0.46 g, 1.6 mmol), dissolved in MeOH (10 mL), was mixed with a solution of NaOH (0.06 g, 1.6 mmol) in water (3 mL). The reaction mixture was then refluxed for 3.5 hours before the solvent was removed in vacuo. The residue was dissolved in toluene. The toluene was removed in vacuo (repeated two times) in order to form an azeotrope to remove the water. The carboxylic acid was then dissolved in $SOCl_2$ (5 mL) and refluxed for 1 hour. The excess of $SOCl_2$ was removed in vacuo. The acid chloride was then dissolved in $CH_2Cl_2$ (20 mL, dried with molecular sieves 3 Å) before 4 mL of isopropylamine was added. The reaction mixture was stirred for 1 hour at room temperature (21° C.) before it was diluted with diethyl ether, washed (2M $NH_3$) and dried ($MgSO_4$). Removal of solvent in vacuo gave a yellow oily residue which was purified by flash chromatography ($SiO_2$, $CH_2Cl_2$/EtOAc; 5:2) to give the pure title compound in 88% yield (0.46 g). $[\alpha]_D^{21}$ –90.4° (MeOH, 0.1M, 21° C.). Mp 92.5°–94° C.

Example 89

(R)-8-Fluoro-3-(N-isopropyl-N-propylamino)-5-N-isopropylcarbamoylchroman (R)-8-Fluoro-3-(N-isopropyl-N-propylamino)-5-trifluoromethanesulfonylchroman (0.405 g, 1.01 mmol) was dissolved in 4 mL dioxane and the solution was degassed (10 mmHg, RT, 5 min.) Then subjected to CO atmosphere.

Then palladium acetate (7 mg), 1,3-bis-diphenylphosphinopropane (12 mg), and isopropylamine (0.44 mL, 5.0 mmol) were added. The resulting solution was again subjected to CO atmosphere and heated to 80° C. with stirring for 4 hours. The reaction was allowed to cool, filtered through celite, and the solvent was removed in vacuo to give the crude residue.

Chromatography on silica (eluent: 35% EtOAc/hexane) gave 0.24 g (71% yield) of the title compound as a clear oil that slowly crystallized. Mp 56°–60° C. $[\alpha]_D^{21}$ –82.2° (c 0.1, $CHCl_3$).

Example 90

(R) -8-Fluoro-3-(N,N-dipropylamino)-5-(N-methylcarbamoyl)chroman hydrochloride

A mixture of (R)-8-fluoro-3-(N,N-dipropylamino)-5-trifluoromethanesulfonylchromane (0.47 g), Pd(II)acetate (7 mg), 1,3-bis (diphenylphosphino)propane (14 mg), methylamine (25 ml of 1M solution in dioxane) was stirred under a carbon monoxide atmosphere (1 atm) at 70° C. for 22 hours. Aqueous work up followed by column chromatography on silica (4% EtOH in $CHCl_3$) gave (R)-8-fluoro-3-(N,N-dipropylamino)-5-(N-methylcarbamoyl)chroman (0.20 g; 55% yield) as an oil which crystallized. Mp. 72°–73° C. (from ether-hexane) $[\alpha]_D^{20}$ –92.1° (c 1.0, $CHCl_3$). Treating an ethereal solution of the base with an excess of HCl in ether gave the title compound as a white solid which was dried in vacuum at 60° C. Mp. 85°–130° (sintered).

Example 91

(R)-3-(N-cyclopentyl, N-n-propylamino)-8-fluoro-5-methylcarbamoylchroman a) (R)-3-N-cyclopentylamino-8-fluoro-5-methoxychroman (R)-3-amino-5-methoxychroman (1.5 g, 7.6 mmol), acetic acid (0.45 g 7.6 mmol), and cyclopentanone (2.5 g, 3 mmol) were dissolved in 30 ml of methanol. With stirring, sodiumcyanoborohydride (0.8 g, 13 mmol) was added in portions in a few minutes. Stirring was continued for 2 hours. A GC sample showed 100% of a new product. The solvent was evaporated and water, 2 molar ammonia and EtOAc were added. The organic layer was separated and washed neutral with water. The layer was dried with $Na_2SO_4$ and evaporated to give 1.3 g (64% yield) of an colourless oil. GC/MS with the molecular peak of 265 confirmed the title compound.

b) (R)-3-(N-cyclopentyl, N-n-propylamino)-8-fluoro-5-methoxychroman (R)-3-N-cyclopentylamino-5-methoxychroman (1.3 g, 5 mmol), acetic acid (0.3 g, 5 mmol) and propionic aldehyde (1.5 g, 25 mmol) were dissolved in 30 ml of methanol. With stirring, sodiumcyanoborohydride (0.8 g, 13 mmol) was added in portions in a few minutes and stirring was continued. After 3 hours a GC sample showed 100% of a new product. The solvent was evaporated and water, 2 molar $NH_3$ and EtOAc were added. The organic layer was separated and washed neutral with water. The layer was dried with $Na_2SO_4$ and evaporated to give 1 g (65% yield) of an colourless oil. GC/MS with the molecular peak of 307 confirmed the title compound.

c) (R)-3-(N-cyclopentyl, N-n-propylamino)-8-fluoro-5-hydroxychroman (R)-3-(N-cyclopentyl,N-n-propylamino)-8-fluoro-5-methoxychroman (1 g, 5 mmol) was dissolved in 25 ml of $CH_2Cl_2$. An excess of etheric HCl was added to form the HCl salt. A solution of $BBr_3$ (4 g, 15 mmol) in 10 ml of $CH_2Cl_2$ was prepared and added droppwise in 10 minutes with stirring on an ice-bath. The reaction mixture was allowed to reach room temperature during continued stirring for 6 hours and the mixture was poured out into ice water and made alkaline by adding ammonia. The organic layer was separated, dried with $Na_2SO_4$ and evaporated to afford a darkbrown oil. Chromatography ($SiO_2$, di-isopropylether and hexane 1+1) afforded 1.1 g of an colourless oil. The HCl salt was prepared from the base and etheric HCl and rerystallized from acetonitrile to give 0.85 g (52% yield). Mp 220°–221° C.

d) (R)-3-(N-cyclopentyl,N-n-propylamino)-8-fluoro-5-trifluoromethylsulphonatechroman (R)-3-(N-cyclopentyl,N-n-propylamino)-8-fluoro-5-hydroxy-chroman (0.7 g, 3 mmol) was dissolved in 25 ml of $CH_2Cl_2$ and triethylamine (0.3 g, 3 mmol) was added. The solution of triphlate anhydride (1 g, 4 mmol) in 5 ml of $CH_2Cl_2$ was added dropwise in 10 min at (–20° C. Stirring was continued for further 1 hour. The reaction mixture was poured out into ice water and the pH was adjusted to 8 by addition of ammonia and extracted by ether. The organic layer was separated, dried with $Na_2SO_4$ and evaporated to afford a brown oil. Chromatography ($SiO_2$, $CH_2Cl_2$+hexane, 1+3) afforded 0.5 g (44% yield) of a colourless oil. GC/MS with the molecular pek of 425 confirmed the title compound.

e) (R)-3-(N-cyclopentyl,N-n-propylamino)-8-fluoro-5-methylcarbamoylchroman (R)-3-(N-cyclopentyl,N-n-propylamino-8-fluoro-5-trifluoromethylsulphonatechroman (0.5 g, 1 mmol) was dissolved in 15 ml of 1,4-dioxane. Palladium II acetate (10 mg), 1,3-bis (diphenylphosphino)-propane (20 mg), and methylamin (0.15 g, 5 mmol) were added and the mixture was stirred in carbon monoxide atmosphere over night at 70° C. Evaporation and chromatography ($SiO_2$, diethyleter+hexane 1+3) afforded the final compound as a colourless oil. The HCl salt was prepared to give 0.24 g (65% yield) of white crystals. Mp 108° C.

Example 92

(R)-5-Carbamoyl-8-Fluoro-3-(N-3-pentyl-N-n-propylamino)chroman a) (R)-8-Fluoro-5-methoxy-3-(N-3-pentylamino) chroman To a stirred solution of (R)-8-fluoro-5-methoxy-3-aminochroman (3.13 g, 15.9 mmol) and 3-pentanone (2.2 ml, 20.8 mmol) in 100 ml dry MeOH, $NaBH_3CN$ (1.31 g, 20.8 mmol) was added during 10 min. The pH was adjusted to pH was adjusted to pH 6 with acetic acid and the solution was stirred at room temp. After 18 hours, 3-pentanone (0.5 ml, 4.7 mmol) was added and the solution was stirred at room temp. for 3 hours. Concentration and extraction with 100 ml 2M $NH_3$ and 2×250 ml EtOAc, drying of the combined organic phases ($Na_2SO_4$) and evaporation gave a crude product that was purified by flash chromatography on silica with hexane:EtOAC:$NH_3$, 60:40:0.5, to give 3.75 g of (R)-8-fluoro-5-methoxy-3-(N-3-pentylamino)chroman as an uncolored oil. $[\alpha]_D^{22}$ –25° (c 1.14 in MeOH).

b) (R)-8-Fluoro-5-methoxy-3-(N-3-pentyl-N-n-propylamino)chroman

Sodiumcyanoborohydride (1.3 g, 20.7 mmol) was added during 10 min. to a stirred solution of (R)-8-fluoro-5-methoxy-3-(N-3-pentylamino)chroman (3.69 g, 13.8 mmol) and propionaldehyde (5 ml, 69.3 mmol) in 100 ml dry MeOH. The pH was adjusted with acetic acid to pH 6. The solution was stirred in room temp. for 18 hours and propionaldehyde (1 ml, 13.7 mmol) was added. After stirring at room temp. for 3.5 hours the solution was concentrated, and the residue was partitionated between 100 ml 2M $NH_3$ and 200 ml ether. Extraction with 2×200 ml ether and drying of the combined organic layers ($Na_2SO_4$) gave after evaporation a crude product. Purification by flash chromatography on silica with hexane:acetone 20:1 gave 4.03 g of (R)-8-fluoro-5-methoxy-3-(N-3-pentyl-N-n-propylamino) chroman as an uncolored oil. $[\alpha]_D^{22}$ –83° (c 1.08 in MeOH).

c) (R)-8-Fluoro-5-methoxy-3-(N-3-pentyl-N-n-propylamino)chroman hydrochloride (R)-8-Fluoro-5-methoxy-3-(N-3-pentyl-N-n-propylamino)chroman (4.59 g, 14.8 mmol) was dissolved in ether. HCl in ether was added to precipitate the HCl-salt, and gave after drying 4.59 g of (R)-8-fluoro-5-methoxy-3-(N-3-pentyl-N-n-propylamino)chroman hydrochloride as a white powder. Mp. 30°–50° C. (sinters).

d) (R)-8-Fluoro-5-hydroxy-3-(N-3-pentyl-N-n-propylamino)chroman

Demethylation was done by addition of $BBr_3$ (2.6 ml, 27.5 mmol) in 10 ml dry $CH_2Cl_2$ during 20 min., to a stirred, cooled solution (–70° C.) of (R)-8-fluoro-5-methoxy-3-(N-3-pentyl-N-n-propylamino)chroman hydrochloride (4.44 g, 12.8 mmol) in 100 ml dry $CH_2Cl_2$ under $N_2$ atmosphere and dry conditions. The solution was stirred for 1 hour at –70° C., 1 hour at 0° C. and 1 hour at room temp. and was thereafter poured into 80 ml saturated $NaHCO_3$ aq. under vigirous stirring. After 0.5 hour the layers where separated and the aqueous phase was extracted with 2×150 ml $CH_2Cl_2$. The combined organic layers where dried ($Na_2SO_4$) and evaporated. The crude product was purified by flash chromatography on silica with a gradient of petroleumether-petroleumether: EtOAc, 4:1 to give 3.72 g of (R)-8-fluoro-5-hydroxy-3-(N-3-pentyl-N-n-propylamino)chroman (NAG 134) as an yellow-brown oil. $[\alpha]_D^{22}$ –85° (c 1.02 in MeOH).

e) (R)-8-Fluoro-5-hydroxy-3-(N-3-pentyl-N-n-propylamino)chroman hydrochloride (R)-8-Fluoro-5-hydroxy-3-(N-3-pentyl-N-n-propylamino)chroman (180 mg, 0.6 mmol) was dissolved in ether. HCl in ether was added to precipitate the HCl-salt, and gave after drying 200 mg of (R)-8-fluoro-5-hydroxy-3-(N-3-pentyl-N-n-propylamino)chroman hydrochloride as a white powder. Mp: 80°–100° C. (sinters).

f) (R)-8-Fluoro-3-(N-3-pentyl-N-n-propylamino)-5-trifluoromethanesulfonyloxychroman To a stirred, cooled solution (–72° C.) of (R)-8-fluoro-5-hydroxy-3-(N-3-pentyl-N-n-propylamino)chroman (3.53 g, 11.9 mmol), triethylamine (3.33 ml, 23.9 mmol) and DMAP (catalytic amount) in 95 ml dry $CH_2Cl_2$, under nitrogen atmosphere and dry conditions, trifluoromethanesulfonic anhydride (3 ml, 17.8 mmol) in 5 ml dry $CH_2Cl_2$ was added during 25 min. The uncolored solution turns to light yellow, and then to black. After 30 min. at –70° C. The solution was extracted with 100 ml $H_2O$. The aqueous phase was extracted with 100 ml $CH_2Cl_2$. The combined organic layers gave after drying ($MgSO_4$) and evaporation a brown-yellow oil. The crude product was purified by flash chromatography on silica with a gradient of hexane-hexane:EtOAc, 9:1 and gave 3.69 g of (R)-8-fluoro-3-(N-3-pentyl-N-n-propylamino)-5-trifluoromethanesulfonyloxychroman as an uncolored oil. $[\alpha]_D^{22}$ –62° (c 1.02 in MeOH).

g) (R)-8-Fluoro-3-(N-3-pentyl-N-n-propylamino)-5-trifluoromethanesulfonyloxychroman hydrochloride (R)-8-Fluoro-3-(N-3-pentyl-N-n-propylamino)-5-trifluoromethanesulfonyloxychroman (100 mg, 0.23 mmol) was dissolved in ether. HCl in ether was added to precipitate the HCl-salt, and gave after drying 110 mg of (R)-8-fluoro-3-(N-3-pentyl-N-n-propylamino)-5-trifluoromethanesulfonyloxychroman hydrochloride as a white powder. Mp. 45°–60° C. (sinters).

h) (R)-8-Fluoro-5-methyloxycarbonyl-3-(N-3-pentyl-N-n-propylamino)chroman (R)-8-Fluoro-3-(N-3-pentyl-N-n-propylamino)-5-trifluoromethanesulfonyloxychroman (1.04 g, 2.43 mmol), palladium(II)acetate (55 mg), 1,2-bis(diphenylphosphino) propane (100 mg) was dissolved in 10 ml DMF. Triethylamine (0.75 ml, 5.38 mmol) and MeOH (1.0 ml, 24.6 mmol) was added under CO atm. via septa. The solution was stirred at +70° C. for 18 hours, and thereafter evaporated to dryness. 100 ml 2M $NH_3$ and 100 ml EtOAc was added and the aqueous phase was extracted with 100 ml EtOAc. The combined organic layers was dried ($MgSO_4$) and evaporated. Flash chromatography on silica with a gradient of Hexane-Hexane:EtOAc, 50:1 gave 0.76 g of (R)-8-fluoro-5-methyloxycarbonyl-3-(N-3-pentyl-N-n-propylamino) chroman as an uncoloured oil. Purity: 94% according to GC.

i) (R)-5-Carbamoyl-8-Fluoro-3-(N-3-pentyl-N-n-propylamino)chroman (R)-8-Fluoro-5-Methyloxycarbonyl-3-(N-3-pentyl-N-n-propylamino)chroman (0.72 g, 2.13 mmol) was hydrolysed with KOH (0.20 g, 3.1 mmol) in 20 ml MeOH and 10 ml $H_2O$, under reflux conditions for 20 hours and gave after evaporation, and co-evaporation with toluene, (R)-8-fluoro-5-carboxy-3-(N-3-pentyl-N-n-propylamino)chroman as a white solid. $SOCl_2$ (0.8 ml, 11 mmol) was added to a slurry of (R)-8-fluoro-5-carboxy-3-(N-3-pentyl-N-n-propylamino) chroman in 50 ml dry $CH_2Cl_2$ and 1 drop DMF (catalytic amount). After reflux for 2 hours, the slurry was evaporated, and the residue, dissolved in 10 ml dry THF was added dropwise to 35 ml ice-cooled conc. $NH_3$ under stirring. The THF was evaporated after 2 hours and extraction with EtOAc×2, drying ($Na_2SO_4$) and evaporation gave 0.51 g of a crude product. Purification by flash chromatography with hexane:EtOAc:$NH_3$, (60:40:0.5) gave 0.41 g of (R)-5-carbamoyl-8-fluoro-3-(N-3-pentyl-N-n-propylamino) chroman as light yellow crystals.

Recrystallisation was made from EtOAc/hexane. $[\alpha]_D^{22}$ −103° (c 1.0 in MeOH), Mp: 111°–113° C.

Example 93

(R)-8-fluoro,3-(N-isopropyl,N-propylamino)5-carbamoylchroman hydrochloric acid a) (R)-8-Fluoro-5-methoxycarbonyl-3-(N-isopropyl,N-propylamino)chroman (R)-8-Fluoro-3-(N-isopropyl,N-propylamino)-5-trifluoromethanesulfonyloxychroman (2.4 g, 6.0 mmol), triethylamine (1.3 g, 12.9 mmol), 1,3-bis(diphenylphosphino) propane (95 mg, catalytic amount), palladium(II)acetate (48 mg, catalytic amount) and DMF/MeOH (30 mL, 3:1) were mixed in a 50 mL three necked round bottom flask. The flask was evacuated followed by the inlet of CO (repeated two times). The reaction mixture was stirred at 70° C. for 7.5 hours. The solvent was removed in vacuo and the residue was dissolved in diethyl ether/sat: $NaHCO_3$. The layers were separated and the water phase was extracted once with ether. The combined ether layers were dried ($MgSO_4$) and the solvent was removed in vacuo to give a crude which was purified by flash chromatography ($SiO_2$, hexane/EtOAC, 9:1) to give 1.3 g of the title compound (71% yield).

b) (R)-8-fluoro, 3-(N-isopropyl,N-propylamino)5-carbamoylchroman hydrochloric acid (R)-8-Fluoro-5-methoxycarbonyl-3-(N-isopropyl,N-propylamino)chroman (1.3 g, 4.2 mmol) and KOH (0.52 g, 8.4 mmol) were mixed in methanol (6 mL) and refluxed for 2.5 hours. The solvent was removed in vacuo. The residue was dissolved in water and made acidic by the addition of 2M HCl. The solvent was removed in vacuo. The residue was dissolved in $SOCl_2$ (30 mL) and refluxed for 2.5 hours. The solvent was removed in vacuo. The residue was dissolved in $CH_2Cl_2$ and the solvent was removed in vacuo again (repeated three times in order to remove the excess of $SOCl_2$. The residue was then dissolved in diethyl ether (50 mL). The solution was cooled to −30° C. before $NH_3$ (g) separated and the water-phase was extracted with ether. The combined ether layers were dried ($K_2CO_3$) and the solvent was removed in vacuo to give a crude which was purified by flash chromatography ($SiO_2$, EtOAc/hexane, 1:1) to give 1.0 g of the title compound (yield 80%). Recrystallization from EtOAc/hexane gave crystals with Mp 139°–140° C. The resulting compound is an 5-$HT_{1A}$ antagonist.

A Preferred Embodiment

It has turned out that various compounds tested within the invention show a great variability in the three different parameters: selectivity for 5-$HT_{1A}$ receptors, agonist/antagonist functional effects in rats and bioavailability after oral administration of the test compound. It has been difficult to identify compounds possessing all three advantageous properties. There is no guidance in the prior art how to obtain compounds with this combination of properties.

Surprisingly, it has been found that the racemic compound of the invention, 3-(N-isopropyl-N-n-propylamino)-5-(N-isopropyl)carbamoylchroman shows excellent bioavailability, and possess a high affinity to a specific subgroup of 5-hydroxytryptamine receptors in CNS, the 5-$HT_{1A}$.

Furthermore, it has been found that high affinity for the 5-$HT_{1A}$-receptor in CNS is strictly stereospecific as regards the compound, 3-(N-isopropyl-N-n-propylamino)-5-(N-isopropyl)carbamoylchroman. The (R)-enantiomer of 3-(N-isopropyl-N-n-propylamino)-5-(N-isopropyl) carbamoylchroman possesses a high affinity for 5-$HT_{1A}$ receptors in CNS while the (S)-enantiomer of 3-(N-isopropyl-N-n-propylamino)-5-(N-isopropyl) carbamoylchroman lacks activity for 5-$HT_{1A}$ receptors. The (R)-enantiomer of 3-(N-isopropyl-N-n-propylamino)-5-(N-isopropyl)carbamoylchroman shows a good bioavailability, too. Thus, the racemate as well as the (R)-enantiomer of the compound of the invention can be used in the treatment of 5-hydroxytryptamine mediated states and disorders in mammals including man.

The compound of this preferred embodiment of the present invention is 3-(N-isopropyl-N-n-propylamino)-5-(N-isopropyl)carbamoylchroman as racemate and (R)-enantiomer having the formula

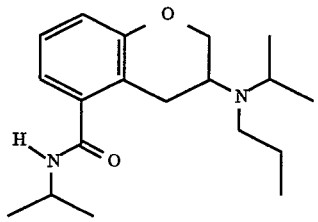

I in the form of free base or pharmaceutically acceptable salts thereof.

Both organic and inorganic acids can be employed to form non-toxic pharmaceutically acceptable acid addition salts of the compound of this invention. Illustrative acids are sulfuric, nitric, phosphoric, oxalic, hydrochloric, formic, hydrobromic, citric, acetic, lactic, tartaric, dibenzoyltartaric, diacetyltartaric, pamoic, ethanedisulfonic, sulfamic, succinic, propionic, glycollic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphtoic, nicotinic, methanesulfonic, ethanesulfonic, hydroxyethanesulfonic, benzenesulfonic, p-toluenesulfonic, sulfanilic, naphthalenesulfonic, ascorbinic, cyclohexylsulfamic, fumaric, maleic and benzoic acids. These salts are readily prepared by methods known in the art.

Preparation

The (R)-enantiomer may be obtained according to known methods such as from racemic diastereomeric salts by means of fractional crystallisation or covalent diastereomers by means of chromatography. The enantiomeric separation may be performed before alkylation of the amino group (Method A) or after N-alkylation (Method B). The scheme below illustrates the Methods A and B in more detail:

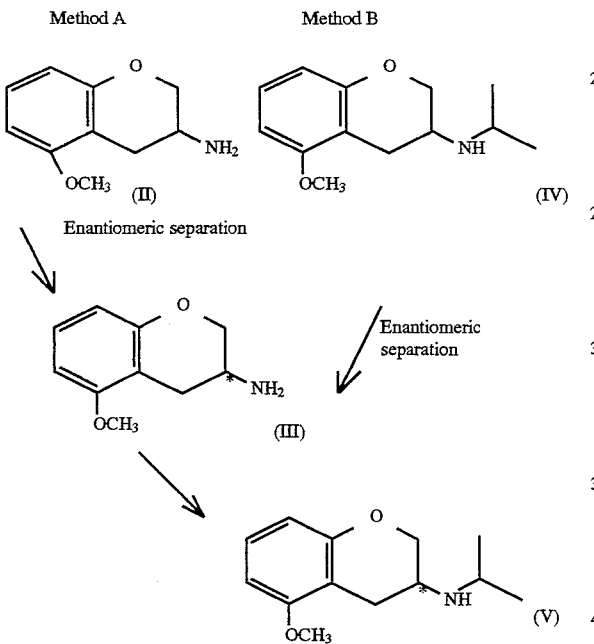

The compound V may be transferred to compound VI by using known method steps such as N-alkylation, demethylation and finally conversion to the leaving group Y.

The preparation of the racemic compound of the invention may start from the compound 5-methoxy-3-chromanone (prepared analogously to the description in EP 222 996) followed by known methods such as reductive amination, N-alkylation, demethylation and finally conversion to the leaving group Y to obtain the racemate of compound VI.

The racemic form as well as the (R)-enantiomer of the compound of the invention, may be prepared according to the following methods:

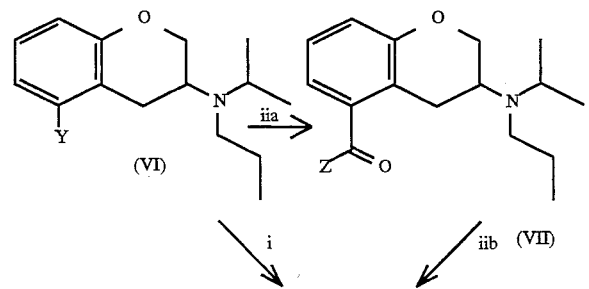

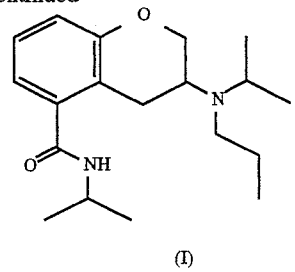

i. converting the compound of formula VI

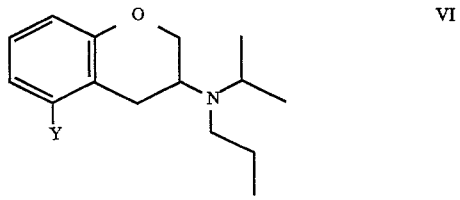

wherein Y is a leaving group such as trifluoromethane sulfonate ($OSO_2CF_3$), halide e.g. Cl, or Br or I by a catalytic cycle using a zerovalent transition metal (M) such as Pd or Ni, which may be generated in situ and undergoes an oxidative addition to the aryl-Y-bond. Treatment with carbon monoxide followed by amination with isopropylamine give the the compound of formula I, whereafter if desired it is converted to a salt.

ii. Alternatively, the compound of formula VI is converted to the compound of formula VII

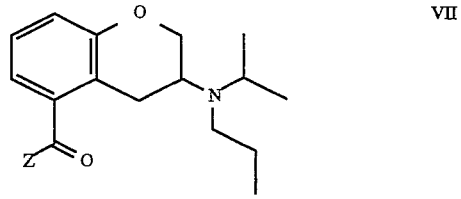

wherein Z is Cl, Br, OH or $OR_p$, where Rp is $C_1$–$C_6$ alkyl, by catalytic cycle using a zerovalent transition metal, with ability to undergo oxidative addition to aryl-Y-bonds e.g. The aryl-$SO_3CF_3$ bonds. The aryl-CO-metal-Y complex is formed by treatment with carbon monoxide (CO).

Further reagents are an alcohol such as methanol, ethanol, a tertiary amine base such as a trialkylamine e.g. triethylamine in an inert organic solvent preferentially a polar aprotic solvent such as dimethylformamide (DMF), dimethylsulfoxide (DMSO), acetone, acetonitrile etc. The reaction is normally performed at a temperature between +40° to +120° C. and at a pressure between 100 to 500 KPa (iia). This is optionally followed by hydrolysis and treatment with a thionyl halide, e.g. thionylchloride, to obtain the corresponding acid halide derivative.

The compound of formula VII is aminated (iib) with isopropylamine in a nonpolar aprotic solvent e.g. toluene, benzene at reflux temperature or between 0° to 100° C. to give the compound of formula I.

Example 94

3-(N-Isopropyl-N-n-propylamino)-5-(N-isopropyl)carbamoyl chroman a) 3-Isopropylamino-5-methoxychroman hydrochloride 5-Methoxy-3-chromanone (16 g, 0.089 mol) and isopropylamine (6.4 g, 0.112 mol) were reacted via reductive amination by known methods (Clinton F. Lane Synthesis 1975 vol. 46 p. 135) to give the title compound. Mp. 255° C.

b) 3-(N-Isopropyl-N-n-propylamino)-5-methoxychroman

A mixture of the product obtained in a) above (14 g, 0.06 mol), 1-iodopropane (15 g, 0.08 mol), $K_2CO_3$ and acetonitrile (250 ml) was stirred under reflux for 4 days. After chromatography the desired product was isolated as a colourless oil. GC-MS(CI-mode) M+1=264 (100%).

c) 3-(N-Isopropyl-N-n-propylamino)-5-hydroxychroman

The product from b) above (10 g, 0.038 mol) was demethylated using $BBr_3$ in dichloromethane. GC-MS(CI-mode) M+1=250 (100%).

d) 3-(N-Isopropyl-N-n-propylamino)-5-trifluoromethanesulfonoxychroman

The product from c) above (10 g, 0.04 mol) was dissolved in $CH_2Cl_2$ and cooled to −30° C. Pyridine (6 g, 0.076 mol) was added followed by trifluoromethanesulfonic anhydride (14 g, 0.05 mol). The solution was stirred at −20° C. for 3 hours and then allowed to reach ambient temperature. The solution was washed with aqueous $NaHCO_3$, dried with $Na_2SO_4$ and evaporated to dryness. The oil was finally purified by flash chromatography (silica gel) by elution with ethyl acetate/hexane 1:9. GC-MS(CI-mode) M+1=382 (100%)

e) 3-(N-Isopropyl-N-n-propylamino)-5-(N-isopropyl)carbamoylchroman

A mixture of the product from d) above (3 g; 0.008 mL), 1,3-bis(diphenylphosphine)propane (150 mg), palladium (II) acetate (75 mg), and isopropylamine (5 ml) in 30 ml DMF was placed in a Parr glass vessel. CO at 2 bar was added and the mixture was shaken at 60° C. for 4 hours. After work up and chromatographic purification the desired compound was obtained as white crystals with mp 124° C. (base).

Example 95

(R)-3-(N-isopropyl-N-n-propylamino)-5-(N-isopropyl)carbamoylchroman (I) (Method A)

a) 3-Amino-5-methoxychroman hydrochloride (II)

3-Amino-5-methoxychroman was prepared according to known methods (Acta Pharm. Suec. 24, 169–182, 1987). Mp: 237°–238° C.

b) (R)-3-Amino-5-methoxychroman (III)

The racemic 3-amino-5-methoxychroman as base (1.0 g; 5.5 mmol) and L(+)tartaric acid (1.0 g; 6.6 mmol) were dissolved in water (20 ml). The solution was heated to 70° C. and the clear solution was allowed to crystallize at room temperature overnight. The precipitate was filtered off giving 0.7 g of the tartrate salt with 99% optical purity of the (R)-isomer. Alkalization and extraction with $CH_2Cl_2$ drying ($Na_2SO_4$) and evaporation gave 0.35 g (35%) of the title compound as the free base.

$[\alpha]_D^{25}$=−20.8° (C=0.83, $CH_2Cl_2$)

c) (R)-3-(N-Isopropylamino)-5-methoxychroman (V)

(R)-3-Amino-5-methoxychroman (1.0 g; 6 mmol) and acetone (2.5 g; 40 mmol) were mixed with methanol (820 ml), acetic acid (0.4 g; 6.6 mmol) and $NaCNBH_3$ (1.2 g; 19 mmol), pH was adjusted to 6.0 with acetic acid. Stirring was continued at room temperature for 3 days. The mixture was evaporated and the residue was made alkaline and extracted with $CH_2Cl_2$. After drying ($Na_2SO_4$) and evaporation the title compound as base was transformed to the HCl-salt. Yield: 1.1 g (83%). Mp: 289° dec.

$[\alpha]_D^{25}$=−29° (C=0.015; MeOH)

d) (R)-3-(N-Isopropyl-N-n-propylamino)-5-methoxychroman (R)-3-(N-Isopropylamino)-5-methoxychroman (17.5 g, 0.079 mol) was dissolved in dimethylformamide (DMF) (180 mL). $K_2CO_3$ (21.8 g, 0.18 mol) and 1-iodopropane (53.8 g, 0.32 mol) were added. The reaction mixture was then stirred at 50° C. for 5 days. The solvent was removed in vacuo. The residue was dissolved in ether/$NH_3$ (1M). The phases were separated and the water phase was washed once with ether. The combined ether-layers were dried ($MgSO_4$) and the solvent was removed in vacuo to give a yellow oily residue. The oil was dissolved in dry ether and title compound was obtained in form of the HCl-salt in 66% yield (15.7 g) by slow addition of HCl in ether at 0° C. Mp (HCl-salt): 108°–120° C.

$[\alpha]_D^{25}$=(Base)=−95.5° (C=0.1;MeOH)

e) (R)-5-Hydroxy-3-(N-isopropyl-N-n-propylamino)chroman

The HCl-salt of (R)-3-(N-isopropyl-N-n-propylamino)-5-methoxychroman (15.5 g, 52 mmol) was mixed with $CH_2Cl_2$ (100 mL) under nitrogen atmosphere and cooled to −60° C. $BBr_3$(27.2 g, 110 mmol) dissolved in $CH_2Cl_2$ (50 mL), was added slowly. The temperature was then raised to 0° C. and the reaction mixture was stirred at 0° C. for 12 h. The reaction mixture was then slowly added to a stirred saturated $NaHCO_3$ solution. The layers were separated and the water layer was extracted once with $CH_2Cl_2$. The combined organic layers were dried ($MgSO_4$). Removal of the solvent in vacuo gave the phenolic title compound. Yield: 98%.

$[\alpha]_D^{22}$(Base)=−83.0° (C=0 1;MeOH) .Mp(HCl-salt): 215°–222° C. (decomposes).

f) (R)-3-(N-Isopropyl-N-n-propylamino)-5-trifluoromethanesulfonyloxychroman (VI)

(R)-5-Hydroxy-3-(N-isopropyl-N-n-propylamino) chroman (13 g, 52 mmol) was dissolved in $CH_2Cl_2$(100 mL) under nitrogen atmosphere. 2,4,6-Collidine (8.2 g, 68 mmol) was added and the mixture was cooled to −60° C. Trifluoromethanesulfonic anhydride (17.7 g, 62 mmol) was added slowly over a one hour period. The temperature was then raised to 0° C. and the reaction was quenched with saturated $Na_2CO_3$. The layers were separated. The water layer was pH adjusted with $NH_3$(2M) to pH 8 and extracted once with $CH_2Cl_2$. The combined organic layers were dried ($MgSO_4$). Removal of solvent in vacuo gave a brown oily residue which was purified by flash chromatography $SiO_2(CH_2Cl_2)$ to give the triflate compound. Yield: 76% (15 g).

$[\alpha]_D^{22}$=−77.9° (C=0.01;MeOH)

g) (R)-3-(N-Isopropyl-N-n-propylamino)-5-(N-isopropyl)carbamoylchroman (I)

(R)-3-(N-isopropyl-N-n-propylamino)5-trifluoromethanesulfonyloxychroman (5.2 , g, 14 mmol) was dissolved in DMF (30 mL). isopropylamine (10 mL) was added and the vessel was evacuated followed by inlet of CO-gas. This procedure was repeated twice before palladium (II) acetate (90 mg) and 1,3-bis(diphenylphosphino) propane (144 mg) was added. The reaction mixture was then stirred for 10 h at 65° C. The solvent was removed in vacuo. The dark brown residue was dissolved in diethylether/$NH_3$ (1M). The layers were separated and the water-phase was extracted once with ether. The combined ether layers were dried ($MgSO_4$). Removal of solvent in vacuo gave a yellow crystalline residue which was purified by flash chromatography $SiO_2$ ($CH_2CL_2$/EtOAc, 10:1). Recrystallisation from $CH_2Cl_2$/hexane gave the pure amide (R)-3-(N-isopropylamino-N-n-propylamino)-5-(N-isopropyl)carbamoylchroman. Yield: 35% (1.5 g).

$[\alpha]_D^{21}$=−87.0° (C=0.1;MeOH).Mp:94°–95.4° C.

Example 96

(R)-3-(N-Isopropylamino-N-n-propylamino)-5-(N-isopropyl)carbamoylchroman (I) (Method B)

a) (R)-3-(N-Isopropylamino)-5-methoxychroman (V)

5-Methoxy-3-chromanone (50 g, 0.28 mol; described in EP 0 222 996) was dissolved in methanol (300 mL). The solution was cooled to 0° C. before the isopropylamine (70 mL, excess) was added. The pH was adjusted to about 6 by the addition of acetic acid. NaCNBH$_3$ (12 g, 0.19 mol) was added in portions during a one hour period and pH was kept at pH 6. The ice-bath was removed and the mixture was stirred overnight at room temperature. The solvent was removed in vacuo. The residue was dissolved in ether/NH$_3$ (1M). The layers were separated and the amine in the ether layer was subjected to acid-base extraction (HCl(1M)/NH$_3$ (1M)). Drying with MgSO$_4$ and evaporation of solvent gave an colorless crystalline product.

Yield: 87% (54 g). Mp: 255°–56° C. (HCl-salt of the racemic product).

The racemic 3-(N-isopropylamino)-5-methoxychroman (IV; 54 g, 0.224 mol) was mixed with an equimolar amount of (+)-di-1,4-toluoyl-D-tartaric acid (98.6 g, 0.244 mol). The mixture was dissolved in boiling ethanol (170 mL)/acetone (70 mL). The salt started to crystallize in the hot solvent mixture but was not filtered off until the solvent had cooled down to room temperature (20° C.). The salt was then recrystallized nine times from ethanol/acetone (1:5) to give the pure diastereomeric salt. Yield: 35% (54 g) (99% e.e.). Mp: 166°–168° C. The free enantiomer as the base (R)-3-(N-isopropylamino)-5-methoxychroman was obtained by the extraction of the salt in ether/KOH (1M). Yield: 32%, 17.5 g, $[\alpha]_D^{21}$=-32° (C=0.1;MeOH) Mp. 285°–286° C. (HCl-salt)

b) (R)-3-(N-Isopropyl-N-n-propylamino)-5-methoxychroman

The title compound was prepared in the same way as described in Example 1b and obtained in the same amount and with the same physical data as given in Example 2d.

c) (R)-5-Hydroxy-3-(N-isopropyl-N-n-propylamino)chroman

The title compound was prepared in the same way as described in Example 2e and obtained in the same amount and with the same physical data as given in Example 2e.

d) (R)-3-(N-Isopropyl-N-n-propylamino)-5-trifluoromethanesulfonyloxychroman (VI)

The title compound was prepared in the same way as described in Example 2f and obtained in the same amount and with the same physical data as given in Example 2f.

e) (R)-3-(3-N-Isopropyl-N-n-propylamino)-5-(N-isopropyl)carbamoylchroman (I)

The title compound was prepared in the same way as described in Example 2 g and obtained in the same amount and with the same physical data as given in Example 2g.

Example 97 a) (R)-3-(N-Isopropyl,N-n-propylamino)-5-methoxycarbonylchroman (R)-3-(N-Isopropyl,N-n-propylamino)-5-trifluoromethanesulfonyloxychroman (4.0 g, 10.5 mmol), triethylamine (2.3 g, 23.1 mmol) and a mixture of DMF/MeOH (18 mL, 6:2) was mixed in a three necked round-bottom flask. The flask was evacuated followed by inlet of CO-gas (repeated two times). Finally 1,3-bis (diphenylphosphino)propane (0.11 g) and palladium(II) acetate (0.07 g) was added. The mixture was stirred at 70° C. for 17 hours. The reaction mixture was diluted with diethyl ether, washed with 2M NH$_3$ and dried (MgSO$_4$). Removal of solvent in vacuo gave a brown oily residue which was purified by flash chromatography (SiO$_2$, CH$_2$Cl$_2$/EtOAc; 10:1) to give the title compound in 82% yield (2.5 g).

$[\alpha]_D^{21}$=-131.6° (MeOH, 0.1M). GC-MS(70 eV)=291(M$^+$), 262(100%)

b) (R)-3-(N-Isopropyl,N-n-propylamino)-5-N-isopropyl)carbamoylchroman (I)

(R)-3-N-(N-isopropyl,N-n-propylamino)-5-methoxycarbonylchroman (0.46 g, 1.6 mmol), dissolved in MeOH (10 mL), was mixed with a solution of NaOH (0.06 g, 1.6 mmol) in water (3 mL). The reaction mixture was then refluxed for 3.5 hours before the solvent was removed in vacuo. The residue was dissolved in toluene. The toluene was removed in vacuo (repeated two times) in order to form an azeotrope to remove the water. The residue was then dissolved in SOCl$_2$ (5 mL) and refluxed for 1 hour. The excess of SOCl$_2$ was removed in vacuo. The residue was dissolved in CH$_2$Cl$_2$ (20 mL, dried with molecular sieves 3 Å) before 4 mL isopropylamine was added. The reaction mixture was stirred for 1 hour at room temperature (21° C.) before it was diluted with diethyl ether, washed (2M NH$_3$) and dried (MgSO$_4$). Removal of solvent in vacuo gave a yellow oily residue which was purified by flash chromatography (SiO$_2$, CH$_2$Cl$_2$/EtOAc; 5:2) to give the pure title compound in 88% yield (0.46 g).

$[\alpha]_D^{21}$=-90.4° (MeOH 0.1) Mp:93°–94° C.

I claim:

1. A process for preparing (R)-3-amino-5-methoxychroman which comprises the steps of:

(i) dissolving racemic 3-amino-5-methoxychroman and L(+)tartaric acid in water to form the tartrate salt;

(ii) heating the solution until a clear solution is obtained; and (iii) crystallizing the tartrate salt by allowing the solution to cool to room temperature.

* * * * *